US011160982B2

(12) United States Patent
Gallagher et al.

(10) Patent No.: US 11,160,982 B2
(45) Date of Patent: Nov. 2, 2021

(54) METHODS FOR TREATING POST-TRAUMATIC STRESS DISORDER IN PATIENTS VIA RENAL NEUROMODULATION

(71) Applicant: Medtronic Ardian Luxembourg S.a.r.l., Luxembourg (LU)

(72) Inventors: Marcia Gallagher, Santa Rosa, CA (US); Douglas Hettrick, Santa Rosa, CA (US)

(73) Assignee: MEDTRONIC ARDIAN LUXEMBOURG S.A.R.L., Luxembourg (LU)

(*) Notice: Subject to any disclaimer, the term of this patent is extended or adjusted under 35 U.S.C. 154(b) by 120 days.

(21) Appl. No.: 16/026,344

(22) Filed: Jul. 3, 2018

(65) Prior Publication Data
US 2019/0009091 A1 Jan. 10, 2019

Related U.S. Application Data

(60) Provisional application No. 62/528,867, filed on Jul. 5, 2017, provisional application No. 62/570,597, filed on Oct. 10, 2017.

(51) Int. Cl.
*A61N 1/36* (2006.01)
*A61B 18/02* (2006.01)
(Continued)

(52) U.S. Cl.
CPC .......... *A61N 1/36096* (2013.01); *A61B 18/02* (2013.01); *A61N 1/0551* (2013.01);
(Continued)

(58) Field of Classification Search
CPC .. A61N 1/36096; A61N 1/0551; A61N 2/006; A61N 7/00; A61B 18/02;
(Continued)

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

WO WO2013134733 9/2013
WO WO2014150595 9/2014
(Continued)

OTHER PUBLICATIONS

McCubbin et al., "Subclinical Posttraumatic Stress Disorder Symptoms: Relationships with Blood Pressure, Hostility, and Sleep," Cardiovascular Psychiatry and Neurology, Published online: Jun. 15, 2016, vol. 2016, Article ID 4720941, 9 pages.
(Continued)

*Primary Examiner* — Carl H Layno
*Assistant Examiner* — Michael J Lau
(74) *Attorney, Agent, or Firm* — Shumaker & Sieffert, P.A.

(57) ABSTRACT

Methods for treating post-traumatic stress disorder (PTSD) and/or for reducing a risk associated with developing PTSD in patients via therapeutic renal neuromodulation and associated systems are disclosed herein. Sympathetic nerve activity can contribute to several cellular and physiological conditions associated with PTSD as well as an increased risk of developing PTSD following a traumatic event. One aspect of the present technology is directed to methods for improving a patient's calculated risk score corresponding to a PTSD status in the patient. Other aspects are directed to reducing a likelihood of developing PTSD in patients presenting one or more PTSD risk factors. Renal sympathetic nerve activity can be attenuated to improve a patient's PTSD status or risk of developing PTSD. The attenuation can be achieved, for example, using an intravascularly positioned catheter carrying a therapeutic assembly configured to use,
(Continued)

e.g., electrically-induced, thermally-induced, and/or chemically-induced approaches to modulate the renal sympathetic nerve.

20 Claims, 12 Drawing Sheets

(51) Int. Cl.
*A61N 1/05* (2006.01)
*A61B 18/04* (2006.01)
*A61N 7/00* (2006.01)
*A61B 18/18* (2006.01)
*A61N 2/00* (2006.01)
*A61B 18/00* (2006.01)
*A61B 18/08* (2006.01)
*A61B 18/22* (2006.01)

(52) U.S. Cl.
CPC ............... *A61B 18/04* (2013.01); *A61B 18/08* (2013.01); *A61B 18/18* (2013.01); *A61B 18/22* (2013.01); *A61B 2018/0022* (2013.01); *A61B 2018/00434* (2013.01); *A61B 2018/00511* (2013.01); *A61B 2018/00577* (2013.01); *A61B 2018/00666* (2013.01); *A61B 2018/00791* (2013.01); *A61B 2018/00875* (2013.01); *A61B 2018/0212* (2013.01); *A61N 2/006* (2013.01); *A61N 7/00* (2013.01)

(58) Field of Classification Search
CPC ......... A61B 18/04; A61B 18/08; A61B 18/18; A61B 18/22; A61B 2018/0022; A61B 2018/00434; A61B 2018/00511; A61B 2018/00577; A61B 2018/00666; A61B 2018/00791; A61B 2018/00785; A61B 2018/0212
USPC .......................................................... 607/45
See application file for complete search history.

(56) References Cited

U.S. PATENT DOCUMENTS

| | | | |
|---|---|---|---|
| 4,764,504 A | 8/1988 | Johnson et al. | |
| 4,976,711 A | 12/1990 | Parins et al. | |
| 5,300,068 A | 4/1994 | Rosar et al. | |
| 5,358,514 A | 10/1994 | Schulman et al. | |
| 5,423,744 A | 6/1995 | Gencheff et al. | |
| 5,571,147 A | 11/1996 | Sluijter et al. | |
| 5,626,576 A | 5/1997 | Janssen | |
| 5,700,282 A | 12/1997 | Zabara | |
| 5,707,400 A | 1/1998 | Terry, Jr. et al. | |
| 5,865,787 A | 2/1999 | Shapland | |
| 5,944,710 A | 8/1999 | Dev et al. | |
| 5,983,141 A | 11/1999 | Sluijter et al. | |
| 6,004,269 A | 12/1999 | Crowley et al. | |
| 6,009,877 A | 1/2000 | Edwards | |
| 6,066,134 A | 5/2000 | Eggers et al. | |
| 6,099,524 A | 8/2000 | Lipson et al. | |
| 6,117,101 A | 9/2000 | Diederich et al. | |
| 6,149,620 A | 11/2000 | Baker et al. | |
| 6,161,048 A | 12/2000 | Sluijter et al. | |
| 6,219,577 B1 | 4/2001 | Brown, III et al. | |
| 6,224,592 B1 | 5/2001 | Eggers et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,292,695 B1 | 9/2001 | Webster, Jr. et al. | |
| 6,405,732 B1 | 6/2002 | Edwards et al. | |
| 6,506,189 B1 | 1/2003 | Rittman et al. | |
| 6,514,226 B1 | 2/2003 | Levin et al. | |
| 6,522,926 B1 | 2/2003 | Kieval et al. | |
| 6,562,034 B2 | 5/2003 | Edwards et al. | |
| 6,635,054 B2 | 10/2003 | Fjield et al. | |
| 6,685,648 B2 | 2/2004 | Flaherty et al. | |
| 6,736,835 B2 | 5/2004 | Pellegrino et al. | |
| 6,845,267 B2 | 1/2005 | Harrison et al. | |
| 6,850,801 B2 | 2/2005 | Kieval et al. | |
| 6,885,888 B2 | 4/2005 | Rezai | |
| 6,893,436 B2 | 5/2005 | Woodard et al. | |
| 6,978,174 B2 | 12/2005 | Gelfand et al. | |
| 7,149,574 B2 | 12/2006 | Yun et al. | |
| 7,162,303 B2 | 1/2007 | Levin et al. | |
| 7,221,979 B2 | 5/2007 | Zhou et al. | |
| 7,381,200 B2 | 6/2008 | Katoh et al. | |
| 7,390,894 B2 | 6/2008 | Weinshilboum et al. | |
| 7,617,005 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,778,703 B2 | 8/2010 | Gross et al. | |
| 8,131,372 B2 | 3/2012 | Levin et al. | |
| 8,140,170 B2 | 3/2012 | Rezai et al. | |
| 8,145,317 B2 | 3/2012 | Demarais et al. | |
| 8,150,518 B2 | 4/2012 | Levin et al. | |
| 8,150,520 B2 | 4/2012 | Demarais et al. | |
| 8,175,711 B2 | 5/2012 | Demarais et al. | |
| 8,347,891 B2 | 1/2013 | Demarais et al. | |
| 8,888,773 B2* | 11/2014 | Chang | A61M 25/0102 606/41 |
| 9,060,755 B2 | 1/2015 | Buckley et al. | |
| 9,084,610 B2* | 7/2015 | Goshgarian | A61B 18/1492 |
| 2003/0060858 A1 | 3/2003 | Kieval et al. | |
| 2005/0209654 A1* | 9/2005 | Boveja | A61N 1/20 607/45 |
| 2005/0228460 A1 | 10/2005 | Levin et al. | |
| 2005/0288730 A1* | 12/2005 | Deem | A61N 1/205 607/42 |
| 2006/0041277 A1* | 2/2006 | Deem | A61N 1/36128 607/3 |
| 2006/0116721 A1* | 6/2006 | Yun | A61P 9/12 607/2 |
| 2006/0206150 A1 | 9/2006 | Demarais et al. | |
| 2006/0271111 A1 | 11/2006 | Demarais et al. | |
| 2007/0060954 A1* | 3/2007 | Cameron | A61N 1/0553 607/2 |
| 2007/0129720 A1 | 6/2007 | Demarais et al. | |
| 2007/0265687 A1 | 11/2007 | Deem et al. | |
| 2008/0255642 A1* | 10/2008 | Zarins | A61B 18/1206 607/99 |
| 2008/0319513 A1 | 12/2008 | Pu et al. | |
| 2009/0036948 A1 | 2/2009 | Levin et al. | |
| 2010/0137860 A1 | 6/2010 | Demarais et al. | |
| 2010/0137952 A1 | 6/2010 | Demarais et al. | |
| 2010/0168739 A1* | 7/2010 | Wu | A61B 18/1492 606/41 |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2011/0208096 A1* | 8/2011 | Demarais | A61N 1/32 601/3 |
| 2011/0245633 A1* | 10/2011 | Goldberg | A61B 5/165 600/301 |
| 2011/0264011 A1* | 10/2011 | Wu | A61B 18/1492 601/2 |
| 2012/0039812 A1* | 2/2012 | Holsboer | C12Q 1/6883 424/9.2 |
| 2012/0116382 A1 | 5/2012 | Ku et al. | |
| 2012/0130289 A1 | 5/2012 | Demarais et al. | |
| 2012/0130345 A1 | 5/2012 | Levin et al. | |
| 2012/0136350 A1* | 5/2012 | Goshgarian | A61B 18/1492 606/41 |
| 2012/0136418 A1* | 5/2012 | Buckley | A61B 18/02 607/105 |
| 2012/0150267 A1 | 6/2012 | Buckley et al. | |
| 2012/0172837 A1 | 6/2012 | Demarais et al. | |
| 2012/0172680 A1* | 7/2012 | Gelfand | A61N 1/06 600/301 |
| 2013/0079835 A1* | 3/2013 | Sluijter | A61N 1/06 607/3 |

(56) References Cited

U.S. PATENT DOCUMENTS

| | | | | |
|---|---|---|---|---|
| 2013/0144251 | A1* | 6/2013 | Sobotka | A61B 18/1492 604/500 |
| 2013/0178910 | A1* | 7/2013 | Azamian | A61B 18/1815 607/33 |
| 2013/0218029 | A1* | 8/2013 | Cholette | A61B 5/4035 600/480 |
| 2013/0282001 | A1* | 10/2013 | Hezi-Yamit | A61N 1/3605 606/33 |
| 2013/0289682 | A1* | 10/2013 | Barman | A61N 1/0558 607/116 |
| 2013/0304061 | A1* | 11/2013 | Chang | A61M 25/0108 606/41 |
| 2014/0255517 | A1* | 9/2014 | Ressler | A61K 31/4178 424/715 |
| 2014/0257438 | A1* | 9/2014 | Simon | A61N 2/02 607/72 |
| 2014/0276718 | A1 | 9/2014 | Turovskiy et al. | |
| 2014/0350327 | A1* | 11/2014 | Poon | A61N 2/004 600/9 |
| 2015/0025297 | A1* | 1/2015 | Pan | A61N 2/004 600/13 |
| 2015/0066007 | A1* | 3/2015 | Srivastava | A61B 5/24 606/21 |
| 2015/0112409 | A1* | 4/2015 | Hagedorn | A61B 5/375 607/62 |
| 2015/0126480 | A1* | 5/2015 | McBride | G01N 33/6869 514/169 |
| 2015/0196242 | A1* | 7/2015 | Lathan | G16H 50/20 434/236 |
| 2015/0257825 | A1* | 9/2015 | Kelly | A61B 18/1492 606/41 |
| 2015/0292014 | A1* | 10/2015 | Zhu | G16C 20/30 506/2 |
| 2015/0327924 | A1* | 11/2015 | Melder | A61B 18/1492 606/41 |
| 2016/0001096 | A1* | 1/2016 | Mishelevich | A61N 7/00 601/2 |
| 2016/0038769 | A1* | 2/2016 | Sullivan | G16H 50/30 601/2 |
| 2016/0045121 | A1* | 2/2016 | Akingba | A61B 5/6877 600/301 |
| 2016/0045740 | A1* | 2/2016 | Rezai | A61N 1/36139 607/45 |
| 2016/0058503 | A1* | 3/2016 | Tunev | A61B 18/1492 606/41 |
| 2016/0106808 | A1* | 4/2016 | Charney | A61K 45/06 424/43 |
| 2016/0128767 | A1* | 5/2016 | Azamian | A61B 18/1492 606/41 |
| 2016/0213313 | A1* | 7/2016 | Toth | A61B 5/4839 |
| 2016/0317621 | A1* | 11/2016 | Bright | A61K 31/19 |
| 2016/0367809 | A1* | 12/2016 | Patel | A61N 5/0622 |
| 2017/0020443 | A1* | 1/2017 | Fein | A61B 5/02405 |
| 2017/0076740 | A1* | 3/2017 | Feast | H04L 67/22 |
| 2017/0095679 | A1* | 4/2017 | Sobotka | A61N 5/045 |
| 2017/0165264 | A1* | 6/2017 | Renshaw | A23L 33/10 |

FOREIGN PATENT DOCUMENTS

| | | |
|---|---|---|
| WO | WO2015113027 | 7/2015 |
| WO | WO2015143372 | 9/2015 |
| WO | WO2016033543 | 3/2016 |

OTHER PUBLICATIONS

Michopoulos et al., "Diagnostic Biomarkers for Posttraumatic Stress Disorder (PTSD): Promising Horizons from Translational Neuroscience Research," Biol Psychiatry. Author Manuscript, Sep. 1, 2015, 78(5):344-353, 21 pages.

Michopoulos et al., "Posttraumatic stress disorder: A metabolic disorder in disguise?" Experimental Neurology (Elsevier), May 2016, vol. 284, pp. 220-229.

Morris et al., "Cortisol, heart rate, and blood pressure as early markers of PTSD risk: A systematic review and meta-analysis," Clinical Psychology Review, Sep. 2016, vol. 49, pp. 79-91.

Mortensen et al., "Catheter-Based Renal Sympathetic Denervation Improves Central Hemodynamics and Arterial Stiffness: A Pilot Study," The Journal of Clinical Hypertension, Dec. 2012, vol. 14(12), pp. 861-870.

Pitman et al., "Biological Studies of Posttraumatic Stress Disorder," Nat Rev Neurosci. Author Manuscript, Nov. 2012, 13(11):769-787, 44 pages.

Rand et al., "Invisible Wounds of War Psychological and Cognitive Injuries, Their Consequences, and Services to Assist Recovery," Rand Corporation, 2008, 499 pages.

Sah et al., "Neuropeptide Y and posttraumatic stress disorder," Mol Psychiatry Author Manuscript, Jun. 2013, 18(6):646-655, 25 pages.

Schlaich et al., "Effects of renal denervation on sympathetic activation, bloodpressure, and glucose metabolism in patients with resistant hypertension," Frontiers in Physiology, Feb. 2012, vol. 3(10), 7 pages.

Sherin et al., "Post-traumatic stress disorder: the neurobiological impact of psychological trauma," State of the art: Dialogues in Clinical Neuroscience, 2011, vol. 13(3), pp. 263-278.

Spijker et al., "Glucocorticoid Sensitivity in Mood Disorders," Neuroendocrinology, 2012, 95:179-186, 8 pages.

Ulmer et al., "Nocturnal Blood Pressure Non-Dipping, Post-traumatic Stress Disorder, and Sleep Quality in Women," Behav Med. Author Manuscript, 2013, 39(4):111-121, 18 pages.

Van Zuiden et al., "Pre-Existing High Glucocorticoid Receptor Number Predicting Development of Posttraumatic Stress Symptoms After Military Deployment," Am J Psychiatry, Jan. 2011, vol. 168, pp. 89-96.

Van Zuiden et al., "A prospective study on personality and the cortisol awakening response to predict posttraumatic stress symptoms in response to military deployment," Journal of Psychiatric Research, 2011, vol. 45, pp. 713-719.

Yahyavi et al., "Relationship of cortisol, norepinephrine, and epinephrine levels with war-induced posttraumatic stress disorder in fathers and their offspring," Revista Brasileira de Psiquiatria, 2015, vol. 37, pp. 93-98.

Yehuda et al., "Glucocorticoid-related predictors and correlates of post-traumatic stress disorder treatment response in combat veterans," Interface Focus, 2014, vol. 4, 10 pages.

Young et al., "Cortisol and Catecholamines in Posttraumatic Stress Disorder an Epidemiologic Community Study," Arch Gen Psychiatry, Apr. 2004, vol. 61, pp. 394-401.

Zaldivia et al., "Renal Denervation Reduces Monocyte Activation and Monocyte-Platelet Aggregate Formation an Anti-Inflammatory Effect Relevant for Cardiovascular Risk," Hypertension, Feb. 2017, pp. 323-331.

Zuern et al., "Effects of renal sympathetic denervation on 24-hour blood pressure variability," Frontiers in Physiology, May 2012, vol. 3(134), 8 pages.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

(56) References Cited

OTHER PUBLICATIONS

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Baroni et al., "Effects of Renal Sympathetic Denervation on Arterial Stiffness and Blood Pressure Control in Resistant Hypertensive Patients: A Single Centre Prospective Study." High Blood Press Cardiovasc. Prev., Dec. 2015, 22(4), pp. 411-416.
Bech et al., "Psychometric evaluation of the Major Depression Inventory (MDI) as depression severity scale using the LEAD (Longitudinal Expert Assessment of All Data) as index of validity," BMC Psychiatry, 2015, vol. 15(190), 7 pages.
Boscarino et al., "The New York PTSD Risk Score for Assessment of Psychological Trauma: Male and Female Versions," Psychiatry Res., Dec. 30, 2012, 200(2-3): 827-834, 18 pages.
Brandt et al., "Effects of Renal Sympathetic Denervation on Arterial Stiffness and Central Hemodynamics in Patients With Resistant Hypertension," Journal of the American College of Cardiology, Nov. 2012, vol. 60, No. 19, pp. 1956-1965.
Bremner et al., "Stress and Brain Atrophy," CNS Neurol. Disord. Drug Targets, Oct. 2006, 5(5): 503-512, 20 pages.
Busso e al., "Media Exposure and Sympathetic Nervous System Reactivity Predict PTSD Symptoms After the Boston Marathon Bombings," Depress Anxiety Author Manuscript, Jul. 2014, 31(7): 551-558, 17 pages.
De Moraes Costa, "Letters to the Editors: New insights into cortisol levels in PTSD," Revista Brasileira de Psiquiatria, 2016, 38:176, doi:10.1590/1516-4446-2015-1795.
Dedert et al.,"Posttraumatic Stress Disorder, Cardiovascular and Metabolic Disease: A Review of the Evidence," Ann. Behav. Med. Author manuscript, Feb. 2010; 39(1): 61-78, 28 pages.
Delahanty, "Toward the Predeployment Detection of Risk for PTSD," Am. J. Psychiatry, Jan. 2011, 168:1, pp. 9-11.
Dorr et al.,"Beneficial effects of renal sympathetic denervation on cardiovascular inflammation and remodeling in essential hypertension," Clinical Research in Cardiology (Springer), 2015, vol. 104, pp. 175-184.
Edmondson et al., "Posttraumatic Stress Disorder and Cardiovascular Disease," Prog Cardiovasc Dis. Author Manuscript, 2013, 55(6): 548-556, 14 pages.
Granado et al., "Newly Reported Hypertension After Military Combat Deployment in a Large Population-Based Study," Hypertension, Nov. 2009, vol. 54, pp. 966-973.
Jedema et al., "Corticotropin-Releasing Hormone Directly Activates Noradrenergic Neurons of the Locus Ceruleus Recorded In Vitro," The Journal of Neuroscience, Oct. 27, 2004, vol. 24(43), pp. 9703-9713.
Kario et al., "Effect of Catheter-Based Renal Denervation on Morning and Nocturnal Blood Pressure Insights From Symplicity HTN-3 and Symplicity HTN-Japan," Hypertension, Dec. 2015, vol. 66, 13 pages.
Lambert et al., "Cognitive performance in patients with resistant hypertension following renal sympathetic denervation," EuroIntervention, Oct. 2013, 9:665-667.
Lambert et al., "Health-related quality of life and blood pressure 12months after renal denervation," Journal of Hypertension, Aug. 2015, vol. 33(11), pp. 2350-2358.
Lenski et al., "Anxiety, depression, quality of life and stress in patients with resistant hypertension before and after catheter-based renal sympathetic denervation," EuroIntervention, 2013, 9:700-708.
Liu et al., "A Risk Score for Predicting Post-Traumatic Stress Disorder in Adults in a Chinese Earthquake Area," The Journal of International Medical Research, 2012, vol. 40, pp. 2191-2198.
Mahan et al., "Fear conditioning, synaptic plasticity and the amygdala: implications for posttraumatic stress disorder," Trends in Neurosciences, Jan. 2012, vol. 35(1), pp. 24-35.
McCall et al., "CRH engagement of the locus coeruleus noradrenergic system mediates stress-induced anxiety," Neuron Author Manuscript, Aug. 5, 2015, 87(3):605-620, 27 pages.
Mark R. de Jong et al. "Renal Nerve Stimulation-Induced Blood Pressure Changes Predict Ambulatory Blood Pressure Response After Renal Denervation" Mar. 9, 2016, Hypertension 2016; 68:707-714.

* cited by examiner

*Arterial Vasculature*

*Venous Vasculature*

Renal Denervation Preclinical Efficacy:
Review of 66 Treated and 64 Naïve Swine

| Group<br>N=Arteries or<br>kidneys | % Non-<br>functional<br>Area | Cortical Axon<br>Area per mm² | Mean NE<br>(pg/mg) |
|---|---|---|---|
| Naïve<br>7 day<br>N=64 | 14.6 ± 8.0 | 207.2 ± 134.6 | 264.8 ± 82.9 |
| Symplicity 7 day<br>N=54 | 56.9 ± 28.3 | 66.8 ± 84.6<br>(68% Decrease) | 92.7 ± 92.7<br>(65% Decrease) |
| Spyral 7 Day<br>N=12 | 47.3 ± 26.5 | 97.4 ± 73.1<br>(54% Decrease) | 88 ± 75<br>(68% Decrease) |

FIG. 9A

| MEN Instructions: Complete Response Boxes: y=yes; n=no | | |
|---|---|---|
| | Response (y/n) | Score |
| Primary Care PTSD Screener (PCPS) | | |
| 1. You had repeated bad dreams or nightmares or had disturbing or unpleasant memories, thoughts, or images that kept coming into your mind whether you wanted to think of them or not. | y | 100 |
| 2. You deliberately tried hard not to think about something that happened to you or went out of your way to avoid certain places or activities that might remind you of something that happened in the past. | y | |
| 3. You felt you had to stay on guard much of the time or unexpected noises startled you more than usual. | y | |
| 4. You felt cut off from other people, found it difficult to feel close to other people, or you could not feel things anymore or you had much less emotion than you used to have. | n | |
| Depression Symptoms (lifetime) | | |
| 1. Have you ever had a period of two weeks or longer when you were feeling depressed or down most of the day or nearly everyday? | y | 83 |
| 2. Have you ever had a period of two weeks or longer when you were uninterested in most things or unable to enjoy things you used to do? | y | |
| Trauma Exposure (lifetime) | | |
| How many traumatic life events do you think you have ever experienced? These are events outside of everyday experiences and include being in combat or a war zone, being assaulted or sexually attacked, being in a major disaster, fire, or accident, experience the sudden and unexpected death of a loved one, and things like these. | 2 | 20 |
| Would you say you never experienced these events, experienced these events _once_, you experienced these events _twice_, experienced these events _three times_ or you experienced these events _four times or more_ in your lifetime? _(Enter the number of events up to 4)_ | | |
| Sleep Disturbance (past 12 months) | | |
| You had difficulty falling asleep or staying asleep? | y | 64 |
| Source of Healthcare/Regular Doctor | | |
| Do you have a regular doctor or a usual source of care that you can go to for routine medical care? | y | 0 |
| | Total | 267 |
| | Score>184→PTSD | |
| SNS Tests | | |
| SDNN (Standard Deviation NN intervals) < 50 ms | y | |
| Baroreceptor Sensitivity (BRS)< 1.74 ms/mmHg | y | RDN Candidate |
| Heart Rate increase > 10 bpm during Stroop Color Test | n | |
| Heart Rate increase > 10 bpm or Systolic Blood Pressure increase > 10 mmHg during Stroop Color Test | n | |
| Heart Rate increase > 10 bpm or Systolic Blood Pressure increase > 10 mmHg during Cold Pressor Test | n | |
| Muscle Sympathetic Nerve Activity > 25 bursts/min | n | |

FIG. 10

| WOMEN Instructions: Complete Response Boxes: y=yes; n=no | | |
|---|---|---|
| | Response (y/n) | Score |
| Primary Care PTSD Screener (PCPS) | | |
| 1. You had repeated bad dreams or nightmares or had disturbing or unpleasant memories, thoughts, or images that kept coming into your mind whether you wanted to think of them or not. | y | 100 |
| 2. You deliberately tried hard not to think about something that happened to you or went out of your way to avoid certain places or activities that might remind you of something that happened in the past. | y | |
| 3. You felt you had to stay on guard much of the time or unexpected noises startled you more than usual. | y | |
| 4. You felt cut off from other people, found it difficult to feel close to other people, or you could not feel things anymore or you had much less emotion than you used to have. | n | |
| Depression Symptoms (lifetime) | | |
| 1. Have you ever had a period of two weeks or longer when you were feeling depressed or down most of the day or nearly everyday? | n | 0 |
| 2. Have you ever had a period of two weeks or longer when you were uninterested in most things or unable to enjoy things you used to do? | n | |
| Trauma Exposure (lifetime) | | |
| How many traumatic life events do you think you have ever experienced? These are events outside of everyday experiences and include being in combat or a war zone, being assaulted or sexually attacked, being in a major disaster, fire, or accident, experience the sudden and unexpected death of a loved one, and things like these. | 3 | 29 |
| Would you say you never experienced these events, experienced these events _once_, you experienced these events _twice_, experienced these events _three times_ or you experienced these events _four times or more_ in your lifetime? _(Enter the number of events up to 4)_ | | |
| Sleep Disturbance (past 12 months) | | |
| You had difficulty falling asleep or staying asleep? | y | 39 |
| Source of Healthcare/Regular Doctor | | |
| Do you have a regular doctor or a usual source of care that you can go to for routine medical care? | y | 0 |
| | Total | 168 |
| | Score > 139 → PTSD | |
| Office Systolic Blood Pressure (mmHg) | 120 | |

RDN Candidate

FIG. 11

METHODS FOR TREATING POST-TRAUMATIC STRESS DISORDER IN PATIENTS VIA RENAL NEUROMODULATION

CROSS-REFERENCE TO RELATED APPLICATION(S)

The present application claims priority to U.S. Provisional Patent Application No. 62/528,867, filed Jul. 5, 2017, and to U.S. Provisional Patent Application No. 62/570,597, filed Oct. 10, 2017, both of which are incorporated herein by reference in their entireties.

TECHNICAL FIELD

The present technology relates generally to apparatuses, systems, and methods for treating post-traumatic stress disorder (PTSD) and/or for reducing a risk associated with developing PTSD in patients via renal neuromodulation.

BACKGROUND

PTSD is a mental condition that can develop in some people after experiencing or witnessing a traumatic and/or life-threatening event causing intense feelings of fear, helplessness, or horror in the individual. Traumatic events involving warfare, sexual assault, natural disasters, a car accident, or a sudden death of a loved one, for example, can cause natural feelings of fear, which may trigger physiological body changes to help a person defend against or avoid danger. Such "fight-or-flight" responses are natural reactions and, in some situations, can affect a person for a short time (e.g., days or a few weeks) after the traumatic event. In situations where initial symptoms do not dissipate naturally, a traumatized person may develop ongoing (chronic) or short-term (acute) PTSD with potential for debilitating mental and physical health outcomes. Identifiable and clinical symptoms of PTSD may include reliving or re-experiencing the traumatic experience in flashbacks or through nightmares, experiencing mental or physical distress to thoughts or trauma-related reminders, changes in cognitive ability, increased arousal (e.g., increased startle response), negative feelings about self or the world, and/or thoughts of suicide.

The American Psychiatric Association estimates that, in the United States, 3.5% of adults have PTSD in a given year with 9% of people developing it at some point in their life. While certain individuals pose a greater risk for developing PTSD, anyone can develop PTSD at any age. For example, people who have experienced previous traumatic events or those that have been exposed to violence (e.g., an assault-based traumatic event) run a higher risk of developing PTSD. Particularly, deployed military service members have a higher rate of PTSD (e.g., 11%-20% in a given year, up to 30% in their lifetime) than non-deployed military members or civilians (U.S. Department of Veterans Affairs). Moreover, women are more than twice as likely as men to be diagnosed with PTSD at some point during their lifetime.

PTSD is typically treated with a combination of medication (e.g., antidepressants) and psychotherapy. As PTSD can have severe psychological, physical, social and economic impact on patients as well as families and society, there is a need for treatments that effectively treat and/or manage PTSD, including the severity of symptoms associated with PTSD. Furthermore, there is a need for treatments that effectively reduce the incidence of PTSD, or provide other improvements in prognosis and outcomes for patients at risk of developing PTSD following a traumatic event.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 9A is a display table illustrating results from a study to determine the effects of renal denervation on cortical axon density and mean norepinephrine concentration in animal subjects.

FIG. 10 illustrates a PTSD risk calculator for determining a male patient's PTSD risk score in accordance with an embodiment of the present technology.

FIG. 11 illustrates a PTSD risk calculator for determining a female patient's PTSD risk score in accordance with an embodiment of the present technology.

DETAILED DESCRIPTION

Figure 1:
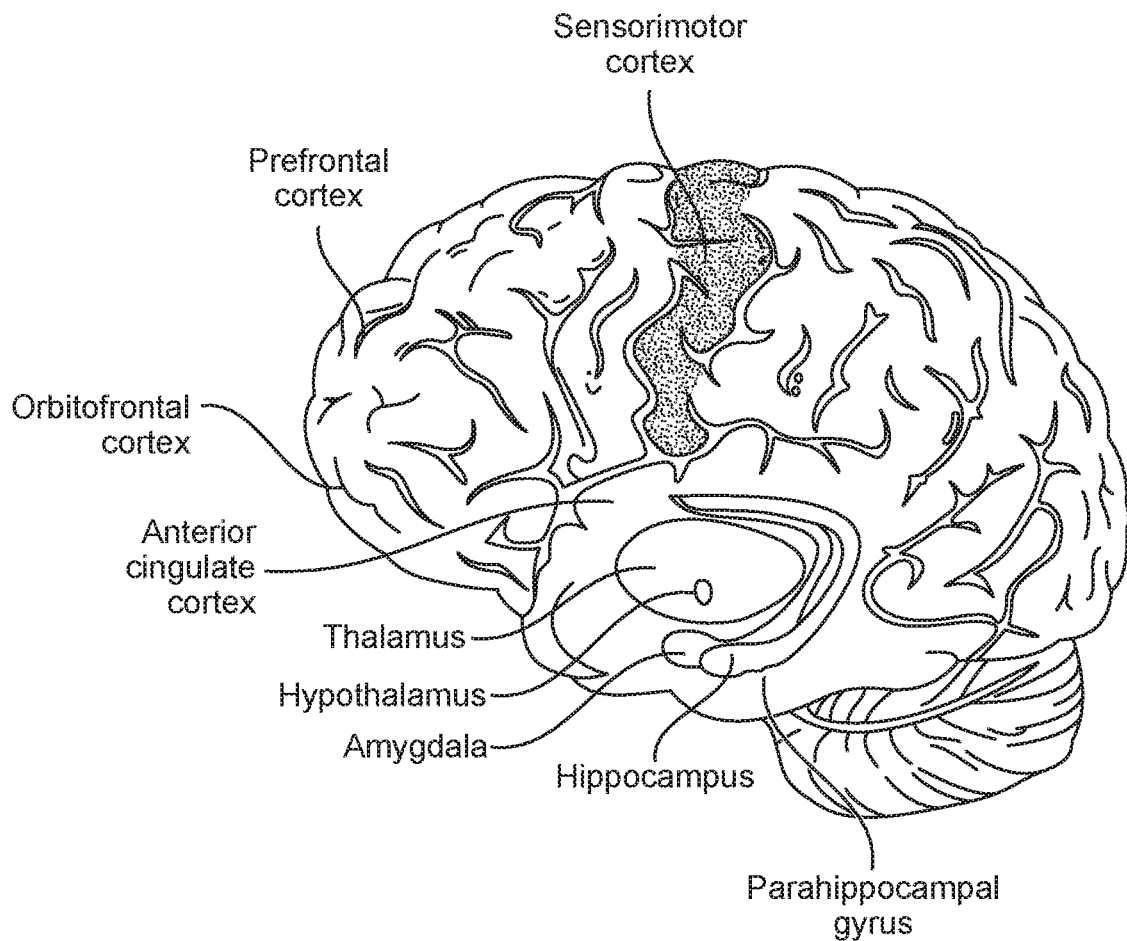
FIG. 1 is a schematic illustration of the human brain illustrating the neural structures of the limbic system involved in PTSD.

The present technology is directed to methods for treating PTSD, managing symptoms or sequelae associated with PTSD, reducing a severity of PTSD and/or for reducing a risk associated with developing PTSD in patients following a traumatic event via renal neuromodulation. In certain embodiments, the present technology is directed to improving one or more measurable physiological parameters associated with PTSD in a patient via renal neuromodulation. Other embodiments of the present technology include performing therapeutically-effective renal neuromodulation on a patient to reduce a severity of neurobiological symptoms relating to PTSD. Further embodiments of the present technology include performing therapeutically-effective renal neuromodulation on a patient to reduce the risk of occurrence of PTSD in patients at risk of developing PTSD following a traumatic event.

In a particular embodiment, for example, the patient has experienced a life-threatening and/or otherwise traumatic event that poses a measurable risk of developing PTSD, but the patient does not currently meet the standard for a PTSD diagnosis. In some embodiments, the patient exhibits one or more additional risk factors for the development of PTSD following a traumatic event. Other embodiments of the present technology include performing therapeutically-effective renal neuromodulation on a patient prior to the patient experiencing a potentially traumatic event. For example, the patient may be a member of the armed forces that is going to be deployed to a combat zone.

As discussed in greater detail below, therapeutically-effective renal neuromodulation can include rendering neural fibers inert, inactive, or otherwise completely or partially reduced in function. This result can be electrically-induced, thermally-induced, or induced by another mechanism during a renal neuromodulation procedure, e.g., a procedure including percutaneous transluminal intravascular access.

Specific details of several embodiments of the technology are described below with reference to FIGS. 1-11. The embodiments can include, for example, modulating nerves proximate (e.g., at or near) a renal artery, a renal vein, and/or other suitable structures. Although many of the embodiments are described herein with respect to electrically-induced, thermally-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-11.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. PTSD

Psychological trauma incurred from experiencing or witnessing an event that is perceived to be life-threatening or to pose potential or serious bodily harm or injury can manifest in a chronic and/or debilitating manner as PTSD. While a normal response to such a trauma tends to be limited to a transient disturbance (e.g., less than a month), individuals that continue to endure a plurality of well-characterized trauma-related symptoms and manifestations beyond one month following the traumatizing event, may be diagnosed with PTSD.

For a clinically-accepted diagnosis of PTSD, the American Psychiatric Association defines the criteria in its *Diagnostic and Statistical Manual of Mental Disorders* (DSM-5). The first criterion is an exposure to at least one event defined by death, threatened death, actual or threatened serious injury, or actual or threatened sexual violence. The exposure can be direct or as a witness to the trauma. In further scenarios, the exposure could be through learning that a relative or close friend was exposed to a trauma, or through indirect exposure to aversive details (e.g., first responders, medics, other trauma-associated professionals, etc.).

Following the traumatic exposure (first criterion), symptoms of PTSD, grouped generally into four categories, are required (second through fifth criteria outlined by the DSM-5): reminders of the trauma exposure, avoidance of trauma-related cues, hyperarousal, and negative cognition and mood. For example, a clinical diagnosis of PTSD (according to the DSM-5) requires patients to report at least one re-experiencing symptom (second criterion), which could include, for example, flashbacks of the trauma, nightmares relating to the event, or frightening and/or intrusive thoughts associated with the trauma. During or after re-experiencing episodes or traumatic reminders, the patient can report emotional distress and/or physical reactivity (e.g., elevated heart rate, sweating, etc.). The diagnosis further requires at least one avoidance symptom (third criterion), which can be a conscience or unconscious avoidance of places, events or objects that are reminders of the event, avoiding thoughts or feelings relating to the event, etc. The fourth criterion includes at least two cognition and mood symptoms such as feelings of guilt or blame, negative thoughts about oneself, trouble remembering key features of the traumatic event, and/or decreased interest in activities. The fifth criterion requires at least two arousal and reactivity symptoms, such as irritability or aggression, risky or destructive behavior, hypervigilance, heightened startle reaction, difficulty concentrating, difficulty sleeping, and/or angry outbursts.

Patients whose symptoms persist for a few weeks and then resolve are diagnosed with acute stress disorder. For a diagnosis of PTSD, the symptoms must last for greater than one month (although full diagnostic criteria are not usually met until at least six months after the trauma exposure), create distress of functional impairment for the patient (e.g., social or relationship impairment, occupational impairment, etc.), and cannot be due to medication, substance use or other illness. The DSM-5 further clarifies that patients with PTSD will typically experience high levels of dissociative behavior, such as depersonalization (e.g., experience of being an outside observer or detached from oneself, feeling like in a dream-state) and/or derealization (e.g., experience of unreality, distance or distortion, feeling of "things are not real", etc.).

Clinicians and other mental health practitioners typically use conventionally accepted diagnostic test methods, such as screening tools (e.g., for use during diagnostic interviews, patient health questionnaires, etc.) for identifying PTSD risk, severity, and diagnosis. Typically, these screening tools are focused on core PTSD symptoms and, although relatively short, they have been shown to have reasonable specificity and sensitivity for identifying PTSD patients among military and civilian populations (Boscarino, J. A., et al., *Psychiatry Res.*, 2012, 200: 827-834). For example, patients can be diagnosed with PTSD using the Primary Care PTSD Screener (PCPS), the Short Screening Scale for PTSD (SSSP), the abbreviated PTSD Checklist (APCL), and the Short PTSD Rating Interview (SPRINT), among others (Id.). Other screening instruments, such as the New York PTSD Risk Score (NYPRS), look at multiple risk factors beyond the conventional screening tools to provide a risk score for predicting PTSD status among at-risk populations and taking into account differences among gender and other experiences (Id.).

As used herein, "PTSD" refers to any form of chronic or persistent stress disorder following a qualifying traumatic exposure or event as described herein or as described in the DSM-5, and in which meets the additional criteria set forth in DSM-5 and/or in which one or more PTSD screening tools or instruments are used to give a professionally-accepted diagnosis.

As discussed above, not everyone that survives a dangerous or traumatic event will develop PTSD; however, certain risk factors have been identified that may make an individual more likely (e.g., increase a risk) to develop PTSD following a traumatic experience. For example, some identified risk factors for increasing a likelihood of developing PTSD include having suffered an injury or being wounded during the traumatic event, being under 25 years old (e.g., for military deployment), having a traumatic brain injury, having experienced prior traumatic events, being a childhood survivor of abuse, experiencing trauma during childhood, having little or no social support following the traumatic event, having a history of mental illness or substance abuse, losing a close family member during or shortly after the traumatic exposure, divorced or widowed marital status and female gender among others (Boscarino, J. A., et al., *Psychiatry Res.*, 2012, 200: 827-834; Liu, X., et al., *J Int Med Res*, 2012, 40: 2191-2198; Sherin, J. E., et al., *Dialogues Clin Neurosci*, 2011, 13: 263-278).

PTSD patients may also experience other adverse mental and physical diseases and disorders. For example, PTSD has high comorbidity with mental disorders such as major depressive disorder, substance and alcohol abuse, panic disorder, and suicidal tendencies (Michopoulos, V., et al., *Exp Neurol*, 2016, 284: 220-229). Further, cardiovascular disease, hypertension, obesity (e.g., high body mass index (BMI)) and metabolic disorders, such as type 2 diabetes, are also highly comorbid with PTSD (Id.). Without being bound by theory, it is possible that PTSD shares underlying neuroendocrine, metabolic and other psychophysiological patterns with these other disorders that either increase risk for PTSD development or reduce treatment success.

A. Biophysical Characteristics of Individuals with PTSD

Though initiated or triggered by a traumatic event, the underlying neurobiological and metabolic mechanisms or etiology of PTSD are uncertain. For example, while it is uncertain why some individuals develop PTSD following a traumatic event and other individuals do not, evidence suggests that psychological, genomic, and other biological risk factors are present in patients identified with PTSD. Moreover, neurobiological heterogeneity in monoaminergic transmitter systems, the hypothalamic-pituitary-adrenal (HPA) axis, metabolic hormonal pathways, inflammatory mechanisms, and psychophysiological reactive and neural circuits have been demonstrated between individuals diagnosed with PTSD and healthy individuals (Michopoulos, V., et al., *Biol Psychiatry*, 2015, 78(5): 344-353; Young, E. A, et. al., *Arch Gen Psychiat*, 2004, 61: 394-401).

In addition to differences between individuals diagnosed with PTSD and those exposed to trauma that do not develop the disorder, those who meet the criteria for PTSD can vary in the severity of their symptoms as well as the type of symptoms they experience. PTSD is a fear regulation disorder in which learned fear (e.g., due to a traumatic event, predisposed by earlier traumatic events, etc.) becomes generalized to situations that would normally be safe, and results in hyperarousal in unnecessary situations (Mahan, A. L. and Ressler, K. J., *Trends Neurosci*, 2012, 35: 24-35). Fear conditioning, stress responses, and related emotional and cognitive learning and memory are regulated by portions of the limbic system, which are key structures within the brain that are altered in PTSD patients.

FIG. 1 is a schematic illustration of the human brain illustrating the neural structures of the limbic system involved in PTSD. The amygdala, the hippocampus and the prefrontal cortex have demonstrable importance for conditioned fear and associative emotional learning that is dysregulated in PTSD resulting in increased stress sensitivity, generalized fear responses and impaired fear extinction (i.e., wherein a conditioned stimulus is repeatedly presented in the absence of the unconditioned stimulus such that the conditioned fear response is diminished). The amygdala is important for healthy conditioned fear (e.g., a fear response elicited by a conditioned stimulus/cue) and associative emotional learning (e.g., memory of emotional events). Compared to healthy individuals, PTSD patients show greater amygdala activation in response to trauma-related stimuli or reminders (Pitman, R. K., et al., *Nat Rev Neurosci.*, 2012, 13: 769-787; Mahan, A. L. and Ressler, K. J., *Trends Neurosci*, 2012, 35: 24-35). Referring to FIG. 1, the amygdala receives neural projections from both the hippocampus and the prefrontal cortex. The hippocampus is involved in encoding episodic memories and environmental cues as well as mediating learned responses to such contextual cues. The prefrontal cortex is thought to involve reactivation of past emotional associations as well as executive functions/decision making. Functional neuroimaging studies have reported reduced activation of both of these neural structures in PTSD patients when compared to healthy subjects, and structural magnetic resonance imaging (sMRI) demonstrates reduced hippocampal and ventromedial prefrontal cortex volumes which is similar to atrophy seen in subjects with chronic stress (Id.). Without being bound by theory, the prefrontal cortex may fail to inhibit the amygdala in PTSD patients, thereby disposing the patient toward increased fear responses, reduced fear extinction of traumatic memories, impaired emotional responses and reduced cognitive abilities (Id.). Additional regions of the brain that play a role in fear conditioning and/or demonstrate altered structure and/or regulation in PTSD include the parahippocampal gyms, orbitofrontal cortex, sensorimotor cortex, thalamus, anterior cingulate cortex, and the insular cortex (not shown) (Id.).

Traumatic stress, like chronic stress, can have deleterious effects on the brain's neural circuits as well as whole-body physiological states. The neuro-hormonal systems that play a critical role in stress responses and homeostasis include the HPA axis and noradrenergic systems. The noradrenergic system includes a dense network of axons that extend from the locus coeruleus in the brain stem throughout the brain including the hippocampus, amygdala, thalamus and hypothalamus, as well as projections that extend down the brain stem to synapse with sympathetic nerve fibers in the thoracic region.

Figure 2:
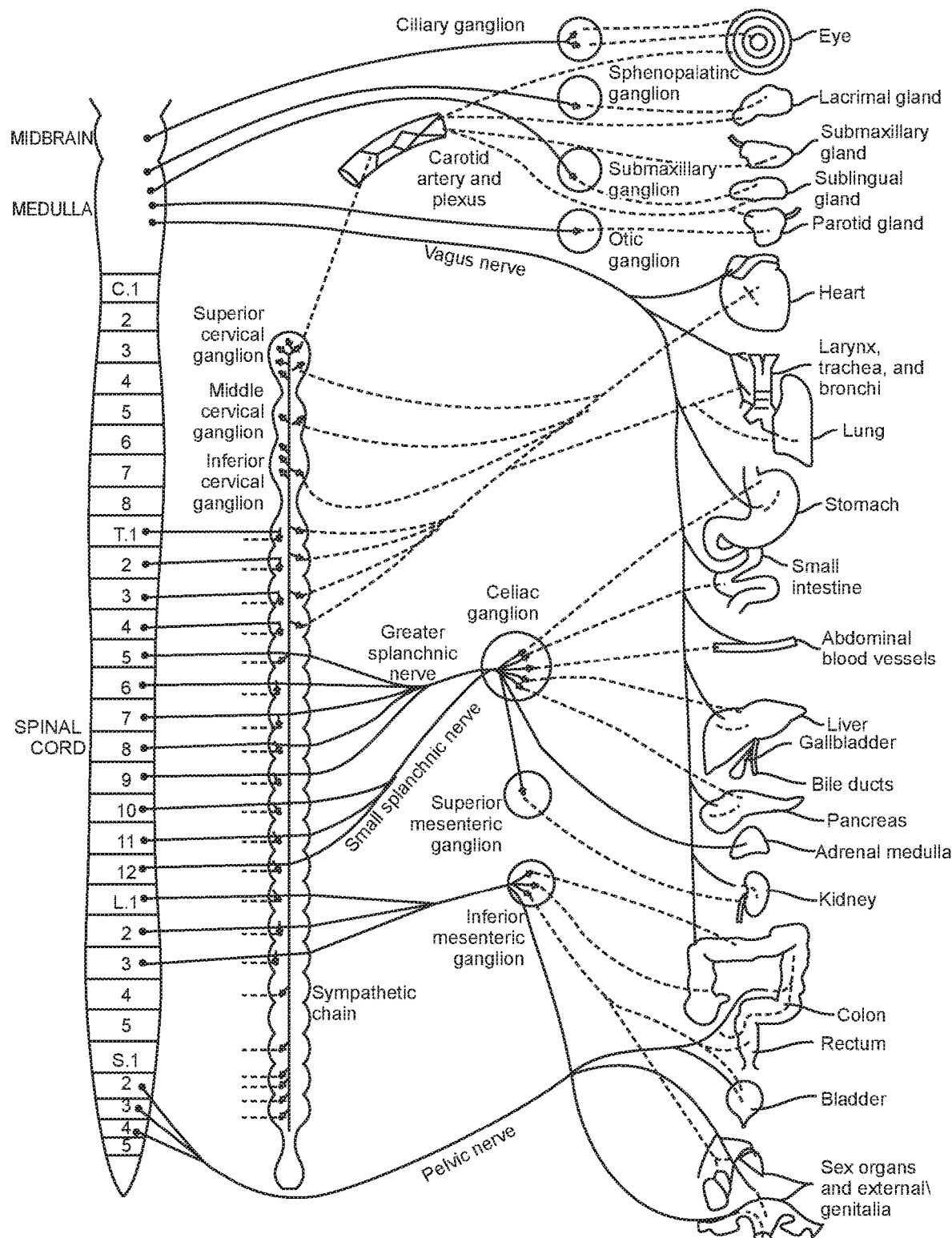
FIG. 2 is a conceptual illustration of the sympathetic nervous system (SNS) and how the brain communicates with the body via the SNS.

Correlative links have been established between PTSD and chronic or prolonged hyperactivity of the sympathetic branch of the autonomic nervous system (Sherin, J. E., et al., *Dialogues Clin Neurosci*, 2011, 13: 263-278; Michopoulos, V., et al., *Biol Psychiatry*, 2015, 78(5): 344-353; Morris, M. C., et al., *Clin Psychol Rev*, 2016, 49:79-91). As shown in FIG. 2, the SNS is a branch of the autonomic nervous system along with the enteric nervous system and parasympathetic nervous system. The SNS is primarily an involuntary bodily control system typically associated with stress responses. It is always active at a basal level (called sympathetic tone) and becomes more active during times of stress. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. The SNS regulates the function of virtually all human organ systems by localized release of catecholamines (e.g., norepinephrine) from sympathetic nerve terminals innervating these tissue and organ systems, spillover of norepinephrine from vascular neuro-muscular junctions (the primary source of norepinephrine in plasma), and by systemic circulation of catecholamines (e.g., epinephrine, norepinephrine) released from the adrenal gland in response to acute, transient stress or threats. Long-term variations in basal levels, increases in basal levels due to aging, as well as spikes of circulating catecholamines from hyperactivity of the SNS responding to life circumstances can also exert more enduring regulatory effects on gene expression by altering constitutive gene expression profiles in a wide variety of tissues and organ systems.

Once released, norepinephrine binds adrenergic receptors on peripheral tissues. In addition, activation (e.g., norepinephrine release) of noradrenergic nuclei in the central nervous system (CNS) can result from transmitted impulses from activated afferent renal sympathetic neurons. Binding to adrenergic receptors either in the periphery or in the CNS causes a neuronal and hormonal response. The physiologic manifestations include pupil dilation, increased heart rate, occasional vomiting, and increased blood pressure. Increased sweating is also seen due to binding of cholinergic receptors of the sweat glands. It is known that long-term SNS hyperactivity has been identified as a major contributor to the complex pathophysiology of hypertension, states of volume overload (such as heart failure), and progressive renal disease, both experimentally and in humans. Moreover, correlative links between activation of the SNS and systemic inflammation, arterial stiffness, atherosclerosis, metabolic disorders, insulin resistance, and other cardiovascular conditions have been established. As mentioned above, many of these conditions are comorbid with PTSD.

Increased SNS tone with demonstrated increased levels of catecholamine (e.g., norepinephrine) spillover and secretion are associated with PTSD diagnosis. For example, increased levels of catecholamines (e.g., norepinephrine) and their metabolites (e.g., vanillylmandelic acid) excreted in urine have been documented in combat veterans, abused women and abused children diagnosed with PTSD (Sherin, J. E., et al., *Dialogues Clin Neurosci*, 2011, 13: 263-278). Further, higher levels of circulating catecholamines, such as norepinephrine (in the periphery and central nervous systems), have been reported in anxiety disorders including PTSD; and an activated noradrenergic system is implicated in arousal disturbance, which is one of the characterizing symptoms of PTSD (Young, E. A, et. al., *Arch Gen Psychiat*, 2004, 61: 394-401; Michopoulos, V., et al., *Exp Neurol*, 2016, 284: 220-229; Michopoulos, V., et al., *Biol Psychiatry*, 2015, 78(5): 344-353). Other indicators of increased SNS tone in PTSD patients include elevations in heart rate, blood pressure, and skin conductance, as well as a decrease in heart rate variability (e.g., a measure of beat-to-beat fluctuations in heart rate) (Sherin, J. E., et al., *Dialogues Clin Neurosci*, 2011, 13: 263-278; Morris, M. C., et al., *Clin Psychol Rev*, 2016, 49:79-91; Michopoulos, V., et al., *Exp Neurol*, 2016, 284: 220-229). In contrast, individuals that have been exposed to trauma but did not subsequently develop PTSD, as well as individuals that have not been exposed to such trauma, all exhibit significantly lower urine catecholamine levels and do not display other indicators of elevated SNS activity (Young, E. A, et. al., *Arch Gen Psychiat*, 2004, 61: 394-401).

Without being bound by theory, increased levels of norepinephrine can account for many aspects of PTSD symptoms, including increased coding of fear memories, hyperarousal, sleep disturbances, and heightened startle responses (Sherin, J. E., et al., *Dialogues Clin Neurosci*, 2011, 13: 263-278; Michopoulos, V., et al., *Exp Neurol*, 2016, 284: 220-229; Sah, R. and Geracioti, T. D., *Mol Psychiatry*, 2013, 18:646-655). Hyperactive SNS activity in patients with PTSD also presents an on-going challenge to treatment success as levels of norepinephrine increase or spike in response to stressors and/or new threat exposures (real or imagined) in these individuals (Michopoulos, V., et al., *Exp Neurol*, 2016, 284: 220-229; Michopoulos, V., et al., *Biol Psychiatry*, 2015, 78(5): 344-353). Peripheral $\alpha$2-adrenergic receptors, which block norepinephrine activity by inhibiting pre-synaptic norepinephrine release, are attenuated in individuals with PTSD, further exacerbating stress responses (Sherin, J. E., et al., *Dialogues Clin Neurosci*, 2011, 13: 263-278; Michopoulos, V., et al., *Exp Neurol*, 2016, 284: 220-229; Michopoulos, V., et al., *Biol Psychiatry*, 2015, 78(5): 344-353).

Individuals with PTSD also exhibit altered HPA axis function as evidenced by elevated peripheral and central levels of corticotropin-releasing hormone (CRH), which initiates stimulation of the HPA axis in response to stress (Michopoulos, V., et al., *Exp Neurol*, 2016, 284: 220-229). Enhanced glucocorticoid negative feedback and lower circulating cortisol (i.e., glucocorticoid) levels compared to non-traumatized controls also exemplify HPA axis dysfunction in PTSD patients (Morris, M. C., et al., *Clin Psychol Rev*, 2016, 49:79-91). In particular, it has been demonstrated that PTSD patients exhibit elevated glucocorticoid receptor levels on leukocytes (e.g., lymphocytes), enhanced glucocorticoid sensitivity, and decreased levels of FKBP5, which is a co-chaperone of the glucocorticoid receptor that inhibits ligand binding and pathway activation (Michopoulos, V., et al., *Exp Neurol*, 2016, 284: 220-229; Michopoulos, V., et al., *Biol Psychiatry*, 2015, 78(5): 344-353). This additional major stress response system may determine longer-term patterns of stress responses via the hormonal cascade that results in the release of cortisol from the adrenal cortex (Morris, M. C., et al., *Clin Psychol Rev*, 2016, 49:79-91).

CRH and norepinephrine are known to interact in regions of the brain involved in stress responses to increase fear conditioning and encoding of emotional memories and enhanced arousal (Sherin, J. E., et al., *Dialogues Clin Neurosci*, 2011, 13: 263-278). This integration of endocrine and autonomic responses to stress can be inhibited by glucocorticoids; however, as discussed above, individuals with PTSD exhibit lower circulating levels of cortisol (e.g., as a result of HPA axis dysregulation). Further reinforcing a prolonged stress response and the pathophysiology of PTSD, CRH has been shown to activate neurons in the locus coeruleus resulting in increased norepinephrine levels throughout the CNS (Jedema, H. P. and Grace, A. A., *J Neurosci*, 2004, 24:9703-9713).

Dopamine is another catecholamine that exhibits increased levels of urinary excretion (along with levels of its metabolite) in patients with PTSD. The reward pathway in the brain (i.e., the mesolimbic dopaminergic pathway) has been implicated in fear conditioning and some evidence suggests that exposure to environmental stressors releases mesolimbic dopamine, which could further modulate HPA axis responses (Sherin, J. E., et al., *Dialogues Clin Neurosci*, 2011, 13: 263-278).

Neuropeptide Y (NPY), a 36-amino-acid peptide transmitter that is expressed in brain regions that regulate stress and emotional behaviors, has shown to buffer stress responses and promote increased ability to cope with emotional trauma (Sah, R. and Geracioti, T. D., *Mol Psychiatry*, 2013, 18:646-655; Sherin, J. E., et al., *Dialogues Clin Neurosci*, 2011, 13: 263-278). In particular, central nervous system NPY concentration levels may normally control or suppress pro-stress transmitters such as CRH and norepinephrine in the brain (Id.). However, central nervous system NPY concentrations are significantly lower in individuals with combat-related PTSD when compared to healthy controls (Sah, R. and Geracioti, T. D., *Mol Psychiatry*, 2013, 18:646-655), possibly attenuating the individuals' resilience and coping ability following a traumatizing event. Since NPY functions to inhibit CRH and norepinephrine promotion of stress and fear responses, as well as reduces the release of norepinephrine from sympathetic neurons, decreased NPY activity may contribute to SNS hyperactivity in PTSD patients (Sherin, J. E., et al., *Dialogues Clin Neurosci*, 2011, 13: 263-278).

An additional physiological characteristic associated with PTSD includes a pro-inflammatory state, including chronic inflammation (Michopoulos, V., et al., *Exp Neurol*, 2016, 284: 220-229; Michopoulos, V., et al., *Biol Psychiatry*, 2015, 78(5): 344-353). For example, elevated levels of inflammatory cytokines, such as interleukin-6 (IL-6), IL-1$\beta$, and IL-2, as well as other inflammatory markers, such as C-reactive protein (CRP) are elevated in individuals with PTSD, and peripheral levels of these inflammatory markers correlate positively with PTSD symptomology (Id.). Moreover, CRP levels are associated with exacerbated PTSD symptoms as well as an increased risk in the development of PTSD in traumatized individuals (Michopoulos, V., et al., *Exp Neurol*, 2016, 284: 220-229). PTSD is also associated with increased activation of the transcriptional factor, nuclear factor-$\kappa$B (NF-$\kappa$B), which is activated by exposure to psychosocial stress and noradrenergic activity, and is responsible for cytokine production (Michopoulos, V., et al., *Biol Psychiatry*, 2015, 78(5): 344-353). These individuals may also show increased monocyte sensitivity to glucocorticoids which results in further elevation of inflammatory cytokine production (Id.). Without being bound by theory, neuroinflammation is believed to interfere with memory consolidation as well as with the acquisition and extinction of fear (Michopoulos, V., et al., *Exp Neurol*, 2016, 284: 220-229), which are hallmark characteristics of PTSD.

In addition to biochemical heterogeneity among those individuals with PTSD and those individuals that have been exposed to trauma but did not subsequently develop PTSD, as well as individuals that have not been exposed to such trauma, neuroanatomical differences have also been shown. As discussed above, individuals with PTSD have reduced hippocampal volume, thought to be acquired with trauma exposure (Sherin, J. E., et al., *Dialogues Clin Neurosci*, 2011, 13: 263-278; Michopoulos, V., et al., *Biol Psychiatry*, 2015, 78(5): 344-353). Additionally, the medial prefrontal cortex control of the amygdala may be disrupted in patients with PTSD leading to exaggerated fear responses (Michopoulos, V., et al., *Biol Psychiatry*, 2015, 78(5): 344-353). This dysregulation of the medial prefrontal cortex control of the amygdala may be a predisposed risk factor for the development of PTSD in individuals who experience a qualifying traumatic event (Id.).

No effective treatments currently exist to reverse PTSD. Certain approved drug therapies and cognitive behavioral therapies (e.g., exposure therapy, cognitive restructuring, eye movement desensitization and reprocessing (EMDR) therapy, etc.) are used to provide modest benefit to PTSD patients. Typically, drug therapies are administered to address particular symptoms associated with PTSD in attempts to lessen those particular symptoms. For example, antidepressants (e.g., selective serotonin reuptake inhibitors (SSRIs) that raise the level of serotonin in the brain, tricyclic antidepressants, etc.), anti-anxiety medication (e.g., benzodiazepines, buspirone, $\beta$-blocker, etc.), anti-hypertensive drugs, mood stabilizers, etc., may provide mild to moderate and/or temporary relief from depression-related symptoms, sleep disturbances, hyperarousal symptoms, etc. However, drug adherence over several years or decades in a manner than maintains mood, hyperarousal symptoms, sleep quality, blood pressure, etc., remains a challenge for most patients. Furthermore, some medications do not work or stop working effectively over time. Additional drawbacks to use of drugs for treating a PTSD patient include the possibilities of adverse reactions associated with these medications (e.g., heart failure, hypotension, bradycardia, depression, insomnia, sexual dysfunction, death, etc.) on a patient-by-patient basis. Additionally, pharmaceutical intervention for other contributors and risk factors associated with PTSD further complicates drug administration and management of contraindications between anti-inflammatory medications, anti-hypertensive drugs, antidepressant drugs, anti-anxiety drugs, mood stabilizers among others administered to support PTSD patients, and adherence over years remains a challenge. Various aspects of the present technology address SNS effects on risk factors associated with PTSD while overcoming these challenges.

B. Risk Factors Associated with Development of PTSD

As discussed above, PTSD is an anxiety-related psycho-physiological disorder encompassing dysregulation of complex neuro- and hormonal-biochemical pathways that are known to be caused by many contributing factors. While many biomarkers distinguishing PTSD patients and healthy individuals demonstrate heterogeneity following PTSD pathogenesis in an individual, certain earlier-identifiable conditions as well as genetic and/or biophysical variances in a patient are recognized as being either contributory factors and/or predictors of a likelihood that a patient will develop PTSD following exposure to a traumatic event. In particular, many underlying conditions, genetic variances and other abnormalities detectable in individuals either prior to or at the time of trauma exposure, may affect the likelihood of the individual subsequently developing PTSD. Such underlying conditions and genetic/biophysical variances constitute PTSD predictors or risk factors.

As discussed above, some identified risk factors for increasing a likelihood of developing PTSD include certain demographic variables such as, for example, female gender, divorced or widowed marital status, having a history of mental illness or substance abuse, having little or no social support, having a lack of access to regular healthcare, being under 25 years old (e.g., for military deployment), having experienced prior traumatic events, having an adverse childhood experience, having little or no social support following the traumatic event, and losing a close family member during or shortly after the traumatic exposure, among others (Boscarino, J. A., et al., *Psychiatry Res.*, 2012, 200: 827-834; Liu, X., et al., *J Int Med Res*, 2012, 40: 2191-2198; Sherin, J. E., et al., *Dialogues Clin Neurosci*, 2011, 13: 263-278). Additionally, it has been shown that if the patient suffered an injury or was wounded during the traumatic event, or acquired a traumatic brain injury either before, during or shortly after the traumatic event, the patient had an increased likelihood of developing PTSD (Id.).

Without being bound by theory, increased SNS activity in the patient prior to experiencing a qualifying traumatic event can predispose the individual to developing PTSD. For example, chronic stress has been shown to alter neural circuits and structures in the brain (e.g., hippocampus, prefrontal cortex, etc.) that may increase the individual's sensitivity to contextual threat (Pitman, R. K., et al., *Nat Rev Neurosci.*, 2012, 13: 769-787). Such sensitization of the SNS may be responsible for higher heart rates during a subsequent exposure to a traumatic event, which may be a predictive risk for future development of PTSD (Pitman, R. K., et al., *Nat Rev Neurosci.*, 2012, 13: 769-787; Delahanty, D. L., *Am J Psychiatry*, 2011, 168: 9-11). For example, studies have shown that ambulatory heart rate measured in an individual shortly after experiencing a traumatic event (e.g., at the scene of an accident, during an ER visit following trauma, etc.) was positively associated with subsequent PTSD symptom development, with higher heart rates correlating with more severe PTSD symptoms (Morris, M. C., et al., *Clin Psychol Rev,* 2016, 49:79-91). Moreover, lower heart rate variability characterizes PTSD and also is predictive of PTSD development following a traumatic event (Id.). It has also been shown that individuals that exhibit increased skin conductance (e.g., a measure of sweat activity thought to be under SNS influence) following exposure to loud tones predicted severity of PTSD symptoms following a subsequent exposure to a traumatic event (Pitman, R. K., et al., *Nat Rev Neurosci.*, 2012, 13: 769-787). In certain individuals, prior exposure to trauma (e.g., childhood abuse, prior sexual abuse, prior combat experience, etc.) may increase the individual's sensitization of the SNS, thereby lowering the threshold barriers for the development of the disorder upon subsequent traumatic exposure.

While there is evidence for the presence of SNS hyperactivity in PTSD patients, there is further evidence that a strong adrenergic response to a traumatic event may mediate or in part contribute to the development of PTSD in certain individuals. Some biochemical inducements of the increase in norepinephrine release in response to SNS activation include genetic and/or other inhibition paths that lower NPY levels, as well as lower numbers or affinity of a2-adrenergic receptors (Pitman, R. K., et al., *Nat Rev Neurosci.*, 2012, 13: 769-787; Sherin, J. E., et al., *Dialogues Clin Neurosci,* 2011, 13: 263-278). Additionally, there is evidence that a pro-inflammatory state (e.g., as indicated by increased levels of inflammatory cytokines) may increase risk or vulnerability for development of PTSD upon exposure to a traumatic event (Michopoulos, V., et al., *Biol Psychiatry,* 2015, 78(5): 344-353). For example, it has been shown that, in certain members of the armed forces, pre-deployment levels of CRP were predictive of post-deployment development of PTSD (Id.).

Correlative links between activation of the SNS and high blood pressure, systemic inflammation, arterial stiffness, atherosclerosis, metabolic disorders, insulin resistance, end organ damage, obesity, and other cardiovascular conditions have also been established. As discussed above, these conditions/diseases have further been shown to be correlative with an incidence of PTSD (Michopoulos, V., et al., *Exp Neurol,* 2016, 284: 220-229). As such, it is posited that these conditions/diseases, which are indicative of chronic activation of SNS, present as risk factors that can establish a predictive risk for the development of PTSD upon subsequent exposure to a traumatic event. Additionally, with respect to blood pressure regulation, the nocturnal blood pressure of healthy individuals drops or "dips" more than 10% of the average daytime blood pressure value. In contrast, "elevated," i.e. limited drops in blood pressure during the nighttime (e.g., nighttime blood pressure reduction that is less than 10% of average daytime blood pressure) as well early morning hours, is associated with an increased risk of cardiovascular events and strokes, and such "non-dipping" nocturnal blood pressure is further associated with more PTSD hyperarousal symptoms, poorer overall sleep quality, more frequent use of sleep medication, greater sleep-related daytime dysfunction, and longer sleep onset latencies in PTSD patients, and is predictive of patients having experienced greater trauma exposure (Ulmer, C. S., et al., *Behav Med.*, 2013, 39: 111-121; Kario, K., et al., *Hypertension,* 2015, 66:1130-1137). Accordingly, "non-dipping" nocturnal blood pressure may be a risk factor for the development and/or the severity for one or more symptoms associated with PTSD.

In addition to chronic and/or acute SNS hyperactivity, increased glucocorticoid receptor levels on the patient's leukocytes (e.g., lymphocytes), and certain neuroactivational conditions, provide additional risk factors that can be considered in establishing a predictive risk assessment for the development of PTSD in a patient (Delahanty, D. L., *Am J Psychiatry,* 2011, 168: 9-11; Pitman, R. K., et al., *Nat Rev Neurosci.*, 2012, 13: 769-787). For example, low cortisol levels at the time of trauma exposure is predictive, and thereby provides an additional risk factor, of subsequent PTSD development. Without being bound by theory, it is thought that low levels of cortisol would be insufficient to inhibit CRH/norepinephrine responses to stress and further exacerbate poor fear conditioning and memory consolidation in these individuals (Sherin, J. E., et al., *Dialogues Clin Neurosci,* 2011, 13: 263-278; Delahanty, D. L., *Am J Psychiatry,* 2011, 168: 9-11).

In addition to predisposition factors associated with activation of the SNS and other demographic risk factors, certain genetic variations among individuals have also been shown to be predictive risk factors for the development of PTSD following exposure to a traumatic event. For example, carriers of particular heritable polymorphisms in the genes encoding for FK506-binding protein 5 (FKBP5; co-chaperone of the glucocorticoid receptor that inhibits ligand binding and pathway activation), brain-derived neurotrophic factor (BDNF; neurotrophic factor), and serotonin transporter (SLC6A4; responsible for serotonin transport and reuptake) have been shown to have an increased likelihood of developing PTSD (Mahan, A. L. and Ressler, K. J., *Trends Neurosci,* 2012, 35: 24-35; Pitman, R. K., et al., *Nat Rev Neurosci.*, 2012, 13: 769-787). Further evidence has suggested that in addition to genotype, epigenetic factors such as gene methylation, histone deacetylation, and other gene expression differences can influence or accompany the development of PTSD, and these genetic profiles can be screened to determine patients presenting certain genetic pre-dispositions associated with high or increased risk of developing PTSD C. Identification of Patients or Cohorts Diagnosed with PTSD or at Risk of Developing PTSD Patients presenting with a high likelihood of having PTSD can include patients having experienced a traumatic event and presenting with one or more of (1) core PTSD symptoms (e.g., re-experiencing traumatic experiences, avoidance of trauma-reminding triggers, hyperarousal, mood or emotional modification), (2) depression symptoms, (3) sleep disturbances (e.g., insomnia, difficulty maintain sleep, etc.), (4) suicidal thoughts or tendencies, (5) previously experienced traumatic events or experiences, and/or (6) prior diagnosis of acute stress disorder. Patients having experienced a traumatic event may also have an increased likelihood of having PTSD if they exhibit with one or more of elevated SNS activity (e.g., as detected in urine or plasma), low cortisol levels, low central nervous system NPY levels, high numbers of glucocorticoid receptors on the patient's leukocytes (e.g., lymphocytes), low heart rate variability, limited or no "dipping" of nocturnal blood pressure, and/or elevated levels of serum inflammatory cytokine levels.

Some patients may also present with comorbid conditions or diseases such as hypertension or pre-hypertension, above-normal cholesterol levels, atherosclerosis, insulin resistance or other metabolic disorder, having had a stroke or risk of stroke, arterial stiffening or aneurysm(s), obesity or being overweight (e.g., high BMI), and/or patients with active substance abuse, a history of substance abuse, or prior mental disorder. In certain embodiments, the patient can present with one or more risk factors and/or comorbid conditions associated with an increased likelihood of having PTSD. However, in other embodiments, such associated conditions may not be present in a patient having PTSD and/or at risk of developing PTSD. For example, the patient may be normotensive, have no evidence of cardiovascular disease, normal BMI, normal insulin sensitivity, and/or no elevated levels of inflammatory biomarkers.

Patients presenting with a high or increased risk of developing PTSD can include patients having recently experienced a traumatic event and who have not met the diagnosis standard as set forth in DSM-5 and/or patients in which one or more PTSD screening tools or instruments used to give a professionally-accepted diagnosis have not confirmed PTSD. However, such patients may present one or more risk factors associated with an increased likelihood of developing PTSD either following the recently experienced traumatic event and/or a future traumatic event. For example, the patient may have an increased likelihood of a present condition progressing to PTSD. In another example, the patient may demonstrate a combination of PTSD risk factors (e.g., elevated SNS tone, high number of glucocorticoid receptors on the patient's leukocytes (e.g., lymphocytes), previous traumatic experiences and/or history of child abuse, etc.) and have an occupation having a high risk of exposure to traumatic experiences (e.g., military, first accident and/or disaster responders, etc.).

In particular embodiments, patients having an increased risk of developing PTSD may have, for example, acute stress disorder and demonstrate one or more of the following risk factors: (1) fewer than three core PTSD symptoms (e.g., re-experiencing traumatic experiences, avoidance of trauma-reminding triggers, hyperarousal, mood or emotional modification), (2) depression symptoms, (3) sleep disturbances (e.g., insomnia, difficulty maintain sleep, etc.), (4) suicidal thoughts or tendencies, and/or (5) previously experienced traumatic events or experiences. Further risk factors for the development of PTSD in patients having recently experienced a traumatic event can include physiological markers such as elevated SNS activity (e.g., as detected in urine or plasma), low cortisol levels, low central nervous system NPY levels, high numbers of glucocorticoid receptors on the patient's leukocytes (e.g., lymphocytes), low heart rate variability, limited or no "dipping" of nocturnal blood pressure, elevated heart rate response during stress, low baroreceptor sensitivity (e.g., an assessment of cardiovascular autonomic neuropathy), and/or elevated levels of serum inflammatory cytokine levels. A patient at-risk of developing PTSD following a traumatic event may be hypertensive or pre-hypertensive and/or show elevated SNS tone in the form of blood pressure dysregulation (e.g., elevated 24-hour blood pressure variability). However, in many instances, patients having PTSD or being at-risk of developing PTSD can have normal blood pressure levels (e.g., do not have hypertension or pre-hypertension).

In some embodiments of the present technology, the patient can have experienced one or more traumatic events and have a calculated risk score for determining PTSD status (e.g., diagnosis, severity, etc.) or for the prediction of developing PTSD that is above a threshold PTSD risk score. Such a calculated PTSD risk score can indicate a likelihood of PTSD diagnosis or, in another embodiment, a likelihood of developing PTSD following a recent or a future traumatic event. In one embodiment, for example, a calculated PTSD risk score for determining PTSD status can be based upon one or more data sets known in the art. For example, a PTSD risk score based upon the population-based New York PTSD Risk Score (NYPRS) assessment, which derived data from the World Trade Center Disaster (WTCD) study which included 2,368 New York City adults, the Chronic Pain Study which included 705 patients seen in the Geisinger Clinic, and the Trauma Study which included 225 patients discharged from the Geisinger Clinic's Level-I Trauma Center. The NYPRS can be used to establish a PTSD risk score for determining PTSD status (e.g., diagnosis), and can be based upon an analysis of the patient's assessment across multiple possible risk factors (Boscarino, J. A., et al., *Psychiatry Res.*, 2012, 200: 827-834). For example, the patient can be queried and assessed for core PTSD symptoms, depression symptoms, level of trauma exposure (e.g., number of traumatic events the patient has experienced in a lifetime, duration of trauma exposure, etc.), sleep disturbances (e.g., insomnia, difficulty falling asleep, difficulty maintaining sleep, etc.), and whether the patient has regular access to healthcare. One of ordinary skill in the art will recognize that the NYPRS study is only one study in which a risk score calculation can be developed and applied. For example, another risk score model was developed for identifying risk factors for PTSD and for predicting PTSD in adults in a Chinese earthquake area that showed predictive value for early prediction of PTSD (Liu, X., et al., *J Int Med Res.*, 2012, 40: 2191-2198). Other published data sources documenting multiple possible risk factors and corresponding scores may use any of many well described techniques. Such techniques for developing tools to calculate a PTSD risk score could be empirical, based on multivariate regression, or using artificial intelligence (e.g. Bayesian probability, machine learning, etc.) among other techniques known in the art.

In some embodiments, patients diagnosed with PTSD may also present with one or more depression-related symptoms. Depression-related symptoms may include, for example, feelings of sadness, apathy, mood swings, loss of interest or pleasure in activities, guilt, anxiety, insomnia, restless sleep, excess sleepiness, fatigue, excessive hunger, loss of appetite, irritability, excessive crying, lack of concentration, slowness in activity and thoughts of suicide in the patient. In some embodiments, a patient at risk of developing PTSD may present with these or other depression-related symptoms prior to experiencing a qualifying traumatic event, or in other embodiments, shortly after experiencing a traumatic event. With respect to predicting PTSD status, the presence of depression-related symptoms in males more accurately predicted PTSD diagnosis as well as presented a greater risk factor for the development of PTSD following a traumatic event (Boscarino, J. A., et al., *Psychiatry Res.*, 2012, 200: 827-834). Females, however, are more likely to develop depression or depression-related symptoms, regardless of PTSD status. In certain embodiments, depression-related symptoms may be reported on a depression inventory scale or other assessment tool. For example, patients (with or without PTSD) can be diagnosed with depression or assessed for the presence of depression-related symptoms using the Patient Health Questionnaire (PHQ)-2 scale (a two-item depression screening tool) or the PHQ-9 scale, the Beck Depression Inventory-II (BDI-II), the Major Depression Inventory (MDI), the Hamilton Depression Scale (HAM-D$_{17}$), the Melancholia Scale (YMS), or a Visual Analogue Scale for Depression Severity (VAS) among others, as is known in the art (Bech, P., et al., *BMC Psychiatry*, 2015, 15:190; Boscarino, J. A., et al., *Psychiatry Res.*, 2012, 200: 827-834; Ulmer, C. S., et al., *Behav Med.*, 2013, 39: 111-121).

In other embodiments, a patient presenting a high or increased risk of developing PTSD can have a genetic disorder or determined genetic pre-disposition to developing PTSD upon exposure to traumas. For example, specific forms (e.g., polymorphisms) of the gene known as FKBP5, a co-chaperone of the glucocorticoid receptor, is associated with increased glucocorticoid receptor sensitivity and increased risk for PTSD (Pitman, R. K., et al., *Nat Rev Neurosci.*, 2012, 13: 769-787). As evidence has suggested that genotype, gene methylation, histone deacetylation, and gene expression differences among other epigenetic factors, influence or accompany the development PTSD, these genetic profiles can be screened to determine patients presenting certain genetic pre-dispositions associated with high or increased risk of developing PTSD (Id.).

A patient suspected of having PTSD can be evaluated for a level of dysfunction or severity of symptoms and/or sequelae associated with PTSD. Evaluation of core PTSD symptoms (e.g., re-experiencing, avoidance, hyperarousal and mood/cognition symptoms), depression-related symptoms, sleep disturbances, etc. can include a self-reporting or assessment of changes from a person's usual level of function (e.g., prior to exposure to a traumatic incident) to a current condition (e.g., following exposure to the traumatic incident). Evaluation input may also come from trusted sources (e.g., trusted family members, friends, primary physician, etc.) that can provide information on changes in performance on daily activities, job/employment performance, behavior or mood changes, sleep patterns, as well as angry outbursts, irritability or aggression and/or other risky or destructive behaviors, etc.

Physicians or other qualified clinicians may also administer one or more questionnaires or diagnostic tests, such as screening tools, to assess PTSD risk, severity, and diagnosis. PTSD screening tools such as the PCPS, the SSSP, the APCL, and the SPRINT, the 22 item Self-Report Inventory for PTSD, the Clinician Administered PTSD Scale, the Mississippi Scale for PTSD, as well as other screening instruments, such as the NYPRS, that look at multiple risk factors for predicting PTSD status among at-risk populations can be used to assess core PTSD symptoms. One of ordinary skill in the art will recognize other PTSD tests and scales that can be used to determine status of PTSD in a patient. In some embodiments, a patient may be suspected of having PTSD based upon a single test score or outcome, combined test scores from multiple tests, or one or more test scores from multiple tests. Diagnosis can be made based upon, for example, meeting or exceeding a threshold test score. In other embodiments, a patient may demonstrate an increase in symptom severity as reflected in test scores taken over time. For example, a particular patient may show an increase in PTSD risk via a result in a test score between taking tests one month after experiencing a traumatic event, six months after the traumatic event, and a year or more after experiencing the traumatic event. Cognitive functioning (e.g., cerebral activities encompassing reasoning, memory, attention, and language) and emotional/social functioning (e.g., traits and abilities involving positive and negative aspects of social and emotional life like empathy, interpreting emotion, speed and intensity of emotion generation, and efficacy of coping with negative emotions, etc.), as well as other data that can be collected in an evaluation of a patient, are based on self-report, observational (behavioral), or psychological data.

In a particular example, if a patient who experienced a traumatic event at least one month prior to the time of evaluation could respond (or a clinician could so indicate with respect to a patient) in affirmation (i.e., answering "yes") to three or more of the following questions, then the patient could be diagnosed with PTSD and, in some embodiments, be treated with renal neuromodulation to treat the PTSD:

1. You had repeated bad dreams or nightmares or had disturbing or unpleasant memories, thoughts, or images that kept coming into your mind whether you wanted to think of them or not.
2. You deliberately tried hard not to think about something that happened to you or went out of your way to avoid certain places or activities that might remind you of something that happened in the past.
3. You felt you had to stay on guard much of the time or unexpected noises startled you more than usual.
4. You felt cut off from other people, found it difficult to feel close to other people, or you could not feel things anymore or you had much less emotion than you used to have.

Physicians or other qualified clinicians may also administer one or more questionnaires or diagnostic tests, such as screening tools, to assess depression symptoms that may accompany core PTSD symptoms. For example, the PHQ-2 scale is a two-item depression screener as exemplified in the following questions:

1. Have you ever had a period of two weeks or longer when you were feeling depressed or down most of the day or nearly every day?
2. Have you ever had a period of two weeks or longer when you were uninterested in most things or unable to enjoy things you used to do?

A patient having core PTSD symptoms and one or more depression symptoms can be a candidate for renal neuromodulation.

Additional screening tools or PTSD risk score calculating tools may ask additional questions to identify the presence or absence of known PTSD risk factors. For example, a patient may be asked to respond to one or more of the following questions in an assessment:

How many traumatic events life events do you think you have ever experienced?
Did you experience traumatic life events and/or abuse as a child or adolescent?
Do you have difficulty falling asleep or staying asleep?
Do you have a regular doctor or a usual source of care that you can go to for routine medical care?
Are you single, married, widowed or divorced?
Do you have family or other social support in your life?

In addition to self-reporting, observational, or other psychological data, a patient may also be evaluated for physiological data. Accordingly, a patient may demonstrate one or more physiological parameters associated with PTSD or, in other embodiments, with acute stress disorder. Non-limiting examples of PTSD (or acute stress disorder) associated physiological parameters may include low heart rate variability (e.g., as assessed by Standard Deviation NN intervals (SDNN)), decreased baroreceptor sensitivity (as an assessment of cardiovascular autonomic neuropathy), heightened heart rate responses to stimuli/stress (e.g., via Stroop Color Test or Cold Pressor Test), elevated muscle sympathetic nerve activity (MSNA; a marker of SNS activity), elevated systolic blood pressure, lack of or low levels of nocturnal blood pressure "dipping", higher skin conductance, higher resting heart rate, disrupted sleep patterns or low quality sleep, elevated peripheral inflammatory markers (e.g., IL-6, IL-1β, IL-2, CRP, etc.), low NPY levels (e.g., in the CNS and plasma), and other measures of sympathetic activity (e.g., increased renal and/or total body norepinephrine spillover, increased plasma norepinephrine levels, increased urine levels of norepinephrine and metabolites thereof, etc.). Further physiological parameters that can be risk factors for PTSD may include increased levels of glucocorticoid receptor in patient peripheral blood mononuclear cells (e.g., as assessed via dexamethasone binding assay), brain imaging evidence for detection of prior traumatic brain injury (e.g., as assessed by magnetic resonance imaging (MM), computerized tomography (CT) scan and/or cerebral angiography), reduced hippocampal volume (e.g., as assessed by sMRI), reduced volume of the ventromedial prefrontal cortex (e.g., as assessed by sMRI), altered neural activity in the amygdala (e.g., hyperactivity), ventromedial prefrontal cortex (e.g., hypoactivity), dorsal anterior cingulate cortex (e.g., hyperactivity), hippocampus and/or insular cortex (e.g., as assessed by positron emission tomography (PET) or functional MM (fMRI)), and/or decreased levels of neurotransmitter receptors (e.g., GABA, 5-HT/serotonin) in the brain (e.g., as assessed via administered radioligands followed by PET), (Pitman, R. K., et al., *Nat Rev Neurosci.*, 2012, 13: 769-787).

In accordance with aspects of the present technology, patients presenting with one or more risk factors for having PTSD, having a calculated PTSD risk score, and/or one or more risk factors for developing PTSD can be candidates for treatment for PTSD. In other embodiments, some patients may also be candidates for renal neuromodulation for the prevention of developing PTSD after such patients experience a qualifying traumatic event. As noted above, renal neuromodulation is expected to efficaciously treat PTSD including one or more symptoms associated with PTSD. Renal neuromodulation is also expected to efficaciously prevent an incidence of, reduce a severity of, or slow a progression of PTSD. In other embodiments, renal neuromodulation is expected to therapeutically prevent an incidence of, reduce a severity of, or prevent a progression to PTSD from an acute stress disorder following a traumatic event. Renal neuromodulation is further expected to improve a patient's calculated PTSD risk score correlating to a PTSD status/diagnosis.

In certain embodiments, renal neuromodulation treats several clinical conditions characterized by increased overall sympathetic activity, and, in particular, conditions associated with central sympathetic overstimulation such as pre-hypertension, hypertension, blood pressure variability, heart rate variability, vascular disease (e.g., vessel stiffening), metabolic syndrome, insulin resistance, diabetes, and systemic inflammation, among others, that may be associated with and/or contribute to a severity or progression of PTSD in a patient. The reduction of afferent neural signals typically contributes to the systemic reduction of sympathetic tone/drive, and renal neuromodulation is expected to be useful in treating several conditions associated with systemic sympathetic overactivity or hyperactivity.

II. Renal Neuromodulation for Treating Ptsd and/or Reducing a Risk Associated with the Development of PTSD As discussed in further detail below, and in various embodiments, therapeutically-effective renal neuromodulation can be used for the treatment of PTSD or for the treatment of one or more symptoms and/or sequelae associated with PTSD, the management of PTSD, or to reduce an incidence of PTSD in patients identified as having had a qualifying traumatic event. In further embodiments, therapeutically-effective renal neuromodulation can be used for treating a patient (e.g., a patient having one or more risk factors associated with developing PTSD) prior to experiencing a potential traumatic event (e.g., military combat) for reducing a risk associated with developing PTSD following such potential exposure.

While sympathetic drive regulation can have adaptive utility in maintaining homeostasis or in preparing many organs in the body for a rapid response to environmental factors, chronic activation of the SNS (e.g., associated with acute stress syndrome, chronic stress, primary aging, age-associated obesity, etc.) is a common maladaptive response that can contribute to diseases/conditions (e.g., hypertension, systemic or localized inflammation, vascular remodeling, atherosclerosis, obesity, insulin resistance, metabolic syndrome, etc.) or predispose individuals to psychophysiological adaptations that can increase a patient's risk of developing PTSD and/or drive progression and/or severity of PTSD in a patient. Excessive activation of the renal SNS in particular has been identified experimentally and in humans as a likely contributor to the complex pathophysiology of hypertension, states of volume overload (such as heart failure), systemic inflammation, and progressive renal disease. As examples, radiotracer dilution has demonstrated increased renal norepinephrine spillover rates in patients with essential hypertension.

Aspects of the present disclosure include targeting renal SNS nerve fibers for neuromodulation in patients (1) having been diagnosed with PTSD, (2) demonstrating one more physiological and/or psychological symptoms associated with PTSD, and/or (3) having an increased risk associated with developing PTSD. Targeting renal SNS nerve fibers for neuromodulation in patients can effectively attenuate neural traffic along the sympathetic nerves. Without being bound by theory, attenuation of neural traffic along renal sympathetic nerves can be used, for example, to treat or prohibit one or more hallmark symptoms associated with PTSD, decrease systemic inflammatory responses associated with PTSD, and/or decrease a level of severity of PTSD and/or symptoms associated with PTSD. In some embodiments, hallmark symptoms of PTSD that can be treated, reduced or prevented via attenuation of neural traffic along renal sympathetic nerves can include, for example, heightened startle responses, hyperarousal, sleep disturbances, fear memory consolidation and/or conditioning, excessive sweating in response to perceived threat and/or stress, and undesirable elevations in heart rate, blood pressure, and skin conductance.

In further embodiments, attenuation of neural traffic along renal sympathetic nerves can be used to treat a patient at risk of developing PTSD following exposure of a qualifying traumatic event in a manner that prevents development of PTSD in the at-risk patient. In yet another embodiment, attenuation of neural traffic along renal sympathetic nerves in an individual having one or more risk factors associated with developing PTSD can be used for reducing a risk associated with developing PTSD following a potential exposure to a traumatic event (e.g., military combat).

As discussed above, several diseases and conditions have high comorbidity with PTSD diagnosis, including, for example, major depressive disorder, substance and alcohol abuse/addiction, panic disorder, cardiovascular disease, hypertension, obesity (e.g., high BMI), and metabolic disorders, such as type 2 diabetes. In certain embodiments, patients having PTSD and one or more comorbid conditions and/or diseases can be treated with renal neuromodulation to treat and/or reduce severity of the PTSD and/or the one or more comorbid conditions/diseases. In another example, renal neuromodulation can be used to therapeutically treat a patient diagnosed with PTSD for preventing and/or reducing an incidence of developing one or more comorbid conditions/diseases, including those conditions/diseases wherein chronic SNS activity is known to be a contributing factor (e.g., hypertension, cardiovascular disease, etc.).

In one example, renal sympathetic neuromodulation can be used to reduce a patient's systolic blood pressure, including a nocturnal blood pressure level. In another example, renal sympathetic neuromodulation can be used to increase heart rate variability (e.g., the beat-to-beat fluctuations in heart rate) in a patient. In other embodiments, attenuation of neural traffic along renal sympathetic nerves can be used to treat or prevent metabolic disorders, obesity and/or insulin resistance in the patient having PTSD or at increased risk associated with developing PTSD following a traumatic event. In yet a further embodiment, renal sympathetic neuromodulation can be used to lower one or more levels of inflammatory biomarkers in a patient.

Certain effects of chronic SNS activation that take place prior to experiencing a potential traumatic event may be associated with an increased risk of developing PTSD following such an exposure. Many of these effects may not yield noticeable signs or symptoms associated with a disease; however, the effects of chronic SNS activation can cause unseen damage to cardiac tissue, brain tissue, and/or vascular tissue, as well as disrupt normal neurophysiological and hormonal balances throughout the body prior to the appearance of quantifiable disease indicators typically associated with maladaptive SNS activation and/or prior to exposure to a traumatic event in the predisposed or at-risk individual. Accordingly, in one embodiment, neuromodulation treatment can be used to treat patients having a high risk of developing PTSD. For example, patients may present one or more risk factors for developing PTSD following a qualifying traumatic event (e.g., having been diagnosed with acute stress disorder, having been diagnosed with chronic stress prior to the traumatic event, having an elevated heart rate, having reduced heart rate variability, having elevated levels of glucocorticoid receptors on the patient's leukocytes (e.g., lymphocytes), having elevated systemic plasma levels of inflammatory biomarkers (e.g., IL-6, CRP, etc.), having high blood pressure, having low cortisol levels, having a genetic predisposition (e.g., FKBP5 variance, etc.). In other examples, such patients having a high risk of developing PTSD may present one or more social or demographic risk factors for the development of PTSD (e.g., prior exposure to trauma, female gender, reduced access to medical care, widowed or divorced marital status, prior traumatic brain injury, etc.).

In still further embodiments, neuromodulation treatment can be used to treat patients for improving a PTSD risk score for a patient diagnosed with PTSD. Such a risk score may be determined, for example, using a PTSD-screening tool for determining a severity of PTSD in the patient. For example, certain patients can have a PTSD risk score above a threshold PTSD risk score, can have one or more PTSD risk factors, have a combination of PTSD risk factors, etc., and renal neuromodulation can be used to therapeutically reduce (a) systemic plasma levels of norepinephrine from, e.g., spillover from innervation of smooth muscle surrounding blood vessels, (b) systemic plasma levels of inflammatory biomarkers (e.g., IL-6, CRP, etc.), and/or (c) high blood pressure. In other embodiments, neuromodulation treatment can be used to increase heart rate variability or decrease heighted startle responses in patients.

In one embodiment, a patient having experienced a qualifying traumatic event less than 1 month prior and presenting with one or more acute stress indicators or other indicators, such as pre-hypertension (e.g., systolic BP of 120-139 mmHg/diastolic BP of 80-89 mmHg), hypertension (e.g., systolic BP>140 mmHg/diastolic BP>90 mmHg), increased serum levels of IL-6 or CRP, higher levels of glucocorticoid receptors on the patient's leukocytes (e.g., lymphocytes), decreased heart rate variability, or having other factors presenting an increased risk of developing PTSD (e.g., persons having history of abuse or other traumatic events, FKBP5 polymorphism, etc.) can be treated with renal neuromodulation to reduce a level of renal sympathetic drive and/or reduce a level of systemic norepinephrine spillover in circulating plasma (Schlaich, M. P., et al., *Frontiers in Physiology*, 2012, 3(10): 1-7).

In some embodiments, a patient demonstrating acute stress indicators for greater than 1 month following a traumatic event can be diagnosed with PTSD by a physician or qualified clinician. In other embodiments, a patient demonstrating acute stress indicators can present with a qualifying result on a PTSD screening tool (e.g., tool for assessing PTSD diagnosis, tool for assessing PTSD risk status, etc.). In further embodiments, acute stress indicators arising within about 1 month following a traumatic event can refer to patients diagnosed with acute stress disorder, and patients may be treated with renal neuromodulation to prevent a future on-set of PTSD, reduce a risk factor score associated with the severity of PTSD, reduce a severity of one or more symptoms associated with PTSD, or reduce an incidence of developing one more comorbid conditions/diseases.

Several embodiments of the present technology utilize intravascular devices that reduce sympathetic nerve activity by applying, for example, radiofrequency (RF) energy to target nerve(s) or target site(s) in patients presenting one or more physiological symptoms associated with PTSD, acute stress disorder, chronic anxiety or other panic disorder, or having a risk of developing PTSD, such as having one or more PTSD risk factors. In certain embodiments, neuromodulation is used to reduce renal sympathetic nerve activity in patients having a high risk (e.g., a predisposition or increased likelihood) of developing PTSD, one or more signs or symptoms associated with PTSD development, or, in further embodiments, in patients having been diagnosed with PTSD. In a particular embodiment, neuromodulation is used to reduce renal sympathetic nerve activity in patients having a PTSD risk score (e.g., indicating a status or severity of PTSD) above a threshold risk score.

Renal neuromodulation is the partial or complete incapacitation or other effective disruption of the nerves of the kidneys, including nerves terminating in the kidneys or in structures closely associated with the kidneys. In particular, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). While long-term disruption of the renal nerves can be desirable for preventing incidence of or treating PTSD, reducing a severity of PTSD, or for alleviating symptoms and other sequelae associated with PTSD over longer periods of time, short-term modulation of the renal nerves may also be desirable. For example, some patients may benefit from short-term renal nerve modulation to address acute symptoms following exposure to a traumatic event, such as heighted startle responses, hyperarousal, social or other anxiety, insomnia, nightmares, mood swings, or other stress/anxiety/panic-related behavioral changes. In particular, some patients may benefit from short-term renal nerve modulation to address the effects of grief, guilt or depression following an experienced traumatic event such as, for example, an accident or natural disaster or loss of a loved one. In other instances, some patients may benefit from short-term renal nerve modulation as adjuvant therapy to increase effectiveness of co-administered drugs (e.g., anti-inflammatory medications, anti-hypertensive drugs, antidepressant drugs, anti-anxiety drugs, and sleeping medications among others administered to support PTSD patients) and/or cognitive behavioral therapy (e.g., cognitive processing therapy, prolonged exposure therapy, EMDR, etc.).

Figure 3:
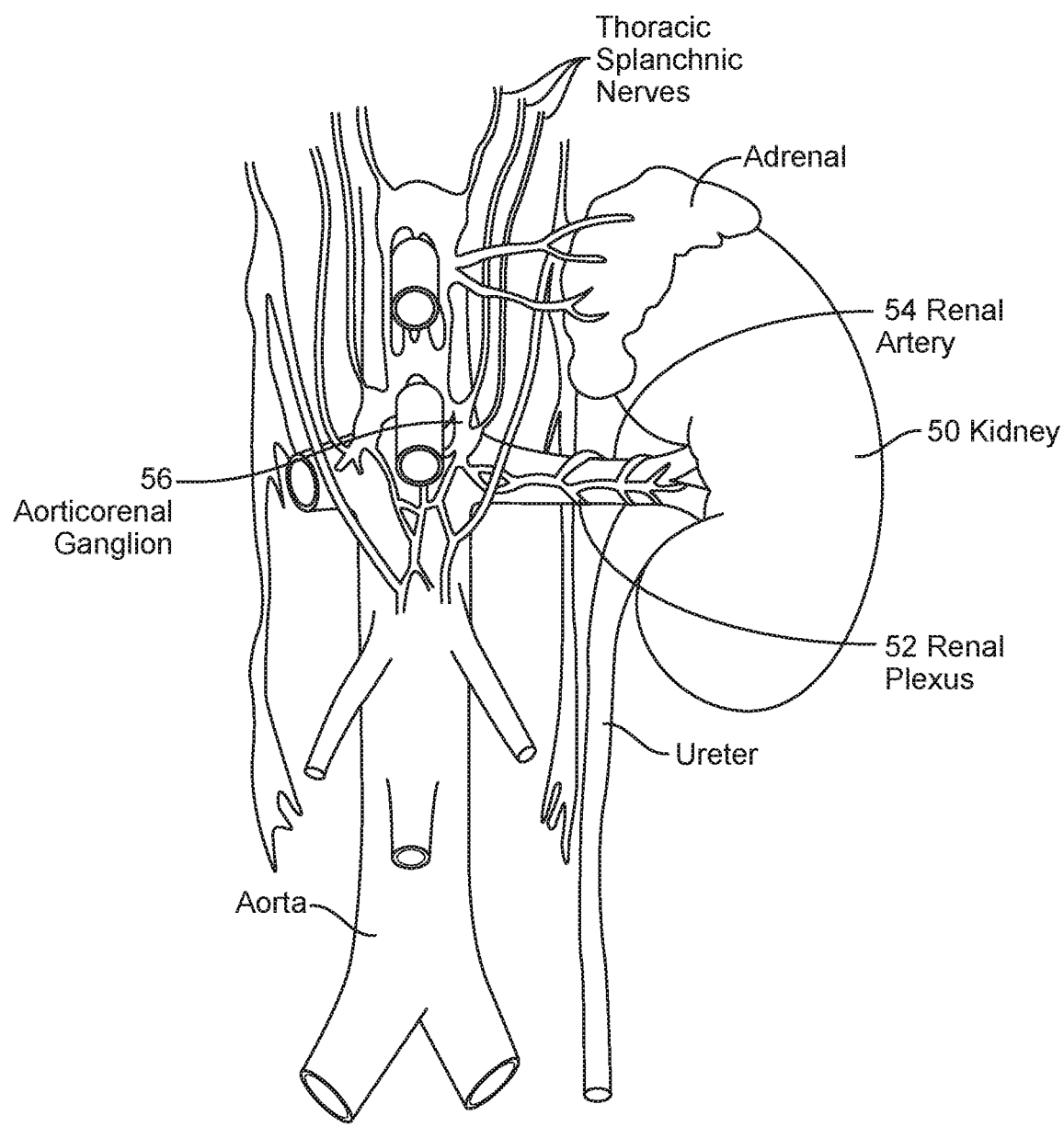
FIG. 3 is an enlarged anatomic view of nerves of a left kidney to form the renal plexus surrounding the left renal artery.

FIG. 3 is an enlarged anatomic view of nerves innervating a left kidney 50 of a patient. As FIG. 3 shows, the kidney 50 is innervated by a renal plexus 52, which is intimately associated with a renal artery 54. The renal plexus 52 is an autonomic plexus that surrounds the renal artery 54 and is embedded within the adventitia of the renal artery 54. The renal plexus 52 extends along the renal artery 54 until it arrives at the substance of the kidney 50, innervating the kidneys while terminating in the blood vessels, the juxtaglomerular apparatus, and the renal tubules (not shown). Fibers contributing to the renal plexus 52 arise from the celiac ganglion (not shown), the superior mesenteric ganglion (not shown), the aorticorenal ganglion 56 and the aortic plexus (not shown). The renal plexus 52, also referred to as the renal nerve, is predominantly comprised of sympathetic components. There is no (or at least very minimal) parasympathetic innervation of the kidney 50.

Preganglionic neuronal cell bodies are located in the intermediolateral cell column of the spinal cord (renal sympathetic nerves arise from T10-L2, FIG. 2). Referring to FIGS. 2 and 3 together, preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion (FIG. 2), the superior mesenteric ganglion (FIG. 2), and the aorticorenal ganglion 56. Postganglionic neuronal cell bodies exit the celiac ganglion, the superior mesenteric ganglion, and the aorticorenal ganglion 56 to the renal plexus 52 and are distributed to the renal vasculature.

It has previously been shown that stimulation of renal efferent nerves directly affects neural regulation components of renal function that are considerably stimulated in disease states characterized by heightened sympathetic tone such as, for example, increased blood pressure in hypertensive patients. As provided herein, renal neuromodulation is likely to be valuable in the treatment of PTSD and/or symptoms associated with PTSD. Renal neuromodulation is also likely to be valuable in the prevention of developing PTSD in certain at-risk individuals (e.g., individuals having experienced a traumatic event and presenting one or more acute stress indicators or biomarkers indicating a high likelihood of developing PTSD). Renal neuromodulation may also likely to be valuable in the treatment of diseases and conditions that are associated with PTSD and/or increased SNS tone such as, for example, hypertension, increased blood pressure variability, systemic inflammation, vascular inflammation, vessel remodeling and/or hardening, atherosclerosis, metabolic disorders, and major depressive disorder among others. In particular, renal neuromodulation along the renal artery and/or within branches of the renal artery as described in U.S. patent application Ser. No. 14/839,893, filed Aug. 28, 2015 and incorporated herein by reference in its entirety, is expected to reduce renal sympathetic drive in the kidney, thereby reducing the negative impact of SNS activation on aspects of these and other conditions associated with physiological changes that have impact on psychological and cognitive health. As such, renal neuromodulation is also likely to be particularly valuable in patients having one or more clinical conditions characterized by increased overall and particularly renal sympathetic activity, such as hypertension, increased blood pressure variability, low heart rate variability, systemic inflammation, chronic vascular inflammation, metabolic syndrome, insulin resistance, diabetes, anxiety disorder, and depression among others.

As the reduction of afferent neural signals contributes to the systemic reduction of sympathetic tone/drive, renal neuromodulation might also be useful in preventing PTSD, particularly prior to experiencing a potential traumatic event. For example, a reduction in central sympathetic drive may reduce and/or improve measurable physiological parameters typically associated with the development of PTSD, prior to exposure to a potential traumatic event. Alternatively, a reduction in central sympathetic drive may, for example, reduce an elevated heart rate or heightened startle response, improved blood pressure, improve heart rate variability, increase blood flow to the brain, reduce cerebrovascular inflammation, reduce systemic inflammation, and/or improve other chronic stress-related symptoms such as generalized anxiety and sleep disturbances (e.g., insomnia, etc.).

In accordance with several aspects of the present technology, renal neuromodulation is used for the prevention of or treatment of PTSD. Other psychologically and/or neurologically related conditions, such as, e.g., chronic anxiety, panic disorder (e.g., frequent panic attacks), and insomnia, as well as other conditions presented as comorbid with PTSD such as, for example, depression (major depressive disorder), hypertension, high BMI (e.g., obesity), and metabolic disorder (e.g., diabetes), may also be treatable or preventable using renal neuromodulation.

Intravascular devices that reduce sympathetic nerve activity by applying, for example, RF energy to a target site in the renal artery have recently been shown to reduce blood pressure in patients with treatment-resistant hypertension. The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent RAAS activation) and sodium retention and decreased renal blood flow. These neural regulation components of renal function are considerably stimulated in disease states characterized by heightened sympathetic tone and likely contribute to increased blood pressure in PTSD patients and increased levels of peripheral inflammatory markers, such as IL-6 and CRP, in PTSD patients experiencing a host of inflammatory challenges (Michopoulos, V., et al., *Exp Neurol*, 2016, 284: 220-229).

Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via radio frequency (RF) ablation) have been shown to be efficacious in reducing blood pressure, decreasing blood pressure variability, decreasing nocturnal blood pressure, improving arterial stiffness and reducing mediators of systemic inflammation in patients with treatment-resistant hypertension (Dörr, O., et al., *Clin Res Cardiol*, 2015, 104: 175-184; Zuern, C. S., et al., *Front. Physiol*, 2012, 3(134): 1-8; Baroni, M., et al., *High Blood Press Cardiovasc Prev*, 2015, (4):411-6; Brandt, M. C., et al., JACC, 2012, 60(19): 1956-65; Mortensen, K., et al., *J Clin Hypertens*, 2012, 14(12): 861-870; Kario, K., et al., *Hypertension*, 2015, 66:1130-1137).

Various techniques can be used to partially or completely incapacitate neural pathways, such as those innervating the kidney. The purposeful application of energy (e.g., electrical energy, thermal energy) to tissue can induce one or more desired thermal heating and/or cooling effects on localized regions along all or a portion of a renal blood vessel (e.g., renal artery, renal arterial branch, renal ostium, renal vein) and adjacent regions of the renal plexus RP, which lay intimately within or adjacent to the adventitia of the renal blood vessel. Some embodiments of the present technology, for example, include electrode-based or transducer-based approaches, which can be used for therapeutically-effective neuromodulation. For example, an energy delivery element (e.g., electrode) can be configured to deliver electrical and/or thermal energy at a treatment site.

By way of theory, targeting both general afferent and efferent renal sympathetic nerves (e.g., via a catheter-based approach, utilizing extracorporeal ultrasound) may cause beneficial effects extending well beyond affecting a severity of PTSD or a risk associated with developing PTSD, such as reducing a risk of developing hypertension, stroke, cardiovascular disease, obesity, metabolic disorder or other end organ damage. As discussed herein, a correlation between hyperactivity of the SNS and an increased risk of developing PTSD and an increased risk in promoting more severe PTSD symptoms has been implicated. There is now also evidence that PTSD and related symptom severity is associated with chronic inflammatory responses and sympathetic activation appears to affect serum levels of peripheral inflammatory markers. Additionally, chronic stress, obesity and other cardiovascular maladies promote hyperactivity (e.g., overactivity) of the sympathetic nervous system throughout the body. For example, when experiencing stress, including chronic stress, hormonal and neural information (e.g., sensory afferent input) is received by the CNS, which in turn further elevates sympathetic tone via efferent signaling throughout the body. Some aspects of methods of treating patients having PTSD or having one or more risk factors, including a high risk score, for the development of PTSD, using sympathetic neuromodulation are at least in part derived from the recognition described herein that the kidneys may contribute to elevated central sympathetic drive.

Several aspects of the current technology are configured to reduce renal sympathetic nerve activity within or near the kidney(s) to reduce localized release of norepinephrine. Several properties of the renal vasculature may inform the design of treatment devices and associated methods for achieving target sympathetic neuromodulation, for example, via intravascular access, and impose specific design requirements for such devices. Specific design requirements for renal neuromodulation may include accessing the renal artery, a ureter, a renal pelvis, a major renal calyx, a minor renal calyx, and/or another suitable structure; facilitating stable contact between the energy delivery elements of such devices and a luminal surface or wall of the suitable targeted structure, and/or effectively modulating the renal nerves with the neuromodulatory apparatus.

Intravascular devices that reduce sympathetic nerve activity by applying, for example, RF energy to a treatment site in the renal artery have recently been shown to reduce renal sympathetic drive, renal norepinephrine spillover, and whole body norepinephrine spillover. Renal neuromodulation is expected to reduce renal sympathetic neural activity, and since the reduction of afferent neural signals contributes to the systemic reduction of sympathetic tone/drive, renal neuromodulation is a useful technique in addressing certain risk factors and symptoms associated with PTSD that are attributable to systemic sympathetic hyperactivity. For example, as previously discussed, a reduction in central sympathetic drive may treat PTSD including reducing a severity of one or more symptoms associated with PTSD, reduce a likelihood of developing PTSD following experiencing a traumatic event, as well as improve other comorbid disease manifestations (e.g., hypertension, metabolic disorders, insulin resistance, diabetes, systemic inflammation, major depressive disorder, generalized anxiety, panic attacks, etc.) associated with sympathetic hyperactivity.

Accordingly, renal neuromodulation is expected to be useful in treating PTSD, reducing a severity of one or more symptoms in patients afflicted with PTSD, preventing and/or treating one or more comorbid conditions or diseases associated with PTSD or preventing an incidence of developing PTSD in patients presenting certain risk factors. The beneficial effect of renal neuromodulation with respect to a risk associated with development of PTSD is expected to apply to patients having recently (e.g., less than about one month prior) experienced a qualifying traumatic event, for example, regardless of the baseline renal sympathetic neural activity or the baseline level of norepinephrine in plasma (e.g., whole body norepinephrine spillover). For example, renal neuromodulation in accordance with embodiments of the present technology can improve one or more measurable physiological parameters corresponding to a PTSD risk factor or status (e.g., level of severity of diagnosis) in the patient when baseline renal sympathetic neural activity is normal, below normal, or above normal (e.g., hyperactive or overactive). Likewise, renal neuromodulation in accordance with additional embodiments of the present technology can improve one or more measurable physiological parameters corresponding to a PTSD risk factor or PTSD status (e.g., level of severity of diagnosis) in the patient when baseline central sympathetic drive, baseline norepinephrine spillover in plasma, and/or whole body norepinephrine spillover is normal, below normal, or above normal (e.g., hyperactive or overactive). Such an improvement in one or more measurable physiological parameters corresponding to a PTSD risk factor or PTSD status (e.g., level of severity of diagnosis) in the patient can reduce a risk associated with developing PTSD in that patient or can reduce symptom severity and/or effectively treat an afflicted patient diagnosed with PTSD.

III. Methods for Treating Ptsd and/or Reducing a Risk Associated with Developing PTSD and Related Conditions Disclosed herein are several embodiments of methods directed to treating an incidence of PTSD in a patient using catheter-based renal neuromodulation. Further embodiments disclosed herein are directed to preventing an incidence of PTSD and/or other conditions associated with an increased risk of developing PTSD in a patient via catheter-based renal neuromodulation. The methods disclosed herein may represent various advantages over a number of conventional approaches and techniques in that they allow for the potential targeting of elevated sympathetic drive, which may either be a cause of several neurological, immune vascular, or other physiological risk factors associated with PTSD or a key mediator of the disorder manifestation. Also, the disclosed methods provide for localized treatment and limited duration treatment regimens (e.g., one-time treatment), thereby reducing patient long-term treatment compliance issues.

In certain embodiments, the methods provided herein comprise performing renal neuromodulation, thereby decreasing sympathetic renal nerve activity, for example, for the purposes of being able to provide one or more of a reduction in a number of PTSD risk factors, a reduction in severity of one or more PTSD risk factors, a reduction in a calculated PTSD risk score, a reversal in vascular damage facilitated by sympathetic activity, or a reduction in systemic inflammation. For example, renal neuromodulation is expected to reduce a level of central sympathetic activity that may contribute to one more underlying causes of PTSD.

Renal neuromodulation may be repeated one or more times at various intervals until a desired sympathetic nerve activity level or another therapeutic benchmark is reached. In one embodiment, for example, a decrease in sympathetic nerve activity may be observed via a marker of sympathetic nerve activity in patients, such as decreased levels of plasma norepinephrine (noradrenaline), changes in levels of systemic renin in plasma, and/or changes in levels of systemic aldosterone in plasma. Other measures or markers of sympathetic nerve activity can include MSNA, norepinephrine spillover, and/or heart rate variability. In some instances, a decrease in SNS activity can be observed as a decrease in norepinephrine and metabolites thereof (e.g., vanillomandelic acid (VMA)) in urine. In another embodiment, other measurable physiological parameters or markers, such as improved baroreceptor sensitivity, improved heart rate responses to stimuli/stress, improved heart rate variability, improved skin conductance, improved blood pressure control (e.g., lower blood pressure), improved blood pressure variability (e.g., improved nocturnal blood pressure "dipping"), lower levels of peripheral inflammatory biomarkers (e.g., IL-6, IL-1β, IL-2, CRP, etc.), improved levels of NPY, reduced glucocorticoid receptor sensitivity, improved brain neural activity (e.g., in the amygdala, ventromedial prefrontal cortex, dorsal anterior cingulate cortex, hippocampus, insular cortex), cessation or reversal of brain atrophy (e.g., in the hippocampus, in the ventromedial prefrontal cortex), changes in aldosterone-to-renin ratio (ARR), changes in a salt suppression test, changes in blood plasma levels of potassium, improved blood glucose regulation, etc., can be used to assess efficacy of the thermal modulation treatment for patients diagnosed as having PTSD or for patients having one or more risk factors for developing PTSD, having a calculated PTSD risk score above a threshold PTSD risk score, and/or having developed acute stress disorder. In certain embodiments, renal neuromodulation may be repeated one or more times at various intervals until a desired sympathetic nerve activity level or another therapeutic benchmark is reached for such patients.

In certain embodiments of the methods provided herein, renal neuromodulation is expected to result in a change in sympathetic nerve activity and/or in other measurable physiological parameters or markers, over a specific timeframe. For example, in certain of these embodiments, sympathetic nerve activity levels are decreased over an extended timeframe, e.g., within 1 month, 2 months, 3 months, 6 months, 9 months or 12 months post-neuromodulation.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity level may be measured in the subject at one or more timepoints prior to treatment. A baseline sympathetic nerve activity value may represent sympathetic nerve activity at a specific timepoint before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months, 12 months or 24 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

In one embodiment, measured norepinephrine content (e.g., assessed via tissue biopsy, assessed in real-time via intravascular blood collection techniques, assessed in real-time via urine, etc.) can be reduced (e.g., at least about 5%, 10%, 20% or by at least 40%) in the patient within, for example, about three months after at least partially inhibiting sympathetic neural activity in nerves proximate a renal blood vessel.

In one embodiment, renal sympathetic neuromodulation may be performed on a patient having one or more risk factors or symptoms associated with PTSD to improve the physiological state of at least one of the PTSD risk factors. In some embodiments, for example, renal sympathetic neuromodulation may result in a reduction in a patient's heart rate under stress, may raise heart rate variability, lower a nocturnal blood pressure level, reduce systolic blood pressure, reduce blood pressure variability, increase baroreceptor sensitivity, lower skin conductance, reduce a serum level of an inflammatory biomarker, or reduce a level of insulin resistance. In a particular example, a patient having PTSD and decreased heart rate variability (e.g., SDNN<50 ms) may have heart rate variability within a normal range (e.g., SDNN>50 ms) after a neuromodulation procedure. In a further example, a reduction in nocturnal blood pressure level can be, for example, by at least about 5%, 10%, or a greater amount as determined by average ambulatory blood pressure analysis before and after (e.g., 1, 3, 6, or 12 months after) a renal neuromodulation procedure.

In the case of systemic inflammation and/or a patient having elevated serum levels of inflammatory biomarkers, IL-6 and CRP, renal sympathetic neuromodulation may improve (e.g., reduce a level of) markers of inflammation (e.g., IL-6, CRP) and, in some embodiments, provide a reduction in IL-6 and/or CRP, for example, by about 5%, 10%, 25%, 45% or a greater amount as determined by blood analysis before and after (e.g., 1, 3, 6, or 12 months after) a renal neuromodulation procedure. In an example where the patient has increased glucocorticoid sensitivity, renal sympathetic neuromodulation may improve (e.g., reduce a level of) glucocorticoid sensitivity by about 5%, about 10%, about 20% or greater amount as determined by quantitative analysis (e.g., dexamethasone binding assay, dexamethasone suppression test, etc.). In other embodiments, and in particular afflicted patients, renal sympathetic neuromodulation may increase arteriole blood flow, reduce a level of atherosclerosis, or reduce a degree of arterial stiffening in the patient by about 5%, 10% or a greater amount as determined by qualitative or quantitative analysis (e.g., CT scan, pulse wave velocity (PWV) analysis, angiography, etc.) before and after (e.g., 1, 3, 6, or 12 months after) a renal neuromodulation procedure.

In another embodiment, renal sympathetic neuromodulation may be performed on a patient having a calculated PTSD risk score associated with a PTSD status in the patient that is above a threshold PTSD risk score. Renal neuromodulation is expected to therapeutically improve the patient's PTSD risk score and thereby reduce, diminish, reverse or eliminate the PTSD disorder in the patient. In one embodiment, a threshold PTSD risk score may be a theoretical risk score (e.g., based on population studies) that represents a cut-off score for a PTSD diagnosis. In other embodiments, the threshold PTSD risk score may be a theoretical risk score that represents an upper limit of acceptable severity and/or acceptable risk of developing PTSD following a traumatic event or experience.

In a particular example, a patient may be assessed for a number of factors that have been previously determined to validate a PTSD diagnosis and/or to carry risk for the development of PTSD (e.g., number or severity of core PTSD symptoms, depression symptoms, presence of sleep disturbances, number of prior traumatic events the patient experienced, presence of abuse or neglect during childhood, gender, marital status, level of access to healthcare, absence of family and/or social support, low heart rate variability, heightened heart rate response to stimuli, elevated levels of glucocorticoid receptors (e.g., found on leukocytes), baroreceptor sensitivity, blood pressure, MSNA levels, body mass index, substance abuse/habits, etc.). Using a PTSD risk score calculator tool (e.g., based on epidemiological data), a patient's risk score can be assessed. For patients having a calculated PTSD risk score above the threshold PTSD risk score (e.g., signifying an undesirable PTSD level of severity or probability of having PTSD), a renal sympathetic neuromodulation procedure is performed. Renal neuromodulation may improve (e.g., lower, reverse, reduce a rate of increase over time, etc.) the patient's PTSD risk score. For example, following a renal neuromodulation procedure, a patient's calculated PTSD risk score may reduce (e.g., improve) by about by about 5%, 10%, 15%, 20%, 25%, 30%, 40%, 45% or a greater amount as determined by the PTSD risk score calculator tool. Such improvements in a patient's PTSD risk score may be detected, for example 1, 3, 6, 12, or 24 months after a renal neuromodulation procedure. In certain embodiments, a threshold risk score can be variable depending on a number of factors including gender, age, socioeconomic levels, geographical residence, etc. For example, a threshold risk score for a male patient can be greater than a threshold risk score for a female patient.

In addition to (or instead of) affecting one or more measurable risk factors associated with PTSD or the development of PTSD, renal sympathetic neuromodulation may efficaciously treat one or more measurable physiological parameter(s) or sequela(e) corresponding to the progression or severity of PTSD in the patient. For example, in some embodiments, renal neuromodulation may result in an improvement (e.g., prevent further decline, maintain, or improve) in a patient's cognitive abilities and/or emotional/social functioning abilities as assessed by one or more accepted diagnostic test methods (e.g., screening tools, questionnaires, etc.) for identifying PTSD risk, severity and diagnosis (e.g., PCPS, SSSP, APCL, SPRINT, etc.). In a specific embodiment, a patient may improve a PTSD screening test score, maintain a PTSD screening test score, or decrease a rate of decline (e.g., rate of PTSD disorder progression) in a test score over time following a renal neuromodulation procedure. Such improvements in a patient's cognitive abilities and/or emotional/social functioning abilities may be detected, for example 1, 3, 6, or 12 months after a renal neuromodulation procedure. In other embodiments, improvements are detected 2, 3, 4, 5 or 10 years after a renal neuromodulation procedure. In some embodiments, a PTSD diagnostic test score can be improved by about 5%, about 10%, about 15%, about 20%, about 30%, about 40%, about 50%, or about 75%. In other embodiments, patients may report that daily activities are easier following a neuromodulation procedure.

In another example, renal sympathetic neuromodulation may efficaciously treat one or more aspects of sleep disturbance associated with PTSD in the patient. For example, a patient may have an improvement (e.g., a reduction) in the number, the type and/or the duration of sleep disturbances (e.g., number of nights of difficulty falling asleep, number of nights difficulty maintaining or staying asleep, duration of time it takes to fall asleep, duration of night awake, number of times patient wakes up during the night, etc.) following a renal neuromodulation procedure. Such improvements in a patient's sleep patterns and/or sleep quality may be detected, for example 1, 3, 6, or 12 months after a renal neuromodulation procedure. In other embodiments, improvements are detected 2 or 3 years after a renal neuromodulation procedure. In some embodiments, the patient's sleep quality (e.g., number of nights with sleep disturbance, time duration of sleep disturbance, etc.) can be improved by about 5%, about 10%, about 15%, about 20%, about 30%, about 40%, about 50%, or about 75% within 3 to 12 months or within 3 to 6 months following a renal neuromodulation procedure.

In a further example, renal sympathetic neuromodulation may efficaciously treat one or more aspects of depression or depression-related symptoms associated with PTSD in the patient. For example, a patient may have an improvement (e.g., a reduction) in the number, the type, and/or the severity of depression-related symptoms (e.g., feeling depressed or down most days or nearly every day, feelings of sadness, apathy, mood swings, loss of interest or pleasure in activities, guilt, anxiety, insomnia, restless sleep, excess sleepiness, fatigue, excessive hunger, loss of appetite, irritability, excessive crying, lack of concentration, slowness in activity and/or thoughts of suicide) following a renal neuromodulation procedure. Such improvements in a patient's depression-related symptoms may be detected, for example, 1, 3, 6, or 12 months after a renal neuromodulation procedure. In other embodiments, improvements are detected 2 or 3 years after a renal neuromodulation procedure. In some embodiments, the level of depression-related symptoms (e.g., level of severity, number of depression-related symptoms, the number of days the patient experiences depression-related symptoms within a logged time period, etc.) can be improved by about 5%, about 10%, about 15%, about 20%, about 30%, about 40%, about 50%, or about 75% within, for example, 3 to 12 months or within 3 to 6 months following a renal neuromodulation procedure. In some embodiments, the patient can experience complete regression or full recovery from the depression-related symptoms.

Renal neuromodulation may prevent or reduce an incidence of developing one or more comorbid conditions or diseases in a patient with PTSD. For example a PTSD patient treated with renal neuromodulation may have a decreased likelihood of developing pre-hypertension, hypertension, cardiovascular disease, metabolic disorders, insulin resistance, diabetes, systemic inflammation, major depressive disorder, etc. In another embodiment, PTSD patients having one or more comorbid conditions or diseases may have an improvement in (e.g., reduction, maintain a level, slow a rate of progression of) in the one or more comorbid conditions or diseases. In a particular example, a pre-hypertensive patient (e.g., systolic BP of 120-139 mmHg/ diastolic BP of 80-89 mmHg) may have blood pressure below the pre-hypertensive range after a renal neuromodulation procedure. Likewise, a hypertensive patient (e.g., systolic BP>140 mmHg/diastolic BP>90 mmHg) may have blood pressure below the hypertensive range after a renal neuromodulation procedure. Corresponding results may be obtained with plasma aldosterone concentration, plasma renin activity, and/or aldosterone-to-renin ratio. For example, a reduction in an aldosterone-to-renin ratio can be, for example, by at least about 5%, 10% or a greater amount (e.g., about 50%, about 80%, about 90%) as determined by blood analysis and calculation before and after (e.g., 1, 3, 6, or 12 months after) a renal neuromodulation procedure.

Other measurable physiological parameters may also improve following renal sympathetic neuromodulation. For example, a patient may have an improvement in (e.g., reduction, maintain a level of, slow a rate of progression of) atherosclerosis of extracranial and/or intracranial arteries, clinical measurements of aortic and large-artery, small-vessel disease or other alterations in small arteries providing physiological blood flow, neural activity (e.g., in the amygdala, ventromedial prefrontal cortex, dorsal anterior cingulate cortex, hippocampus and/or insular cortex), and cerebral atrophy (e.g., hippocampal volume reduction, ventromedial prefrontal cortex), following a renal neuromodulation procedure as determined by qualitative or quantitative analysis (e.g., CT scan, PWV analysis, angiography, MM, PET scan, etc.) before and after (e.g., 1, 3, 6, or 12 months after; 2, 3, 4, 5 or 10 years after) a renal neuromodulation procedure. In a particular example, hippocampal volume can be increased (e.g., hippocampal growth) at least about 5%, about 10%, about 15%, about 20%, about 30%, or a greater amount in the patient within about three months to about 12 months after at least partially inhibiting sympathetic neural activity in nerves proximate a renal artery of the kidney.

As discussed previously, the development of PTSD and/or acute stress disorder in certain individuals following a qualifying traumatic event may be related to sympathetic overactivity either before (e.g., chronic or episodic), during (e.g., at the time of), or following the traumatic event and, correspondingly, the degree of sympathoexcitation in a patient may be related to one or more of the severity of the clinical presentation of PTSD, the number of traumatic events experienced by the patient, the age of the patient at the time of the first traumatic exposure, among other psychological, physiological and genetic/epigenetic factors. The kidneys are positioned to be both a cause (via afferent nerve fibers) and a target (via efferent sympathetic nerves) of elevated central sympathetic drive. In some embodiments, renal neuromodulation can be used to reduce central sympathetic drive in a patient demonstrating one or more risk factors for PTSD in a manner that treats the patient for PTSD and/or to prevent an incidence of PTSD in the patient in later life. In some embodiments, for example, MSNA can be reduced by at least about 10% in the patient within about three months after at least partially inhibiting sympathetic neural activity in nerves proximate a renal artery of the kidney. Similarly, in some instances whole body norepinephrine spillover to plasma can be reduced at least about 20%, about 30%, about 40%, about 45%, about 50% or a greater amount in the patient within about three months to about 12 months after at least partially inhibiting sympathetic neural activity in nerves proximate a renal artery of the kidney. Additionally, measured norepinephrine content (e.g., assessed via renal biopsy, assessed in real-time via intravascular blood collection techniques, assessed in real-time via urine, etc.) can be reduced (e.g., at least about 5%, 10%, or by at least 20%) in the patient within about three months after at least partially inhibiting sympathetic neural activity in nerves proximate a renal artery innervating the kidney.

In one prophetic example, a patient having one or more suspected risk factors for PTSD and/or the development of PTSD can be subjected to a baseline assessment indicating a first set of measurable parameters corresponding to the one or more risk factors. Such parameters can include, for example, levels of central sympathetic drive (e.g., MSNA, whole body norepinephrine spillover), measured norepinephrine content (e.g., assessed via tissue biopsy, plasma or urine), blood pressure, 24-hour blood pressure variability, heart rate variability, baroreceptor sensitivity, heart rate during stress/stimuli, skin conductance, glucocorticoid levels (e.g., in hair, urine, plasma, etc.), glucocorticoid sensitivity, number of glucocorticoid receptors (e.g., on peripheral blood lymphocytes), inflammatory biomarker levels (e.g., IL-6, CRP), cholesterol levels, blood glucose levels, fasting blood insulin levels, measures of insulin sensitivity, body mass index, perceived cognitive functioning level (e.g., self-reporting, third-party reporting, etc.), one or more brain function test scores, and brain/body imaging for vascular remodeling (e.g., arteriole stiffness, arterial blood flow) and/or brain structural alterations (e.g., atrophy, neural activity, etc.). Following baseline assessment, the patient can be subjected to a renal neuromodulation procedure. Such a procedure can, for example, include any of the treatment modalities described herein or another treatment modality in accordance with the present technology. The treatment can be performed on nerves proximate one or both kidneys of the patient. Following the treatment (e.g., 1, 3, 6, or 12 months following the treatment; 2, 3, 4, 5 or 10 years following the treatment), the patient can be subjected to a follow-up assessment. The follow-up assessment can indicate a measurable improvement in one or more physiological parameters corresponding to the one or more suspected risk factors for PTSD or the development of PTSD and/or other stress disorder (e.g., acute stress disorder).

The methods described herein address the sympathetic excess that is thought to be an underlying factor in PTSD progression or a central mechanism through which multiple PTSD risk factors are manifest in patients. Currently, there are no therapies prescribed to address the effects of sympathetic excess in patients suspected of having PTSD or a risk of developing PTSD. Certain proposed therapies, such as lifestyle alterations (e.g., exercise, diet, etc.), cognitive behavioral therapy, blood pressure maintenance (e.g., administration of anti-hypertensive therapies), anti-depression and/or anti-anxiety medications, and reduction and/or maintenance of cholesterol have significant limitations including limited efficacy, undesirable side effects and may be subject to adverse or undesirable drug interactions when used in combination. Moreover, use of any drug regimens (e.g., anti-hypertensive, antidepressant, anti-anxiety, cholesterol-lowering, anti-inflammatory, etc.) can have many challenges, including drug contraindications and drug adherence (particularly prior to onset of symptoms). For example, many of these drug regimens may require the patient to remain compliant with the treatment regimen starting in early life (e.g., prior to on-set of PTSD diagnosis) and continue compliance over time. In contrast, neuromodulation can be a one-time or otherwise limited treatment that would be expected to have durable benefits to treat PTSD, reduce severity of PTSD and/or inhibit the long-term potential of developing PTSD and thereby achieve a favorable patient outcome.

In some embodiments, patients demonstrating one or more risk factors associated with PTSD or the development of PTSD and/or have one or more physiological indicators of acute distress disorder (e.g., combined with additional risk factors) can be treated with renal neuromodulation alone. However, in other embodiments, combinations of therapies can be tailored based on specific conditions and PTSD risk factors in a particular patient. For example, certain patients can be treated with combinations of therapies such as one or more conventional therapies for treating depression or anxiety, for treating sleep disorders, and/or reducing blood pressure (e.g., anti-hypertensive drug(s)) and treated with one or more neuromodulation treatments. In another example, renal neuromodulation can be combined with cholesterol lowering agents (e.g., statins), anti-inflammatory therapy (e.g., drug(s)), as well as weight loss and lifestyle change recommendations/programs. In certain embodiments, a patient being treated with one or more pharmaceutical drugs for the PTSD and/or conditions associated with the PTSD can be treated with renal sympathetic neuromodulation to reduce at least one of number of or a measured dosage of the pharmaceutical drugs administered to the patient.

Treatment of PTSD risk factors, acute stress disorder, or symptoms and conditions associated with PTSD may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

IV. Selected Examples of Neuromodulation Modalities

As noted previously, complete or partial neuromodulation of a target renal sympathetic nerve in accordance with embodiments of the present technology can be electrically-induced, thermally-induced, chemically-induced, or induced in another suitable manner or combination of manners at one or more suitable locations along one or more renal blood vessels during a treatment procedure. For example, neuromodulation may be achieved using various modalities, including for example monopolar or bipolar RF energy, pulsed RF energy, microwave energy, laser light or optical energy, magnetic energy, ultrasound energy (e.g., intravascularly delivered ultrasound, extracorporeal ultrasound, high-intensity focused ultrasound (HIFU)), direct heat energy, radiation (e.g., infrared, visible, gamma), or cryotherapeutic energy, chemicals (e.g., drugs or other agents), or combinations thereof. Where a system uses a monopolar configuration, a return electrode or ground patch fixed externally on the subject can be used. In certain embodiments, neuromodulation may utilize one or more devices including, for example, catheter devices such as the Symplicity™ catheter (Medtronic, Inc.). Other suitable thermal devices are described in U.S. Pat. Nos. 7,653,438, 8,347, 891, and U.S. patent application Ser. No. 13/279,205, filed Oct. 21, 2011. Other suitable devices and technologies are described in U.S. patent application Ser. No. 13/279,330, filed Oct. 23, 2011, International Patent Application No. PCT/US2015/021835, filed Mar. 20, 2015, and International Patent Application No. PCT/US2015/013029, filed Jan. 27, 2015. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and U.S. Pat. No. 8,888,773. Other examples of suitable direct heat devices are described in International Patent Application No. PCT/US2014/023738 filed Mar. 11, 2014, and U.S. patent application Ser. No. 14/203,933, filed Mar. 11, 2014. All of the foregoing patent references are incorporated herein by reference in their entireties.

In those embodiments of the methods disclosed herein that utilize partial ablation, the level of energy delivered to the target artery and surrounding tissue may be different than the level that is normally delivered for complete neuromodulation. For example, partial neuromodulation using RF energy may use alternate algorithms or different power levels than RF energy for complete neuromodulation. Alternatively, partial neuromodulation methods may utilize the same level of energy, but delivered to a different depth within the tissue or to a more limited area. In certain embodiments, partial neuromodulation may be achieved using a device that differs from a device used for complete neuromodulation. In certain embodiments, a particular treatment or energy modality may be more suitable for partial neuromodulation than other treatment or energy modalities. In some embodiments, neuromodulation may be achieved using one or more chemical agents, such as by drug delivery. In those embodiments that utilize partial neuromodulation, the methods may utilize the same devices and/or drug delivery systems used for complete neuromodulation, or they may use completely different devices for energy and/or drug delivery.

Thermal effects can include both thermal ablation and non-ablative thermal alteration or damage (e.g., via sustained heating and/or resistive heating) to partially or completely disrupt the ability of a nerve to transmit a signal. Such thermal effects can include the heating effects associated with electrode-based or transducer-based treatment. For example, a treatment procedure can include raising the temperature of target neural fibers to a target temperature above a first threshold to achieve non-ablative alteration, or above a second, higher threshold to achieve ablation. In some embodiments, the target temperature can be higher than about body temperature (e.g., about 37° C.) but less than about 45° C. for non-ablative alteration, and the target temperature can be higher than about 45° C. for ablation. More specifically, heating tissue to a temperature between about body temperature and about 45° C. can induce non-ablative alteration, for example, via moderate heating of target neural fibers or vascular/luminal structures that perfuse the target neural fibers. In cases where vascular structures are affected, the target neural fibers can be denied perfusion resulting in necrosis of the neural tissue. For example, this may induce non-ablative thermal alteration in the fibers or structures. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, complete or partial neuromodulation of a renal sympathetic nerve can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic nerve can slow or potentially block conduction of neural signals to produce a prolonged or permanent reduction in sympathetic activity. A variety of suitable types of energy, such as those mentioned above, can be used to stimulate and/or heat tissue at a treatment location. In some embodiments, neuromodulation can be conducted in conjunction with one or more other tissue modulation procedures. An element, transducer, or electrode used to deliver this energy can be used alone or with other elements, transducers, or electrodes in a multi-element array. Furthermore, the energy can be applied from within the body (e.g., within the vasculature or other body lumens in a catheter-based approach or outside the vasculature using, for example, a Natural Orifice Transluminal Endoscopic Surgery or NOTES procedure) and/or from outside the body, e.g., via an applicator positioned outside the body. In some embodiments, energy can be used to reduce damage to non-targeted tissue when targeted tissue adjacent to the non-targeted tissue is subjected to neuromodulating cooling.

As an alternative to or in conjunction with electrode-based or transducer-based approaches, other suitable energy delivery techniques, such as a cryotherapeutic treatment modality, can be used for achieving therapeutically-effective neuromodulation of a target sympathetic nerve. For example, cryotherapeutic treatment can include cooling tissue at a treatment location in a manner that modulates neural function. For example, sufficiently cooling at least a portion of a target sympathetic nerve can slow or potentially block conduction of neural signals to produce a prolonged or permanent reduction in sympathetic activity associated with the target sympathetic nerve. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death, e.g., during tissue thawing and subsequent hyperperfusion.

Neuromodulation using a cryotherapeutic treatment in accordance with embodiments of the present technology can include cooling a structure proximate an inner surface of a vessel or chamber wall such that tissue is effectively cooled to a depth where sympathetic nerves reside. For example, a cooling assembly of a cryotherapeutic device can be cooled to the extent that it causes therapeutically-effective, cryogenic neuromodulation. In some embodiments, a cryotherapeutic treatment modality can include cooling that is not configured to cause neuromodulation. For example, the cooling can be at or above cryogenic temperatures and can be used to control neuromodulation via another treatment modality, e.g., to protect tissue from neuromodulating energy. Other suitable cryotherapeutic devices are described, for example, in U.S. patent application Ser. No. 13/279,330, filed Oct. 23, 2011, and incorporated herein by reference in its entirety.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause organs and tissues to rise and fall and thereby move the arteries and other structures associated with these organs and tissues. In addition, blood flow is pulsatile and can cause structures associated with the kidneys to pulse. Cryogenic adhesion also can facilitate intravascular or intraluminal positioning, particularly in relatively-small structures (e.g., renal branch arteries) in which stable intravascular or intraluminal positioning can be difficult to achieve.

The use of ultrasound energy can be beneficial in certain embodiments. Focused ultrasound is an example of a transducer-based treatment modality that can be delivered from outside the body (i.e., extracorporeal). In some embodiments, focused ultrasound treatment can be performed in close association with imaging, e.g., magnetic resonance, computed tomography, fluoroscopy, ultrasound (e.g., intravascular or intraluminal), optical coherence tomography, or another suitable imaging modality. For example, imaging can be used to identify an anatomical position of a treatment location, e.g., as a set of coordinates relative to a reference point. The coordinates can then be entered into a focused ultrasound device configured to change the distance from source to target, power, angle, phase, or other suitable parameters to generate an ultrasound focal zone at the location corresponding to the coordinates. In some embodiments, the focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight). In certain embodiments, the ultrasound device may be a catheter device with an ultrasound transducer or an array of ultrasound transducers on its distal tip. In other embodiments the ultrasound device may comprise a cylindrical transducer. In certain embodiments wherein the ultrasound device is being used to perform partial ablation, the device may include discrete and/or forward-facing transducers that can be rotated and inserted at specific conditions, thereby allowing for more discrete lesion formation. In other embodiments, however, the extracorporeal and/or intravascular ultrasound devices may have different arrangements and/or different features.

In some embodiments, neuromodulation can be effected using a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. In some embodiments, the chemical can be guanethidine, vincristine, ethanol, phenol, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more needles originating outside the body or within the vasculature or other body lumens (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

Renal neuromodulation in conjunction with the methods and devices disclosed herein may be carried out at a location proximate (e.g., at or near) a vessel or chamber wall (e.g., a wall of a renal artery, one or more branch vessels from the renal artery, a ureter, a renal pelvis, a major renal calyx, a minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery.

In certain embodiments, monitoring, assessing and/or determining neuromodulation efficacy can be accomplished by detecting changes in the level of one or more surrogate biomarkers (e.g., a biomarker that directly or indirectly correlates with sympathetic nerve activity in the patient, a biomarker that directly or indirectly correlates with hypertension, arterial stiffness and/or an inflammatory response in the patient) in serum, plasma and/or urine in response to neuromodulation. Systems and method for monitoring the efficacy of neuromodulation by measuring the levels of one or more biomarkers associated with neuromodulation including, for example, proteins or non-protein molecules that exhibit an increase or decrease in level or activity in response to neuromodulation are described in, e.g., International Patent Application No. PCT/US2013/030041, filed Mar. 8, 2013, and International Patent Application No. PCT/US2015/047568, filed Aug. 28, 2015, the disclosures of which are incorporated herein by reference in their entireties. In other embodiments, measured levels of protein or non-protein molecules (e.g., associated with norepinephrine spillover, associated with inflammatory responses, etc.) that exhibit an increase or decrease in level or activity in response to targeted neuromodulation can be assessed pre- and post-neuromodulation in tissue biopsies.

V. Selected Embodiments of Renal Neuromodulation Systems and Devices

Figure 4:
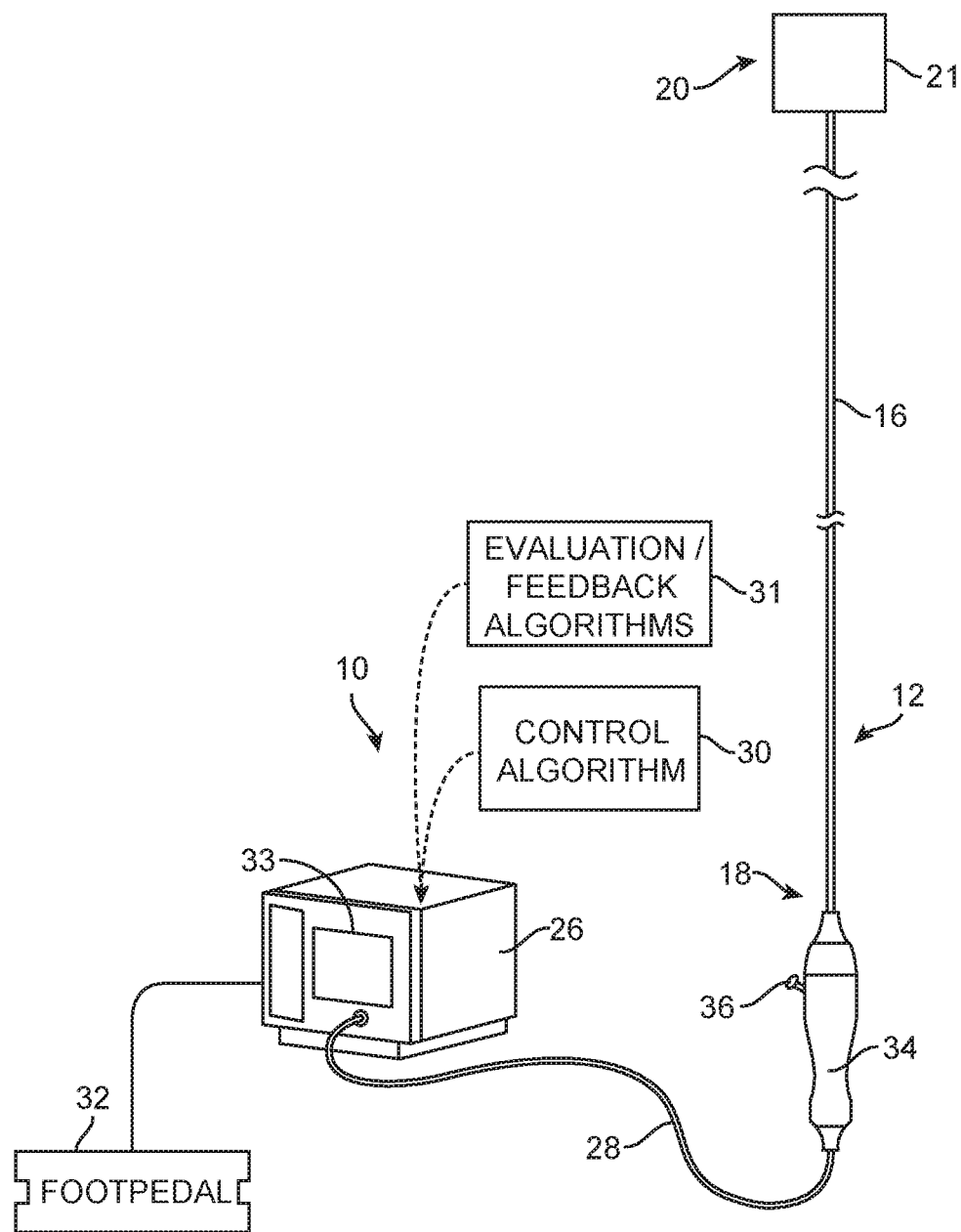
FIG. 4 illustrates an intravascular neuromodulation system configured in accordance with an embodiment of the present technology.

FIG. 4 illustrates a renal neuromodulation system 10 configured in accordance with an embodiment of the present technology. The system 10, for example, may be used to perform therapeutically-effective renal neuromodulation on a patient (a) to reduce the risk of occurrence of PTSD and/or other related conditions (e.g., generalized anxiety disorder, panic attacks), (b) to reduce a calculated PTSD risk score corresponding to a PTSD status, (c) to reduce a severity of neurological symptoms relating to PTSD, and/or (d) to treat and/or prevent development of one or more comorbid conditions/diseases associated with PTSD (e.g., hypertension, cardiovascular disease, metabolic disorders, insulin resistance, diabetes, systemic inflammation, major depressive disorder, etc.). In one embodiment, the patient may be diagnosed with increased overall sympathetic activity, and, in particular, conditions associated with central sympathetic overstimulation and increased risk of developing PTSD following a qualifying traumatic event, such as hypertension, blood pressure variability, systemic inflammation, sleep disorders, anxiety and panic disorders, cardiovascular disease, obesity, metabolic syndrome, insulin resistance and diabetes, among others.

The system 10 includes an intravascular treatment device 12 operably coupled to an energy source or console 26 (e.g., a RF energy generator, a cryotherapy console). In the embodiment shown in FIG. 4, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a neuromodulation assembly or treatment section 21 at the distal portion 20 of the shaft 16. The neuromodulation assembly 21 can be configured to ablate nerve tissue and/or for monitoring one or more physiological parameters within the vasculature. Accordingly, a neuromodulation assembly 21 suitable for ablation may include one or more electrodes, transducers, energy-delivery elements or cryotherapeutic cooling assemblies. Neuromodulation assemblies 21 suitable for monitoring may also include a nerve monitoring device and/or blood collection/analysis device. In some embodiments, the neuromodulation assembly 21 can be configured to be delivered to a renal blood vessel (e.g., a renal artery) in a low-profile configuration.

In one embodiment, for example, the neuromodulation assembly 21 can include a single electrode. In other embodiments, the neuromodulation assembly 21 may comprise a basket and a plurality of electrodes carried by the basket. The electrodes on the basket may be spaced apart from each other such that each electrode is approximately 90° apart from a neighboring electrode. In yet another embodiment, the neuromodulation assembly 21 can include a balloon and a plurality of bipolar electrodes carried by the balloon. In still another embodiment, the neuromodulation assembly 21 has a plurality of electrodes arranged along an elongated member transformable between a low-profile, delivery configuration (e.g., contained in a delivery catheter) and an expanded, deployed configuration in which the elongated member has a helical/spiral shape. In further embodiments, the neuromodulation assembly 21 can include one or more electrodes configured to deliver ablation energy and/or stimulation energy. In some arrangements, the neuromodulation assembly 21 can include one or more sensor(s) for detecting impedance or nerve monitoring signals. In any of the foregoing embodiments, the neuromodulation assembly 21 may comprise an irrigated electrode.

Upon delivery to a target treatment site within a renal blood vessel, the neuromodulation assembly 21 can be further configured to be deployed into a treatment state or arrangement for delivering energy at the treatment site and providing therapeutically-effective electrically-induced and/or thermally-induced renal neuromodulation. In some embodiments, the neuromodulation assembly 21 may be placed or transformed into the deployed state or arrangement via remote actuation, e.g., via an actuator 36, such as a knob, pin, or lever carried by the handle 34. In other embodiments, however, the neuromodulation assembly 21 may be transformed between the delivery and deployed states using other suitable mechanisms or techniques.

The proximal end of the neuromodulation assembly 21 can be carried by or affixed to the distal portion 20 of the elongated shaft 16. A distal end of the neuromodulation assembly 21 may terminate with, for example, an atraumatic rounded tip or cap. Alternatively, the distal end of the neuromodulation assembly 21 may be configured to engage another element of the system 10 or treatment device 12. For example, the distal end of the neuromodulation assembly 21 may define a passageway for engaging a guide wire (not shown) for delivery of the treatment device using over-the-wire ("OTW") or rapid exchange ("RX") techniques. The treatment device 12 can also be a steerable or non-steerable catheter device (e.g., a guide catheter) configured for use without a guide wire. Body lumens (e.g., ducts or internal chambers) can be treated, for example, by non-percutaneously passing the shaft 16 and neuromodulation assembly 21 through externally accessible passages of the body or other suitable methods.

The console 26 can be configured to generate a selected form and magnitude of energy for delivery to the target treatment site via the neuromodulation assembly 21. A control mechanism, such as a foot pedal 32, may be connected (e.g., pneumatically connected or electrically connected) to the console 26 to allow an operator to initiate, terminate and, optionally, adjust various operational characteristics of the console 26, including, but not limited to, power delivery. The system 10 may also include a remote control device (not shown) that can be positioned in a sterile field and operably coupled to the neuromodulation assembly 21. The remote control device can be configured to allow for selective activation of the neuromodulation assembly 21. In other embodiments, the remote control device may be built into the handle assembly 34. The console 26 can be configured to deliver the treatment energy via an automated control algorithm 30 and/or under the control of the clinician. In addition, the console 26 may include one or more evaluation and/or feedback algorithms 31 to provide feedback to the clinician before, during, and/or after therapy.

The console 26 can further include a device or monitor that may include processing circuitry, such as a microprocessor, and a display 33. The processing circuitry may be configured to execute stored instructions relating to the control algorithm 30. The console 26 may be configured to communicate with the treatment device 12 (e.g., via a cable 28) to control the neuromodulation assembly and/or to send signals to or receive signals from the nerve monitoring device. The display 33 may be configured to provide indications of power levels or sensor data, such as audio, visual or other indications, or may be configured to communicate information to another device. For example, the console 26 may also be configured to be operably coupled to a catheter lab screen or system for displaying treatment information, such as nerve activity before and/or after treatment.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or balloon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

VI. Selected Examples of Treatment Procedures for Renal Neuromodulation

A. Achieving Intravascular Access to the Renal Artery

Figures 5A, 5B:
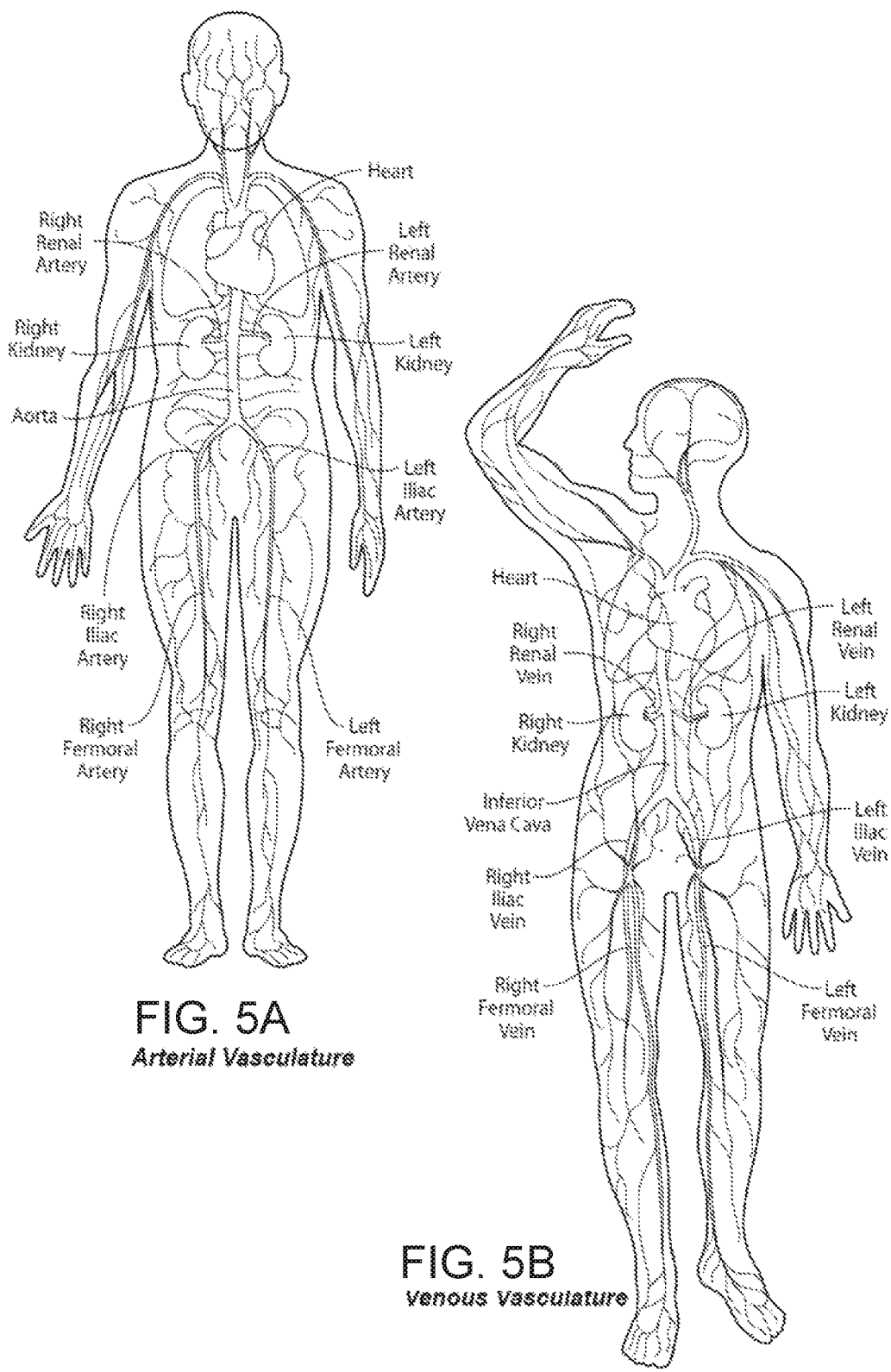
FIGS. 5A and 5B are anatomic views of the arterial vasculature and venous vasculature, respectively, of a human.

In accordance with the present technology, neuromodulation of a left and/or right renal plexus RP, which is intimately associated with a left and/or right renal artery, may be achieved through intravascular access. As FIG. 5A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 5B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This route comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

B. Properties and Characteristics of the Renal Vasculature

Properties and characteristics of the renal vasculature impose challenges to both access and treatment methods, and to system/device designs. Since neuromodulation of a left and/or right renal plexus RP may be achieved in accordance with embodiments of the present technology through intravascular access, various aspects of the design of apparatus, systems, and methods for achieving such renal neuromodulation are disclosed herein. Aspects of the technology disclosed herein address additional challenges associated with variation of physiological conditions and architecture across the patient population and/or within a specific patient across time, as well as in response to disease states, such as hypertension, atherosclerosis, vascular disease, chronic inflammatory condition, insulin resistance, diabetes, metabolic syndrome, etc. For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access can account for these and other aspects of renal arterial anatomy and its variation across the patient population when minimally invasively accessing a renal artery. For example, spiral or helical CT technology can be used to produce 3D images of the vascular features for individual patients, and intravascular path choice as well as device size/diameter, length, flexibility, etc. can be selected based upon the patient's specific vascular features.

In addition to complicating renal arterial access, specifics of the renal anatomy also complicate establishment of stable contact between neuromodulatory apparatus and a luminal surface or wall of a renal blood vessel. When the neuromodulatory apparatus includes an energy delivery element, such as an electrode, transducer, or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within a renal artery RA, as well as tortuosity of the artery. Furthermore, establishing consistent contact can be complicated by patient movement, respiration, and/or the cardiac cycle because these factors may cause significant movement of the renal artery RA relative to the aorta, and the cardiac cycle may transiently distend the renal artery RA (i.e., cause the wall of the artery to pulse). To address these challenges, the treatment device or applicator may be designed with relative sizing and flexibility considerations. For example, the renal artery may have an internal diameter in a range of about 2-10 mm and the treatment device can be delivered using a 3, 4, 5, 6, 7 French, or in some cases, an 8 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a renal artery and facilitating stable contact between neuromodulatory apparatus and a luminal surface of the artery, nerves in and around the adventitia of the artery can be modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant (e.g., 1-3 mm) from the luminal surface of the artery. Sufficient energy can be delivered to or heat removed from the target renal nerves to modulate the target renal nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause a kidney infarct, thereby causing irreversible damage to the kidney, thermal treatment from within the renal artery RA can be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery. Accordingly, sensory feedback, such as impedance and temperature, can be used to assess whether a desired energy distribution is administered at the treatment site and can, in some instances, be used to change an energy delivery algorithm in real-time to adjust for varying fluctuations in the properties and conditions affecting heat transfer dynamics at the treatment site.

The neuromodulatory apparatus can also be configured to allow for adjustable positioning and repositioning of an energy delivery element or a cryotherapeutic device, within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the cryotherapeutic devices or energy delivery elements and/or repositioning of the neuromodulatory apparatus to multiple treatment locations may be desirable. It should be noted, however, that a benefit of creating a circumferential lesion or ablation may outweigh the potential of renal artery stenosis or the risk may be mitigated with certain embodiments or in certain patients and creating a circumferential lesion or ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion, for example to 2-5 minutes.

C. Neuromodulation of Renal Sympathetic Nerve at Treatment Site

Figure 6:
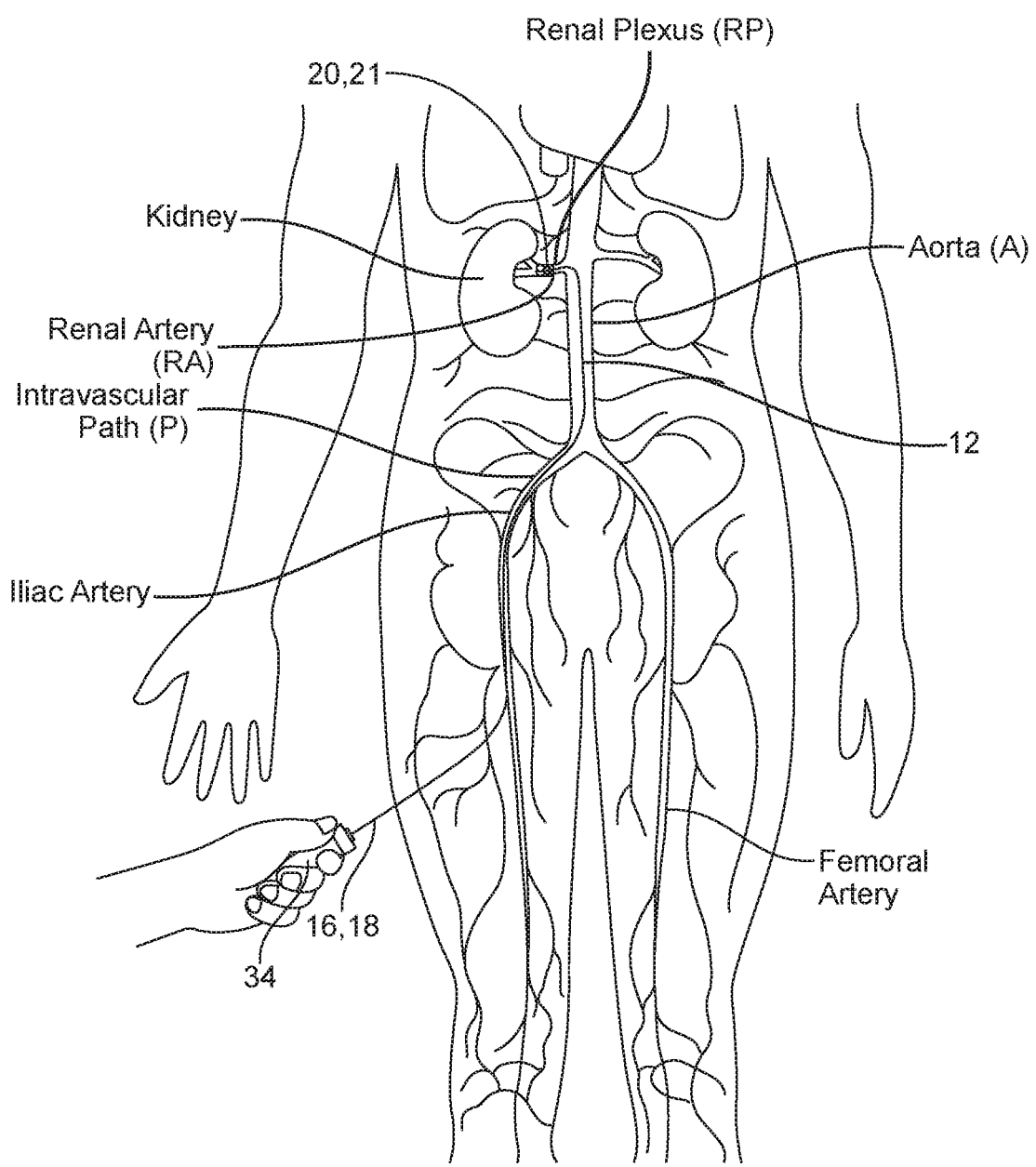
FIG. 6 illustrates modulating renal nerves with a neuromodulation system configured in accordance with an embodiment of the present technology.

FIG. 6 illustrates modulating renal nerves with an embodiment of the system 10 (FIG. 4). The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., CT, fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12. In some embodiments, the shaft 16 and the neuromodulation assembly 21 can be 3, 4, 5, 6, or 7 French or another suitable size. Furthermore, the shaft 16 and the neuromodulation assembly 21 can be partially or fully radiopaque and/or can include radiopaque markers corresponding to measurements, e.g., every 5 cm.

After the neuromodulation assembly 21 is adequately positioned in the renal artery RA, it can be radially expanded or otherwise deployed using the handle 34 or other suitable control mechanism until the neuromodulation assembly is positioned at its target site and in stable contact with the inner wall of the renal artery RA. The purposeful application of energy from the neuromodulation assembly can then be applied to tissue to induce one or more desired neuromodulating effects on localized regions of the renal artery RA and adjacent regions of the renal plexus RP, which lay intimately within, adjacent to, or in close proximity to the adventitia of the renal artery RA. The neuromodulating effects may include denervation, thermal ablation, and non-ablative thermal alteration or damage (e.g., via sustained heating and/or resistive heating). The purposeful application of the energy may achieve neuromodulation along all or at least a portion of the renal plexus RP.

In the deployed state, the neuromodulation assembly 21 can be configured to contact an inner wall of a vessel of the renal vasculature and to form a suitable lesion or pattern of lesions without the need for repositioning. For example, the neuromodulation assembly 21 can be configured to form a single lesion or a series of lesions, e.g., overlapping and/or non-overlapping. In some embodiments, the lesion(s) (e.g., pattern of lesions) can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the neuromodulation assembly 21 can be configured form a partially-circumferential lesion or a fully-circumferential lesion at a single longitudinal segment or zone of the vessel. During treatment, the neuromodulation assembly 21 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the neuromodulation assembly 21 can be configured to cause therapeutically-effective neuromodulation (e.g., using ultrasound energy) without contacting a vessel wall.

As mentioned previously, the methods disclosed herein may use a variety of suitable energy modalities, including RF energy, pulsed RF energy, microwave energy, laser, optical energy, ultrasound energy (e.g., intravascularly delivered ultrasound, extracorporeal ultrasound, HIFU), magnetic energy, direct heat, cryotherapy, radiation (e.g., infrared, visible, gamma), or a combination thereof. Alternatively or in addition to these techniques, the methods may utilize one or more non-ablative neuromodulatory techniques. For example, the methods may utilize non-ablative SNS neuromodulation by removal of target nerves (e.g., surgically), injection of target nerves with a destructive drug or pharmaceutical compound, or treatment of the target nerves with non-ablative energy modalities (e.g., laser or light energy). In certain embodiments, the amount of reduction of the sympathetic nerve activity may vary depending on the specific technique being used.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

Furthermore, a treatment procedure can include treatment at any suitable number of treatment locations, e.g., a single treatment location, two treatment locations, or more than two treatment locations. In some embodiments, different treatment locations can correspond to different portions of the renal artery RA, the renal vein, and/or other suitable structures proximate tissue having relatively high concentrations of renal nerves. The shaft 16 can be steerable (e.g., via one or more pull wires, a steerable guide or sheath catheter, etc.) and can be configured to move the neuromodulation assembly 21 between treatment locations. At each treatment location, the neuromodulation assembly 21 can be activated to cause modulation of nerves proximate the treatment location. Activating the neuromodulation assembly 21 can include, for example, heating, cooling, stimulating, or applying another suitable treatment modality at the treatment location. Activating the neuromodulation assembly 21 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the neuromodulation assembly 21 can be configured to introduce (e.g., inject) a chemical (e.g., a drug or other agent) into target tissue at the treatment location. Such chemicals or agents can be applied at various concentrations depending on treatment location and the relative depth of the target nerves.

As discussed, the neuromodulation assembly 21 can be positioned at a treatment location within the renal artery RA, for example, via a catheterization path including a femoral artery and the aorta, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The neuromodulation assembly 21 can be configured to accommodate the anatomy of the renal artery RA, the renal vein, and/or another suitable structure. For example, the neuromodulation assembly 21 can include a balloon (not shown) configured to inflate to a size generally corresponding to the internal size of the renal artery RA, the renal vein, and/or another suitable structure. In some embodiments, the neuromodulation assembly 21 can be an implantable device and a treatment procedure can include locating the neuromodulation assembly 21 at the treatment location using the shaft 16 fixing the neuromodulation assembly 21 at the treatment location, separating the neuromodulation assembly 21 from the shaft 16, and withdrawing the shaft 16. Other treatment procedures for modulation of renal nerves in accordance with embodiments of the present technology are also possible.

Figure 7:
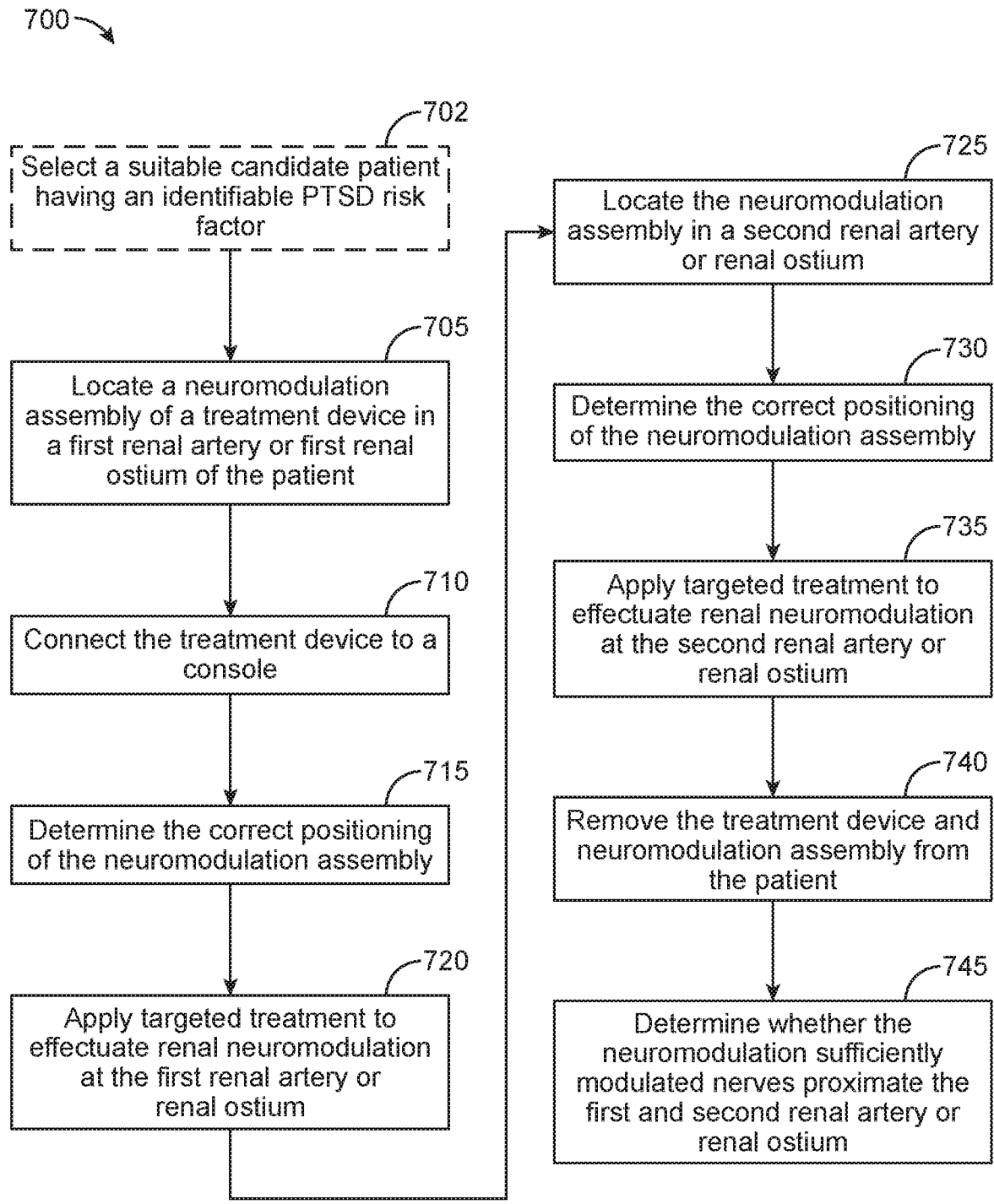
FIG. 7 is a block diagram illustrating a method of modulating renal nerves in accordance with an embodiment of the present technology.

FIG. 7 is a block diagram illustrating a method 700 of modulating renal nerves using the system 10 described above with reference to FIGS. 4 and 6. With reference to FIGS. 4, 6 and 7 together, the method 700 can optionally include selecting a suitable candidate patient having an identifiable PTSD risk factor for performing renal neuromodulation (block 702). For example, a suitable patient can include a patient having a PTSD risk score corresponding to a PTSD status in the patient that is above a threshold level, a patient having one or more measurable risk factors for developing PTSD, a patient having one or more identifiable PTSD symptoms following a traumatic event, a patient diagnosed with PTSD, an at-risk patient having a history of traumatic events and/or a genetic predisposition for developing PTSD, and/or a patient diagnosed with acute stress disorder following a traumatic event and having one or more identifiable risk factors for developing PTSD.

Modulating SNS nerves innervating the kidneys is expected to lower renal nerve activity and/or central SNS nerve activity, thereby inhibiting, preventing, slowing, disrupting or reversing physiological pathways associated with PTSD and/or lowering a risk associated with developing PTSD in the patient either before or after experiencing a qualifying traumatic event. In particular, targeting the renal nerve for neuromodulation is anticipated to reduce renal norepinephrine spillover, whole body norepinephrine spillover, and reduce central sympathetic drive (e.g., reduce a level of efferent SNS nerve firing) in the patient, thereby inhibiting, preventing, slowing, disrupting or reversing PTSD and/or symptoms associated with PTSD and/or conditions proposed to increase a patient's risk of developing PTSD. Without being bound by theory, renal neuromodulation is anticipated to address the hyperactivity of the SNS and/or the elevated SNS tone present in PTSD patients and/or patients having one or more risk factors of developing PTSD. In other instances, and without being bound by theory, an overactive or hyperactive SNS is believed to be an underlying contributing cause of PTSD and renal neuromodulation is anticipated to prevent or prohibit the development of a hyperactive or overactive SNS in a patient prior to or subsequent to experiencing a qualifying traumatic event.

The method 700 can include intravascularly locating the neuromodulation assembly 21 in a delivery state (e.g., low-profile configuration) to a first target site in or near a first renal blood vessel (e.g., first renal artery) or first renal ostium (block 705). The treatment device 12 and/or portions thereof (e.g., the neuromodulation assembly 21) can be inserted into a guide catheter or sheath to facilitate intravascular delivery of the neuromodulation assembly 21. In certain embodiments, for example, the treatment device 12 can be configured to fit within an 8 Fr guide catheter or smaller (e.g., 7 Fr, 6 Fr, etc.) to access small peripheral vessels. A guide wire (not shown) can be used to manipulate and enhance control of the shaft 16 and the neuromodulation assembly 21 (e.g., in an OTW or a RX configuration). In some embodiments, radiopaque markers and/or markings on the treatment device 12 and/or the guide wire can facilitate placement of the neuromodulation assembly 21 at the first target site (e.g., a first renal artery or first renal ostium of the patient). In some embodiments, a contrast material can be delivered distally beyond the neuromodulation assembly 21, and fluoroscopy and/or other suitable imaging techniques can be used to aid in placement of the neuromodulation assembly 21 at the first target site.

The method 700 can further include connecting the treatment device 12 to the console 26 (block 710), and determining whether the neuromodulation assembly 21 is in the correct position at the target site and/or whether the neuromodulation assembly (e.g., electrodes or cryotherapy balloon) is functioning properly (block 715). Once the neuromodulation assembly 21 is properly located at the first target site and no malfunctions are detected, the console 26 can be manipulated to initiate application of an energy field to the target site to cause electrically-induced and/or thermally-induced partial or full denervation of the kidney (e.g., using electrodes or cryotherapeutic devices). Accordingly, heating and/or cooling of the neuromodulation assembly 21 causes modulation of renal nerves at the first target site to cause partial or full denervation of the kidney associated with the first target site (block 720).

In one example, the treatment device 12 can be an RF energy emitting device and RF energy can be delivered through energy delivery elements or electrodes to one or more locations along the inner wall of the first renal blood vessel or first renal ostium for predetermined periods of time (e.g., 120 seconds). In some embodiments, multiple treatments (e.g., 4-6) may be administered in both the left and right renal blood vessels (e.g., renal arteries) to achieve a desired coverage and/or desired inhibition of sympathetic neural activity in the body.

In some embodiments, a treatment procedure can include applying a suitable treatment modality at a treatment location in a testing step (not shown) followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

A technical objective of a treatment may be, for example, to heat tissue to a desired depth (e.g., at least about 3 mm) to a temperature that would lesion a nerve (e.g., about 65° C.). A clinical objective of the procedure typically is to treat (e.g., lesion) a sufficient number of renal nerves (either efferent or afferent nerves) to cause a reduction in sympathetic tone or drive to the kidneys. If the technical objective of a treatment is met (e.g., tissue is heated to about 65° C. to a depth of about 3 mm) the probability of forming a lesion of renal nerve tissue is high. The greater the number of technically successful treatments, the greater the probability of modulating a sufficient proportion of renal nerves, and thus the greater the probability of clinical success.

In a specific example of using RF energy for renal nerve modulation, a clinician can commence treatment which causes the control algorithm 30 (FIG. 4) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In another specific example, the treatment device 12 can be a cryogenic device and cryogenic cooling can be applied for one or more cycles (e.g., for 30 second increments, 60 second increments, 90 second increments, etc.) in one or more locations along the circumference and/or length of the first renal artery or first renal ostium. The cooling cycles can be, for example, fixed periods or can be fully or partially dependent on detected temperatures (e.g., temperatures detected by a thermocouple (not shown) of the neuromodulation assembly 21). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 21 can then be located at a second target site in or near a second renal blood vessel (e.g., second renal artery) or second renal ostium (block 725), and correct positioning of the assembly 21 can be determined (block 730). In selected embodiments, a contrast material can be delivered distally beyond the neuromodulation assembly 21 and fluoroscopy and/or other suitable imaging techniques can be used to locate the second renal artery. The method 700 continues by applying targeted heat or cold to effectuate renal neuromodulation at the second target site to cause partial or full denervation of the kidney associated with the second target site (block 735).

After providing the therapeutically-effective neuromodulation energy (e.g., cryogenic cooling, RF energy, ultrasound energy, etc.), the method 700 may also include removing the treatment device 12 (e.g., catheter) and the neuromodulation assembly 21 from the patient (block 740). In some embodiments, the neuromodulation assembly 21 can be an implantable device (not shown) and a treatment procedure can include implanting the neuromodulation assembly 21 at a suitable treatment location within the patient. Other treatment procedures for modulation of target sympathetic nerves in accordance with embodiments of the present technology are also possible.

The method 700 may also include determining whether the neuromodulation sufficiently modulated nerves or other neural structures proximate the first and second target sites (block 745). For example, the process of determining whether the neuromodulation therapeutically treated the nerves can include determining whether nerves were sufficiently modulated or otherwise disrupted to reduce, suppress, inhibit, block or otherwise affect the afferent and/or efferent renal signals (e.g., by evaluation of suitable biomarkers, stimulation and recording of nerve signals, etc.). Examples of suitable biomarkers and their detection are described in International Patent Application No. PCT/US2013/030041, filed Mar. 8, 2013, and International Patent Application No. PCT/US2015/047568, filed Aug. 28, 2015, the disclosures of which are incorporated herein by reference in their entireties. Other suitable devices and technologies, such as endovascular intraoperative renal nerve monitoring devices are described in International Patent Application No. PCT/US12/63759, filed Jan. 29, 2013, and incorporated herein by reference in its entirety.

In a further embodiment, patient assessment could include determining whether the neuromodulation therapeutically treated the patient for one or more symptoms associated with PTSD, e.g., heightened startle responses, hyperarousal, sleep disturbances, fear memory consolidation and/or conditioning, excessive sweating in response to perceived threat and/or stress, systemic inflammation, and undesirable elevations in heart rate, blood pressure, and skin conductance, among others. Assessment of certain suitable biomarkers and/or nerve signals may be made immediately or shortly after neuromodulation (e.g., about 15 minutes, about 24 hours, or about 7 days post-neuromodulation). In further embodiments, patient assessment could be performed at time intervals (e.g., about 1 month, 3 months, 6 months, 12 months) following neuromodulation treatment. For example, the patient can be assessed for measurements of blood pressure, blood pressure variability (e.g., nocturnal blood pressure "dipping"), heart rate variability, skin conductance, resting heart rate, sleep patterns or quality, measures of sympathetic activity (e.g., MSNA, renal and/or total body norepinephrine spillover, plasma norepinephrine levels, and heart rate variability), peripheral inflammatory markers (e.g., IL-6, CRP, etc.), sodium level, potassium level, plasma aldosterone concentration, plasma renin activity, aldosterone-to-renin ratio, salt suppression, levels of components of the RAAS (e.g., angiotensinogen II levels), urinary $Na^+/K^+$ levels, markers of renal damage or measures of renal function (e.g. creatinine level, estimated glomerular filtration rate, blood urea nitrogen level, creatinine clearance, cystatin-C level, NGAL levels, KIM-1 levels, presence of proteinuria or microalbuminuria, urinary albumin creatinine ratio), and/or a post-neuromodulation PTST risk score (e.g., via a PTSD screening tool for determining a severity of PTSD).

In other embodiments, various steps in the method 700 can be modified, omitted, and/or additional steps may be added. In further embodiments, the method 700 can have a delay between applying therapeutically-effective neuromodulation energy to a first target site at or near a first renal artery or first renal ostium and applying therapeutically-effective neuromodulation energy to a second target site at or near a second renal artery or second renal ostium. For example, neuromodulation of the first renal artery can take place at a first treatment session, and neuromodulation of the second renal artery can take place a second treatment session at a later time.

Figure 8:
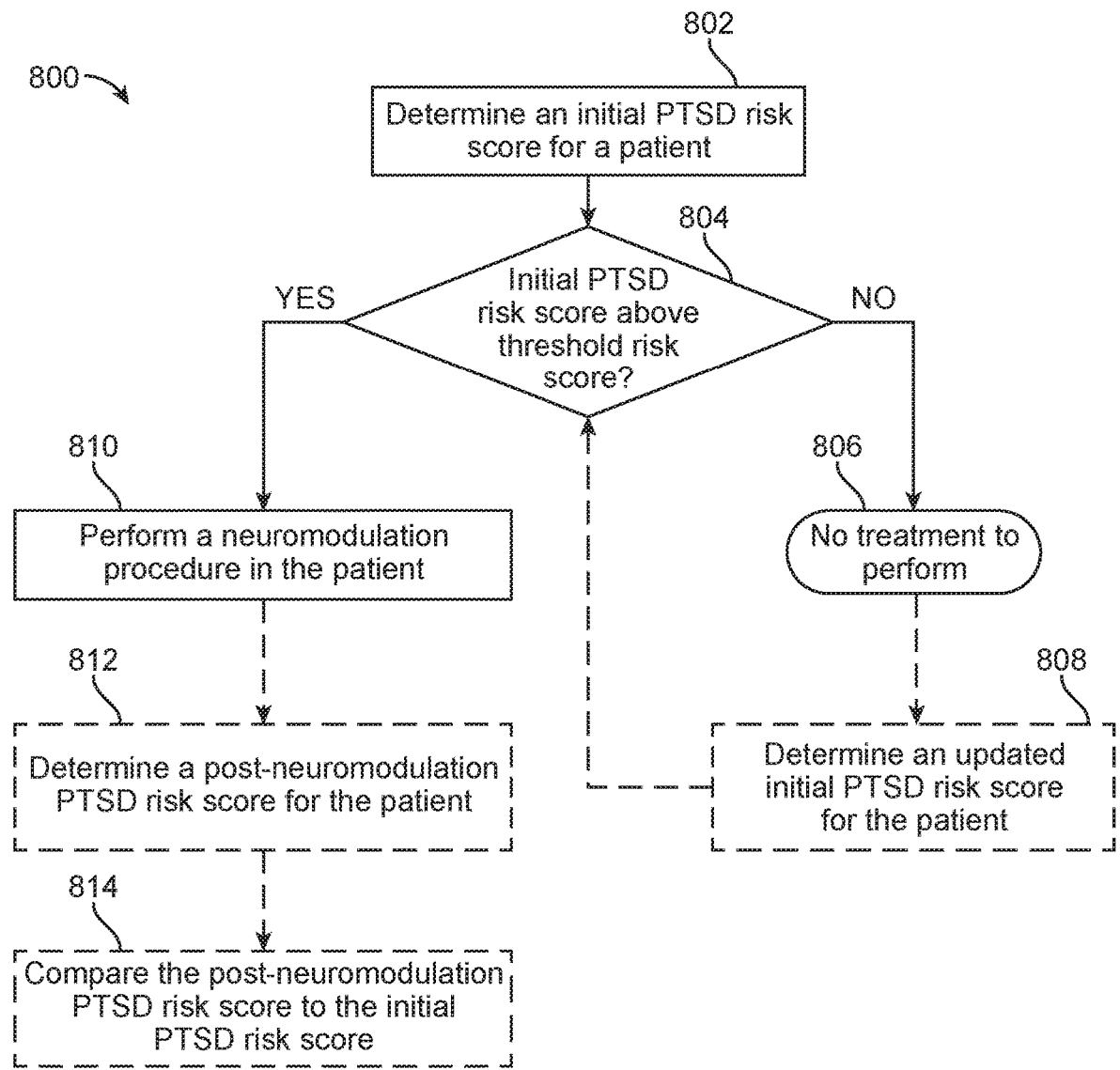
FIG. 8 is a block diagram illustrating a method for improving a PTSD risk score for a patient in accordance with an embodiment of the present technology.

FIG. 8 is a block diagram illustrating a method 800 for improving a PTSD risk score for a patient in accordance with aspects of the present technology. In a first step, the method 800 can include determining an initial PTSD risk score for a patient (block 802). For example, one or more suitable PTSD risk score calculating techniques or tools can be used to establish a PTSD risk score corresponding to a PTSD status in the patient as described above (Boscarino, J. A., et al. *Psychiatry Res.*, 2012, 30: 827-834). At decision block 804, the initial PTSD risk score can be evaluated against a threshold risk score or value. If the initial PTSD risk score is not above the threshold risk score, there is no need to reduce the PTSD risk score for the patient at the current time and no treatment is selected to perform (block 806). In such a patient, a clinician may recommend monitoring the patient's PTSD risk score over time. For example, a clinician can optionally determine an updated initial PTSD risk score for the patient after a determined time lapse (e.g., 1 month, 2 months, 3 months, 6 months, 12 months, etc. following exposure to a traumatic event) (block 808). Following each PTSD risk score evaluation (block 808), the patient PTSD risk score is evaluated against the threshold risk score or value (decision block 804).

If the patient PTSD risk score from method step 802, or from the optional method step 808, is higher than the threshold risk score, the method 800 can include performing a neuromodulation procedure in the patient (block 810). In one example, the patient can be a suitable candidate patient as identified in method step 702 of method 700 described above, and the neuromodulation procedure can be performed as described in continuing steps of method 700. In other embodiments, a clinician can perform an alternative neuromodulation procedure at method step 810. For example, neuromodulation of other target (e.g., non-renal) sympathetic nerves or neuromodulation in a single renal blood vessel (e.g., renal artery) may be performed on the patient.

The method 800 is expected to improve the patient's PTSD risk score or reduce a probability of the patient developing PTSD following a traumatic event. Optionally, the clinician can further determine a post-neuromodulation PTSD risk score for the patient (block 812). For example, the patient can be evaluated using the PTSD risk score tool to assess the patient's post-neuromodulation PTSD status or, alternatively, risk of developing PTSD following the traumatic event or experience. If the post-neuromodulation PTSD risk score is determined for the patient in step 812, the method includes comparing the post-neuromodulation PTSD risk score to the initial PTSD risk score (block 814). In determining if the method 800 is successful, the post-neuromodulation PTSD risk score is lower than the patient's initial PTSD risk score as determined in step 802 (or updated PTSD initial risk score as determined in step 808). In some examples, the post-neuromodulation PTSD risk score is lower than the initial PTSD risk score by about 5%, about 10%, about 20% or about 30%. In other embodiments, the post-neuromodulation PTSD risk score is lower than the initial PTSD risk score by more than 30%. In certain embodiments, the post-neuromodulation PTSD risk score can be lower than the threshold risk score.

VII. Experimental Examples

Example 1

This section describes an example of the outcome of renal neuromodulation on human patients. A total of 45 patients (mean age of 58±9 years) diagnosed with essential hypertension were treated with percutaneous, catheter based renal nerve ablation. Treatment included RF energy delivery to the renal artery using a single-electrode Symplicity Flex™ catheter commercially available from Medtronic, Inc., of 710 Medtronic Parkway, Minneapolis, Minn. 55432-5604. In this human trial, a radiotracer dilution method was used to assess overflow of norepinephrine from the kidneys into circulation before and 15-30 days after the procedure in 10 patients. Bilateral renal-nerve ablation resulted in a marked reduction in mean norepinephrine spillover from both kidneys: 47% (95% confidence interval) one month after treatment.

In a similar human trial where bilateral renal nerve ablation was performed in 70 patients, whole-body norepinephrine levels (i.e., a measure of "total" sympathetic activity), fell by nearly 50% after renal nerve ablation and measurement of muscle sympathetic nerve activity showed a drop of 66% over 6 months, further supporting the conclusion that total sympathetic dive was reduced by the renal denervation procedure in this patient group.

Example 2

Example 2 describes the outcome of catheter-based renal neuromodulation on human patients diagnosed with hypertension. Patients selected having a baseline systolic blood pressure of 160 mm Hg or more (≥150 mm Hg for patients with type 2 diabetes) and taking three or more antihypertensive drugs, were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, $p<0.0001$), whereas they did not differ from baseline in the control group (change of 1/0 mm Hg, baseline of 178/97 mm Hg, $p=0.77$ systolic and $p=0.83$ diastolic). Between-group differences in blood pressure at 6 months were 33/11 mm Hg ($p<0.0001$). At 6 months, 41 (84%) of 49 patients who underwent renal neuromodulation had a reduction in systolic blood pressure of 10 mm Hg or more, compared with 18 (35%) of 51 control patients ($p<0.0001$).

Example 3

Example 3 describes the outcome of catheter-based renal neuromodulation on animal subjects in an additional experiment. In this example (and referring to FIGS. 9A and 9B), studies using the pig model were performed using a multi-electrode Symplicity Spyral™ catheter or a single-electrode Symplicity Flex™ catheter along with a Symplicity G3™ generator. The catheters and generator are commercially available from Medtronic, Inc. The catheters were used in these cohorts of animals (n=66) to create multiple RF ablations in the renal vasculature. Cortical axon density in the renal cortex (FIG. 9A) and renal cortical norepinephrine (NE) concentration (FIG. 9B) were used as markers to measure procedural efficacy.

As shown in FIG. 9A, cortical axon area (per mm$^2$) dropped approximately greater than 54% between a control group (n=64) and treated groups of pigs (n=66) undergoing treatment. For pigs undergoing treatment with the Symplicity Flex™ catheter (n=54), an average of 4.1 lesions were formed in each animal. These pigs demonstrated a 56.9% increase in non-functional axonal area along the renal artery, and a 68% decrease in cortical axon area as compared with the control group. For pigs undergoing treatment with the Symplicity Spyral™ catheter (n=12), an average of 4.0 lesions were formed in each animal. The pigs undergoing treatment with the Symplicity Spyral™ catheter demonstrated a 47.3% increase in non-functional area along the renal artery, and a 54% decrease in cortical axon area relative to the control group. Without being bound by theory, it is believed that the loss of cortical axons is a likely consequence of nerve atrophy distal to the ablation sites.

Figure 9B:
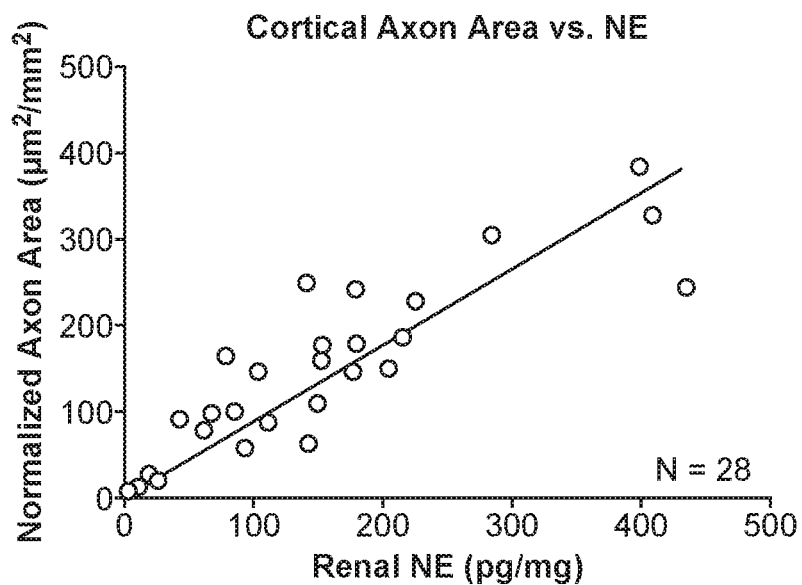
FIG. 9B is a series of graphs illustrating the response correlation between normalized cortical axon area vs. norepinephrine concentration and norepinephrine concentration vs. extent of nerve ablation along the artery of the animal subjects of FIG. 9A.
Figure 9B:
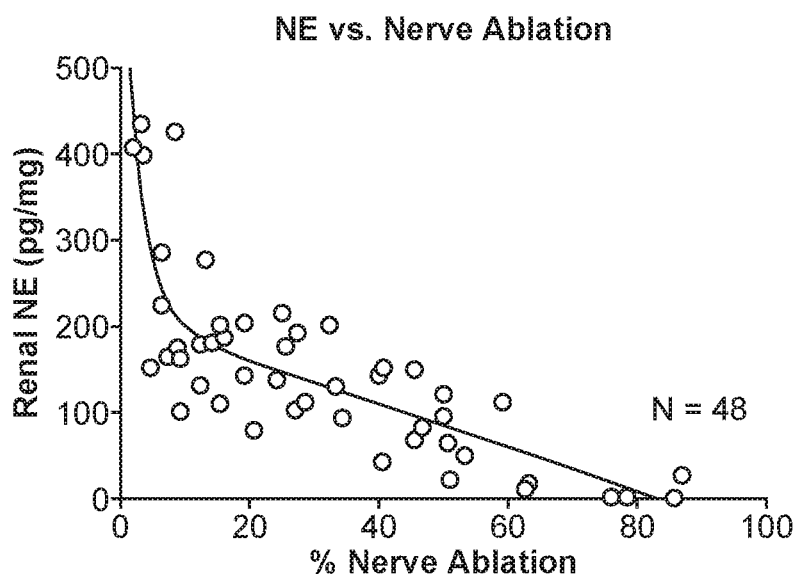

FIG. 9B includes (a) a graph of normalized cortical axon area vs. renal NE concentration, and (b) a graph of renal NE concentration vs. extent (%) of nerve ablation. Referring to the table of FIG. 9A and the two graphs of FIG. 9B together, cortical axon area correlates directly with renal NE. In particular, pigs undergoing treatment with the Symplicity Flex™ catheter exhibited a 65% decrease in mean NE level compared with the pigs in the control group. The pigs treated with the Symplicity Spyral™ catheter exhibited a 68% decrease in mean NE level compared with the pigs in the control group. This is further shown by the first graph of FIG. 9B, which demonstrates that a decrease in cortical axon area correlates with a decrease in NE levels. Referring to the second graph of FIG. 9B, renal NE decrease is non-linear with increased loss of nerve viability along the artery (further extent (%) of nerve ablation). These findings suggest that catheter-based renal neuromodulation exhibits a relatively consistent impact on sympathetic nerve function and viability, and further suggest that neuromodulation of SNS fibers innervating a target tissue and/or organ (such as the kidney) result in a significant decrease in local NE concentration.

Example 4

Example 4 describes an example of the outcome of renal neuromodulation on human patients. Markers of cardiovascular inflammation and remodeling were assessed (Dörr, O., et al., *Clin Res Cardiol*, 2015, 104: 175-184). A total of 60 patients (mean age of 67.9±9.6 years) diagnosed with resistant arterial hypertension were treated with percutaneous, catheter-based renal sympathetic denervation. Treatment included RF energy delivery to the renal artery using a Symplicity® catheter system commercially available from Medtronic, Inc. In this human trial, a therapeutic response was defined as a systolic blood pressure (BP) reduction of >10 mmHg in the office blood pressure measurement 6 months after renal denervation. Of the 60 patients, 49 patients (82%) were classified as responders with a mean systolic BP reduction of >10 mmHg. Venous blood samples for determination of biomarkers of inflammation (e.g., IL-6, high-sensitive C-reactive protein (hsCRP)) and markers of vascular remodeling (matrix metalloproteinases (MMP-2 and MMP-9), tissue inhibitors of matrix metalloproteinases (TIMP-1)) were collected at baseline (prior to renal denervation) and 6 months after renal denervation for all patients.

Collected data from all patients demonstrated that bilateral renal nerve denervation resulted in a significant reduction in mean office systolic BP of 26.4 mmHg (169.3±11.3 mmHg at baseline vs. 142.9±13.8 mmHg at follow-up;

p<0.001). The procedure further resulted in a significant reduction in the serum levels of hsCRP (3.6 mg/dL at baseline vs. 1.7 mg/dL at follow-up, p<0.001), and a significant reduction in the pro-inflammatory cytokine IL-6 (4.04 pg/mL at baseline vs. 2.2 pg/mL at follow-up, p<0.001) six months after treatment. Additionally, the procedure resulted in a significant increase in the serum levels of MMP-9 (425.2 ng/mL at base line vs. 574.1 ng/mL at follow-up, p=0.02), and in serum levels of MMP-2 (192.3 ng/mL at baseline vs. 231.3 ng/mL at follow-up, p<0.001). There were no significant changes in TIMP-1 6 months after renal denervation. Notably, of non-responders (e.g., patients with a BP reduction of <10 mmHg), serum levels of hsCRP still decreased (3.2 mg/dL at baseline vs. 2.4 mg/dL at follow-up, p=0.09), and serum levels of IL-6 still decreased (3.1 pg/mL at baseline vs. 2.7 pg/mL at follow-up, p=0.16), although there was a significantly greater beneficial effect of renal denervation on biomarker levels in BP responders when compared with non-responders.

These findings suggest that catheter-based renal neuromodulation exhibits a positive vascular and systemic effect on mediators of inflammation, IL-6 and hsCRP, and inhibitors (MMP-9 and MMP-2) of deleterious cardiovascular remodeling. Low serum levels of MMP-9 and MMP-2 have been found to be essential to damaging vascular remodeling found in essential hypertension and progression of end-organ damage These findings suggest that levels of MMP-9 and MMP-2, which are involved in ECM turnover in different tissues, including the arterial wall, can be elevated post-renal neuromodulation, and, without being bound by theory, are postulated to be beneficial in reversal of damage to the vessels caused by inflammation, cardiovascular disease and/or hypertension. As elevated inflammatory biomarkers, such as IL-6 and CRP, have been proposed as predictors and possible contributors of PTSD etiology and/or incidence of PTSD, these results demonstrate that renal neuromodulation may be useful to reduce a severity of PTSD, reverse a PTSD diagnosis, or reduce a risk associated with the development of PTSD in a patient following a traumatic event (Michopoulos, V., et al., *Exp Neurol,* 2016, 284: 220-229; Michopoulos, V., et al., *Biol Psychiatry,* 2015, 78(5): 344-353). In addition to lowering systolic BP in (responsive) hypertensive patients, these findings suggest that renal denervation has a positive effect on biomarkers of inflammation (e.g., IL-6, hsCRP) and cardiovascular remodeling (e.g., MMP-2, MMP-9) separate from and in addition to the effect on blood pressure.

Example 5

Example 5 describes an example of the effects of renal neuromodulation on nocturnal blood pressure using ambulatory 24-hour blood pressure (BP) monitoring in human patients. Elevated blood pressure during the nighttime as well early morning hours is associated with an increased risk of cardiovascular events and strokes, and "non-dipping" nocturnal blood pressure is associated with more PTSD hyperarousal symptoms, poorer overall sleep quality, more frequent use of sleep medication, greater sleep-related daytime dysfunction, and longer sleep onset latencies in PTSD patients, and is predictive of patients having experienced greater trauma exposure (Ulmer, C. S., et al., *Behav Med.,* 2013, 39: 111-121; Kario, K., et al., *Hypertension,* 2015, 66:1130-1137). In this example, a total of 576 patients diagnosed with resistant arterial hypertension (e.g., baseline office systolic BP≥160 mm Hg and 24-hour ambulatory systolic BP≥135 mm Hg) were either treated ("RDN treated"; n=382) with bilateral percutaneous, catheter-based renal sympathetic denervation (mean age of 58±11 years) or blindly treated ("blind control"; n=159) with a sham procedure (e.g., renal angiogram) or not treated ("control"; n=19) (Kario, K., et al., *Hypertension,* 2015, 66:1130-1137). Treatment included RF energy delivery to the renal artery using a Symplicity™ catheter system (Medtronic, Inc.). The renal neuromodulation ("RDN") treated group received up to six ablations rotated in 45 degree increments and approximately 5 mm apart for 2 minutes each in both renal arteries. Treatments were delivered from the first distal main renal artery bifurcation to the ostium proximally and were spaced longitudinally and rotationally under fluoroscopic guidance. BP variability, morning ambulatory, nighttime ambulatory and daytime ambulatory systolic BP was measured by 24-hour ambulatory BP monitoring before renal denervation and at 6 months after renal denervation.

In patients with resistant hypertension, renal denervation resulted in significant reduction in nighttime BP. For example, mean ambulatory nighttime BP measurements in the RDN treated group were reduced by 6.3±18.2 mm Hg (p<0.001; baseline of 151.5±18.3 mm Hg, p=0.24), whereas they were not significantly reduced (−1.7±19.2 mm Hg; p=0.233) from baseline (149.5±20.1 mm Hg, p=0.24) in the blind control+control group 6 months post-neuromodulation. These findings suggest that PTSD patients treated with renal neuromodulation will have decreased ambulatory nighttime systolic BP which will reduce the PTSD patient's likelihood (e.g., lower level of risk) of developing, progressing or worsening cardiovascular disease. These findings further suggest that PTSD patients treated with renal neuromodulation will improve one or more PTSD symptoms relating to hyperarousal and/or sleep disturbances (Ulmer, C. S., et al., *Behav Med.,* 2013, 39: 111-121).

Example 6

Example 6 describes a method for treating human patients diagnosed with PTSD with renal neuromodulation and anticipated outcomes of such treatment. In this example, human patients diagnosed with PTSD will be treated with renal denervation and a method of treatment includes modulating nerve tissue surrounding the main renal artery (e.g., locations along the main renal vessel, locations at or near the bifurcation, etc.) and/or modulating nerve tissue surrounding one or more primary branch trunks (e.g., proximal portion of one or more primary branch vessels distal to the bifurcation).

For patients undergoing distal main renal artery treatment, modulating nerve tissue includes forming a plurality of spaced-apart lesions at the distal segment of the renal artery and within a distance of approximately 6 mm proximal to the branch point within the renal artery using the Symplicity Spyral™ catheter, commercially available from Medtronic, Inc. For example, a first (e.g., most distal) lesion can be formed about 5-6 mm proximal from the bifurcation. Other multi-electrode, spiral/helical-shaped catheters for forming multiple lesions along the length of the vessel are also contemplated for these methods. For patients undergoing main artery treatment at a central segment of the main renal artery, the Symplicity Spyral™ catheter can be used to form a plurality of spaced-apart lesions (e.g., about 2 lesions to about 4 lesions) in a spiral/helical pattern along the central segment of the main renal artery. The catheter may also be moved proximally and/or distally to form multiple sets of lesions during a procedure.

For patients undergoing renal branch treatment, modulating nerve tissue includes forming up to about four lesions (e.g., about 2 lesions to about 4 lesions) in one or more primary branch trunks (e.g., from about 1 mm to about 6 mm distal to the primary bifurcation, in regions greater than 2 mm distal to the primary bifurcation). Modulation of nerve tissue at branch trunk treatment sites and/or different combinations of treatment sites within the renal vasculature (e.g., locations along the main renal vessel, locations at or near the bifurcation, etc.) can also be performed using the multi-electrode Symplicity Spyral™ catheter. Other multi-electrode, spiral/helical-shaped catheters having a tighter spiral/helix (e.g., smaller pitch) for forming multiple lesions close in proximity along the length of the vessel are contemplated for these methods.

In a particular example, a method for efficaciously neuromodulating renal nerve tissue in a human patient can include advancing a multi-electrode Symplicity Spyral™ catheter to a first renal artery branch vessel approximately 6 mm distal to the bifurcation. Following retraction of a guidewire and/or straightening sheath, the Symplicity Spyral™ catheter can transform to a spiral/helically-shaped configuration that accommodates the inner diameter of a typical renal artery and/or the branches of the renal artery (e.g., about 2-10 mm), placing the electrodes (e.g., 4 electrodes) in contact with the vessel wall. A first (e.g., most distal) lesion can be formed about 5-6 mm distal to the bifurcation. Following treatment at the first renal artery branch, the catheter can be withdrawn into the main renal vessel and then advanced under fluoroscopy into a second renal artery branch and the treatment procedure can be repeated. Some methods can include treating two branch vessels at the proximal trunk segment of the branch vessel. Other methods can include treating greater than two or all of the primary branch vessels branching from the main renal vessel (e.g., distal to a primary bifurcation). As described above, these methods may also include combining neuromodulation of renal nerve tissue surrounding one or more primary branch trunks with neuromodulation of renal nerve tissue at additional treatment locations (e.g., locations along the main renal vessel, locations at or near the bifurcation, etc.). Other methods can include advancing a multi-electrode Symplicity Spyral™ catheter to a first renal artery branch vessel approximately 10 mm distal to the bifurcation, with a first (e.g., most distal) lesion formed about 9-10 mm distal to the bifurcation.

Physiological biomarkers, such as systemic catecholamines and/or their subsequent degradation products could be measured in either plasma, serum or urine to serve as surrogate markers to measure procedural efficacy such as described in International Patent Application No. PCT/US2015/047568, filed Aug. 28, 2015, and incorporated herein by reference in its entirety.

It is anticipated that treating a human patient diagnosed with PTSD or having an increased risk of developing PTSD following a traumatic event (e.g., a predisposition, having one or more biomarkers suggesting an increased likelihood, etc.) or having one or more measurable risk factors predictive for the development of PTSD following a traumatic event, with renal neuromodulation, at one or more of the described treatment locations, will inhibit sympathetic neural activity in the renal nerve in a manner that reduces a central sympathetic drive (e.g., as correlated with whole body norepinephrine spillover and/or renal norepinephrine spillover) by greater than about 20%, about 30%, about 40%, about 50% or greater than about 60% in about 1 month, in about 3 months, in about 6 months or in about 12 months, or in another embodiment, in about 3 months to about 12 months, after renal neuromodulation treatment. Reduction in central sympathetic drive is anticipated to result in a therapeutically beneficial improvement in one or more measurable physiological parameters corresponding to an incidence of PTSD, and/or a severity of PTSD in the patient.

Example 7

Example 7 describes a method for determining male human patients who have a calculated risk score for determining PTSD status (e.g., diagnosis) at or above a threshold PTSD risk score and treating such male patients with targeted sympathetic neuromodulation of renal SNS neural fibers innervating the kidney. In this example, male human patients having a calculated PTSD risk score meeting or exceeding a threshold PTSD risk score will be treated with renal neuromodulation to improve the male patient's PTSD risk score and/or lower the male patient's PTSD risk score (e.g., in a manner that improves the male patient's PTSD status, reverses the male patient's PTSD diagnosis, and/or improves one or more symptoms or contributing factors associated with PTSD in the male patient).

Male patients presenting one or more risk factors or indicators predictive for PTSD will be assessed for other possible risk factors and a PTSD risk score will be calculated. In this example, a male patient will fill out a questionnaire or otherwise have an attending physician assess risk factors. A PTSD risk score calculator based on risk factor data to determine a probability or likelihood of PTSD status (e.g., diagnosis) in a male individual is shown in FIG. 10. The PTSD risk score calculator shown in FIG. 10 is derived from data provided in a study to develop a model of a technique to assess psychological trauma and screen the patient for symptoms, risk factors and indicators of PTSD using data from the New York PTSD Risk Score (NYPRS) study (Boscarino, J. A., et al., *Psychiatry Res.*, 2012, 200: 827-834).

Referring to the PTSD risk score calculator shown in FIG. 10, a male patient will be queried and assessed for core PTSD symptoms, depression symptoms, level of trauma exposure, sleep disturbances, and whether the patient has regular access to healthcare. In addition to these five clinical measures, the male patient may also be examined and/or tested by a physician for determination of other physiological variables pertaining to the SNS such as, for example, heart rate variability, heart rate reactions to stress, whole body MSNA levels and systolic blood pressure (not shown in FIG. 10). In this example, the input to the calculator will yield both a patient-specific PTSD risk score as well as an indication as to whether RDN treatment is recommended. In this example, the threshold PTSD risk score for men is 184. An indication of RDN recommendation may be based on whether the patient's PTSD risk score is at or above the threshold PTSD risk score, either alone or in combination with one or more physician-administered tests assessing SNS activity or systolic blood pressure level.

As illustrated in FIG. 10, a hypothetical male patient reports experiencing 3 out of 4 core PTSD symptoms (on the PCPS portion), positive indication on 2 lifetime depression items (on the depression screening portion), 2 incidents of trauma exposure in his lifetime, experiencing sleep disturbance(s) within the past 12 months, and having access to medical care. A physician-administered SNS test assessing heart rate variability indicated the patient's SDNN intervals were less than the 50 ms threshold, and the patient failed to meet a threshold level in a baroreflex sensitivity test. The hypothetical male patient's PTSD risk score of 267 exceeds the threshold level determination for PTSD diagnosis and for receiving RDN treatment with or without the additional SNS tests (or ascertaining a systolic blood pressure for the patient). Following bilateral renal neuromodulation treatment, the hypothetical male patient may have improvement in one or more measurable risk factors (e.g., heart rate variability, baroreceptor sensitivity, severity or frequency of sleep disturbances, etc.), and/or reported risk factors pertaining to core PTSD symptoms and/or depression symptoms, that improves the patient's PTSD risk score, and in some cases, to levels below the threshold PTSD risk score level(s).

Example 8

Example 8 describes a method for determining female human patients who have a calculated risk score for determining PTSD status (e.g., diagnosis) at or above a threshold PTSD risk score and treating such female patients with targeted sympathetic neuromodulation of renal SNS neural fibers innervating the kidney. In this example, female human patients having a calculated PTSD risk score meeting or exceeding a threshold PTSD risk score will be treated with renal neuromodulation to improve the female patient's PTSD risk score and/or lower the female patient's PTSD risk score (e.g., in a manner that improves the female patient's PTSD status, reverses the female patient's PTSD diagnosis, and/or improves one or more symptoms or contributing factors associated with PTSD in the female patient).

Female patients presenting one or more risk factors or indicators predictive for PTSD will be assessed for other possible risk factors and a PTSD risk score will be calculated. In this example, a female patient will fill out a questionnaire or otherwise have an attending physician assess risk factors. A PTSD risk score calculator based on risk factor data to determine a probability or likelihood of PTSD status (e.g., diagnosis) in a female individual is shown in FIG. 11. The PTSD risk score calculator shown in FIG. 11 is derived from data provided in a study to develop a model of a technique to assess psychological trauma and screen the patient for symptoms, risk factors and indicators of PTSD using data from the New York PTSD Risk Score (NYPRS) study (Boscarino, J. A., et al., *Psychiatry Res.*, 2012, 200: 827-834).

Referring to the PTSD risk score calculator shown in FIG. 11, a female patient will be queried and assessed for core PTSD symptoms, depression symptoms, level of trauma exposure, sleep disturbances, and whether the patient has regular access to healthcare. In addition to these five clinical measures, the female patient may also be examined and/or tested by a physician for determination of the patient's systolic blood pressure (FIG. 11) or other physiological variables pertaining to the SNS such as, for example, heart rate variability, heart rate reactions to stress, and whole body MSNA levels (not shown in FIG. 11). In this example, the input to the calculator will yield both a patient-specific PTSD risk score as well as an indication as to whether RDN treatment is recommended. In this example, the threshold PTSD risk score for women is 139. An indication of RDN recommendation may be based on whether the patient's PTSD risk score is at or above the threshold PTSD risk score, either alone or in combination with systolic blood pressure level and/or one or more physician-administered tests assessing SNS activity.

As illustrated in FIG. 11, a hypothetical female patient reports experiencing 3 out of 4 core PTSD symptoms (on the PCPS portion), negative indication on 2 lifetime depression items (on the depression screening portion), 3 incidents of trauma exposure in her lifetime, experiencing sleep disturbance(s) within the past 12 months, and having access to medical care. The female patient's office systolic blood pressure registered at 120 mmHg and within the normal range. The hypothetical female patient's PTSD risk score of 168 exceeds the threshold level determination for PTSD diagnosis and for receiving RDN treatment with or without the ascertaining a systolic blood pressure for the patient. In this example, the female patient was not hypertensive or pre-hypertensive. Following bilateral renal neuromodulation treatment, the hypothetical female patient may have improvement in one or more measurable risk factors (e.g., heart rate variability, baroreceptor sensitivity, heart rate under stress, severity or frequency of sleep disturbances, etc.), and/or reported risk factors pertaining to core PTSD symptoms, that improves the patient's PTSD risk score, and in some cases, to levels below the threshold PTSD risk score level(s).

VIII. Further Examples

1. In a patient diagnosed with post-traumatic stress disorder (PTSD), a method comprising:
   intravascularly positioning a neuromodulation assembly within a renal blood vessel of the patient and adjacent to a renal nerve of the patient; and
   at least partially inhibiting sympathetic neural activity in the renal nerve of the patient via the neuromodulation assembly,
   wherein at least partially inhibiting sympathetic neural activity results in a therapeutically beneficial improvement in a measurable parameter associated with the PTSD of the patient.

2. The method of example 1 wherein at least partially inhibiting sympathetic neural activity in the patient in a manner that results in a therapeutically beneficial improvement in a measurable parameter associated with PTSD comprises improving a sleep pattern and/or a sleep quality.

3. The method of example 1 or example 2 wherein at least partially inhibiting sympathetic neural activity in the patient in a manner that results in a therapeutically beneficial improvement in a measurable parameter associated with PTSD comprises reducing a level of insomnia in the patient.

4. The method of any one of examples 1-3 wherein reducing sympathetic neural activity in the patient in a manner that results in a therapeutically beneficial improvement in a measurable parameter associated with PTSD comprises reducing a nocturnal blood pressure in the patient.

5. The method of any one of examples 1-4 wherein at least partially inhibiting sympathetic neural activity in the patient in a manner that results in a therapeutically beneficial improvement in a measurable parameter associated with PTSD comprises improving one or more depression-related symptoms in the patient.

6. The method of example 5 wherein improving one or more depression-related symptoms in the patient includes improving one or more of feelings of sadness, apathy, mood swings, loss of interest or pleasure in activities, guilt, anxiety, insomnia, restless sleep, excess sleepiness, fatigue, excessive hunger, loss of appetite, irritability, excessive crying, lack of concentration, slowness in activity and thoughts of suicide in the patient.

7. The method of example 5 wherein improving one or more depression-related symptoms in the patient includes reducing a level of depression-related symptoms or a number of depression-related symptoms as reported on a depression inventory scale.

8. The method of example 7 wherein improving one or more depression-related symptoms in the patient includes reducing a level of depression-related symptoms in the patient by at least about 5%, at least about 10%, at least about 20% or at least about 40%.

9. The method of example 7 wherein improving one or more depression-related symptoms in the patient includes reducing a number of depression-related symptoms in the patient by at least about 5%, at least about 10%, at least about 20% or at least about 40% within about three months to about 12 months after at least partially inhibiting sympathetic neural activity in the patient by delivering energy to the renal nerve.

10. The method of any one of examples 5-9 wherein the patient is male.

11. The method of example 1 wherein at least partially inhibiting sympathetic neural activity in the patient in a manner that results in a therapeutically beneficial improvement in a measurable parameter associated with PTSD comprises improving a patient PTSD risk score on a PTSD screening tool.

12. The method of example 11 wherein at least partially inhibiting sympathetic neural activity in the patient reduces a blood pressure of the patient, thereby improving a patient PTSD risk score.

13. The method of any one of examples 1-12 wherein reducing sympathetic neural activity in the renal nerve further reduces muscle sympathetic nerve activity (MSNA) in the patient.

14. The method of any one of examples 1-13 wherein reducing sympathetic neural activity in the renal nerve further reduces whole body norepinephrine spillover in the patient.

15. The method of example 14 wherein the whole body norepinephrine spillover is reduced by at least about 20% in about one month after reducing sympathetic neural activity in the renal nerve.

16. The method of example 14 wherein the whole body norepinephrine spillover is reduced by greater than about 40% in about three months to about 12 months after reducing sympathetic neural activity in the renal nerve.

17. The method of any one of examples 1-16 wherein the patient is currently administered one or more pharmaceutical drugs for the PTSD, and wherein at least partially inhibiting sympathetic neural activity in the patient in a manner that results in a therapeutically beneficial improvement in a measurable parameter associated with PTSD comprises reducing at least one of a number of or a measured dosage of pharmaceutical drugs administered to the patient for the PTSD.

18. The method of example 17 wherein the pharmaceutical drugs include one or more of an antidepressant, an anti-anxiety drug, an anti-psychotic drug, an insomnia drug or an anti-inflammatory drug.

19. The method of any one of examples 1-17 wherein the patient is normotensive.

20. In a patient exposed to a traumatic event, a method of reducing a risk of the patient developing post-traumatic stress disorder (PTSD) relating to the traumatic event, the method comprising:

intravascularly positioning a catheter carrying a neuromodulation assembly adjacent to a renal sympathetic nerve in the patient;

delivering energy to the renal sympathetic nerve via the neuromodulation assembly to attenuate neural traffic along the renal sympathetic nerve; and removing the catheter and neuromodulation assembly from the patient after treatment, wherein attenuating neural traffic along the renal sympathetic nerve reduces a risk of the patient developing PTSD relating to the traumatic event.

21. The method of example 20 wherein a risk of developing PTSD is calculated using a PTSD screening tool, and wherein a post-neuromodulation PTSD risk score, as calculated by the PTSD screening tool, for the development of PTSD for the patient is lower than an initial PTSD risk score.

22. The method of example 20 or example 21 wherein attenuating neural traffic along the renal sympathetic nerve further results in one or more of— increasing heart rate variability in the patient;
increasing baroreceptor sensitivity in the patient;
reducing a level of glucocorticoid sensitivity in the patient;
reducing a resting heart rate in the patient;
reducing a systolic blood pressure of the patient;
reducing a nocturnal blood pressure in the patient;
reducing muscle sympathetic nerve activity (MSNA) in the patient; and reducing a level of an inflammatory biomarker in the patient.

23. The method of example 22 wherein the inflammatory biomarker is at least one of interleukin-6 and C-reactive protein.

24. The method of any one of examples 20-23 wherein the patient is diagnosed with one or more of heightened startle responses, low heart rate variability, and an increased number of glucocorticoid receptors on the patient's leukocytes.

25. The method of example 20 wherein the patient has a polymorphism in at least one of the genes encoding for FK506-binding protein 5 (FKBP5), brain-derived neurotrophic factor (BDNF), and serotonin transporter (SLC6A4) that provides an increased likelihood of developing PTSD.

26. The method of any one of examples 20-25 wherein the patient is diagnosed with acute stress disorder.

27. The method of any of examples 20-26 wherein patient has one or more PTSD risk factors selected from the group consisting of depression, increased substance usage, hypertension, elevated norepinephrine whole body spillover, exposure to multiple traumatic events, female, widowed or divorced marital status, and adverse childhood experience.

28. The method of any one of examples 20-27 wherein attenuating neural traffic along the renal sympathetic nerve comprises at least partially ablating the renal sympathetic nerve.

29. The method of any one of examples 20-27 wherein attenuating neural traffic along the renal sympathetic nerve comprises at least partially disrupting communication along the renal sympathetic nerve.

30. The method of any one of examples 20-27 wherein attenuating neural traffic along the renal sympathetic nerve comprises irreversibly disrupting communication along the renal sympathetic nerve.

31. The method of any one of examples 20-27 wherein attenuating neural traffic along the renal sympathetic nerve comprises delivering an energy field to the renal sympathetic nerve via the neuromodulation assembly.

32. The method of example 31 wherein delivering an energy field to the renal sympathetic nerve comprises delivering at least one of radio frequency energy, ultrasound energy, high intensity ultrasound energy, laser energy, and microwave energy via the neuromodulation assembly.

33. The method of any one of examples 20-32 wherein the patient is diagnosed with prehypertension or hypertension, and wherein attenuating neural traffic along the renal sympathetic nerve further reduces whole body norepinephrine spillover in the patient in a manner that reduces the risk of developing PTSD associated with the traumatic event in the patient.

34. A method for improving a patient's risk score corresponding to a post-traumatic stress disorder (PTSD) status in the patient, the method comprising:
intravascularly positioning a catheter carrying a neuromodulation assembly within a renal blood vessel and adjacent to a renal sympathetic nerve in the patient;
delivering energy to the renal sympathetic nerve via the neuromodulation assembly to attenuate neural traffic along the renal sympathetic nerve; and
removing the catheter and neuromodulation assembly from the patient after treatment,
wherein attenuating neural traffic along the renal sympathetic nerve results in improving the patient's risk score corresponding to the PTSD status of the patient.

35. The method of example 34 wherein improving the patient's risk score corresponding to the PTSD status of the patient includes one or more of reducing the patient's nocturnal blood pressure, reducing a level of systemic inflammation in the patient, improving a patient's sleep quality, improving one or more depression-related symptoms, improving a patient's appetite and improving a patient's body mass index.

36. The method of example 34 or example 35 wherein the patient is diagnosed with pre-hypertension or hypertension, and wherein improving the patient's risk score corresponding to the PTSD status in the patient includes reducing the patient's blood pressure.

37. The method of any one of examples 34-36 wherein a patient's risk score corresponding to the PTSD status of the patient is reduced by at least about 10%, at least about 15%, at least about 20%, at least about 30% or at least about 40%.

38. A method for improving a post-traumatic stress disorder (PTSD) risk score for a human patient diagnosed with PTSD, the method comprising performing a renal neuromodulation procedure in the patient diagnosed with PTSD, wherein a post-neuromodulation risk score is lower than an initial risk score of the patient diagnosed with PTSD.

39. The method of example 38 wherein the post-neuromodulation risk score is lower than the initial risk score by about 5%, about 10%, about 20% or about 30%.

40. The method of example 38 or example 39 wherein the initial risk score indicates the patient is at risk of having PTSD if the initial risk score is greater than a threshold risk score.

41. The method of example 40 wherein the threshold risk score for a male is greater than the threshold risk score for a female.

42. The method of any one of examples 38-41 wherein the initial risk score and the post-neuromodulation risk score are determined using a PTSD screening tool for determining a severity of PTSD in the patient.

43. The method of any one of examples 38-42 wherein the initial risk score and the post-neuromodulation risk score are based upon one or more factors comprising a psychological evaluation, depression-related symptoms, type of trauma exposure, severity of trauma exposure, number of instances of trauma exposure, sleep disturbances and access to healthcare.

44. A method for managing post-traumatic stress disorder (PTSD) in a human patient, the method comprising:
transluminally positioning an energy delivery element of a catheter within a renal blood vessel of the patient and adjacent to renal sympathetic neural fibers in the patient; and
at least partially ablating the renal sympathetic neural fibers via the energy delivery element,
wherein at least partially ablating the renal sympathetic neural fibers results in a therapeutically beneficial improvement in a measurable parameter associated with PTSD of the patient.

45. The method of example 44 wherein at least partially ablating the renal sympathetic neural fibers in the patient in a manner that results in a therapeutically beneficial improvement in a measurable parameter associated with PTSD comprises improving one or both of a sleep pattern or a sleep quality.

46. The method of example 44 or 45 wherein at least partially ablating the renal sympathetic neural fibers in the patient in a manner that results in a therapeutically beneficial improvement in a measurable parameter associated with PTSD comprises reducing a nocturnal blood pressure in the patient.

47. The method of any one of examples 44-46 wherein at least partially ablating the renal sympathetic neural fibers in the patient in a manner that results in a therapeutically beneficial improvement in a measurable parameter associated with PTSD comprises improving one or more depression-related symptoms in the patient.

48. The method of any one of examples 44-46 wherein at least partially ablating the renal sympathetic neural fibers further results in reducing an incidence of one or more of hypertension, cardiovascular disease, obesity, diabetes, insulin resistance, systemic inflammation, and major depressive disorder in the patient.

49. The method of any one of examples 44-48, further comprising administering one or more pharmaceutical drugs to the patient, wherein the pharmaceutical drugs are selected from the group consisting of antidepressants, anti-anxiety drugs and anti-inflammatory drugs.

50. The method of any one of examples 44-48 wherein at least partially ablating the renal sympathetic neural fibers of the patient via the energy delivery element comprises delivering a thermal electric field to the sympathetic neural fibers via at least one electrode.

51. A method for treating a patient that experienced a traumatic event at least one month prior and that can answer affirmatively, if asked, to at least three of the following statements:
a) you had repeated bad dreams or nightmares or had disturbing or unpleasant memories, thoughts or images that kept coming into your mind whether you wanted to think of them or not,
b) you deliberately tried hard not to think about something that happened to you or went out of your way to avoid certain places or activities that might remind you of something that happened in the past,
c) you felt you had to stay on guard much of the time or unexpected noises startled you more than usual, and
d) you felt cut off from other people, found it difficult to feel close to other people, or you could not feel things anymore or you had much less emotion than you used to have, the method comprising:
    intravascularly positioning a neuromodulation assembly within a renal blood vessel of the patient and adjacent to a renal nerve of the patient; and
    at least partially inhibiting sympathetic neural activity in the renal nerve of the patient via the neuromodulation assembly,
    wherein at least partially inhibiting sympathetic neural activity results in a therapeutically beneficial improvement in the patient's response to one or more of statements a-d.

IX. Conclusion

The above detailed descriptions of embodiments of the technology and methodology are not intended to be exhaustive or to limit the technology to the precise forms disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of reducing a risk of a patient exposed to a traumatic event developing post-traumatic stress disorder (PTSD) relating to the traumatic event, the method comprising:
    assessing a patient for risk of developing PTSD;
    identifying the patient as being at risk for developing PTSD from the assessing; and
    executing a renal denervation procedure based on the identifying, the renal denervation procedure comprising:
        intravascularly positioning a catheter carrying a neuromodulation assembly adjacent to a renal sympathetic nerve in the patient;
        delivering energy to the renal sympathetic nerve via the neuromodulation assembly to at least partially ablate the renal sympathetic nerve to attenuate neural traffic along the renal sympathetic nerve; and
        removing the catheter and neuromodulation assembly from the patient after treatment.

2. The method of claim 1 further comprising:
    administering a written questionnaire or a clinician administered test to establish a risk score both prior to and after executing the renal denervation procedure;
    comparing the risk scores; and
    repeating another execution of the renal denervation procedure based on the comparing.

3. The method of claim 1 wherein identifying the patient at risk of developing PTSD includes identifying the patient having one or more PTSD risk factors selected from the group consisting of depression, increased substance usage, hypertension, elevated norepinephrine whole body spillover, exposure to multiple traumatic events, female, widowed or divorced marital status, and adverse childhood experience.

4. The method of claim 1 wherein identifying the patient at risk of developing PTSD includes identifying the patient having one or more of heightened startle responses, low heart rate variability, or an increased number of glucocorticoid receptors on the patient's leukocytes.

5. The method of claim 1 wherein identifying the patient at risk of developing PTSD includes identifying the patient having a polymorphism in at least one of the genes encoding for FK506-binding protein 5 (FKBP5), brain-derived neurotrophic factor (BDNF), or serotonin transporter (SLC6A4).

6. The method of claim 1 wherein identifying the patient at risk of developing PTSD includes identifying the patient having at least one of:
    prehypertension;
    hypertension; or
    acute stress disorder.

7. The method of claim 1 wherein the assessing is executed prior to the patient having been diagnosed with PTSD.

8. The method of claim 1 wherein the assessing comprises determining an initial PTSD risk score of a patient, wherein the initial PTSD risk score corresponds to a measurable parameter of the patient, and wherein the identifying is based on the initial PTSD risk score being above a threshold risk score.

9. A method for improving a patient's risk score corresponding to a post-traumatic stress disorder (PTSD) status in the patient, the method comprising:
    determining an initial PTSD risk score of a patient, wherein the initial PTSD risk score corresponds to a measurable parameter of the patient;
    executing a renal denervation procedure if the initial PTSD risk score is above a threshold risk score, the renal denervation procedure comprising:
        intravascularly positioning a catheter carrying a neuromodulation assembly within a renal blood vessel and adjacent to a renal sympathetic nerve in the patient;
        delivering energy to the renal sympathetic nerve via the neuromodulation assembly to at least partially ablate the renal sympathetic nerve to attenuate neural traffic along the renal sympathetic nerve; and removing the catheter and neuromodulation assembly from the patient after treatment;

determining a post-neuromodulation PTSD risk score corresponding to the measurable parameter of the patient; and comparing the post-neuromodulation PTSD risk score to the initial PTSD risk score to determine if attenuating neural traffic along the renal sympathetic nerve results in improving the patient's PTSD risk score.

10. The method of claim 9 wherein the measurable parameter comprises a score generated by administering a written questionnaire or a clinician administered test and wherein a post-neuromodulation PTSD risk score is calculated by re-administering the written questionnaire or the clinician administered test.

11. The method of claim 9 wherein the initial PTSD risk score and the post-neuromodulation PTSD risk score are established based upon one or more measurable physiological parameters.

12. The method of claim 11 wherein the one or more measurable physiological parameters comprise one or more of:
   a nocturnal blood pressure in the patient;
   baroreceptor sensitivity in the patient;
   a level of glucocorticoid sensitivity in the patient;
   a resting heart rate in the patient;
   a systolic blood pressure of the patient;
   a level of an inflammatory biomarker in the patient;
   body mass; or
   skin conductance.

13. The method of claim 9 wherein delivering energy to the renal sympathetic nerve via the neuromodulation assembly comprises delivering at least one of:
   RF energy, microwave energy, optical energy, magnetic energy, ultrasound energy, thermal energy, or cryotherapeutic energy.

14. A method for treating post-traumatic stress disorder (PTSD), the method comprising:
   identifying a patient as having PTSD using at least one measurable parameter of the patient;
   intravascularly positioning a neuromodulation assembly within a renal blood vessel of the patient and adjacent to a renal nerve of the patient;
   delivering energy to the renal nerve via the neuromodulation assembly to at least partially ablate the renal nerve to inhibit sympathetic neural activity in the renal nerve of the patient; and
   identifying a change in the at least one measurable parameter in a post-neuromodulation measurement of the measurable parameter, wherein the change caused by at least partially inhibiting sympathetic neural activity being larger than a predetermined amount results in a therapeutically beneficial improvement in the measurable parameter associated with the PTSD of the patient.

15. The method of claim 14 wherein the measurable parameter associated with PTSD is a physiological parameter that includes one or more of:
   a nocturnal blood pressure in the patient;
   baroreceptor sensitivity in the patient;
   a level of glucocorticoid sensitivity in the patient;
   a resting heart rate in the patient;
   a systolic blood pressure of the patient;
   a level of an inflammatory biomarker in the patient; or
   skin conductance.

16. The method of claim 14 wherein the measurable parameter associated with PTSD comprises a patient PTSD risk score generated by administering a written questionnaire or a clinician administered test.

17. The method of claim 16 wherein at least partially inhibiting sympathetic neural activity in the patient reduces a blood pressure of the patient, thereby improving the patient PTSD risk score.

18. The method of claim 16 wherein at least partially inhibiting sympathetic neural activity in the patient in a manner that results in a therapeutically beneficial improvement in a measurable parameter associated with PTSD comprises improving one or more depression-related symptoms in the patient.

19. The method of claim 18 wherein improving one or more depression-related symptoms in the patient includes reducing a level of depression-related symptoms or a number of depression-related symptoms as reported on a depression inventory scale.

20. The method of claim 14 wherein delivering energy to the renal sympathetic nerve via the neuromodulation assembly comprises delivering at least one of:
   RF energy, microwave energy, optical energy, magnetic energy, ultrasound energy, thermal energy, or cryotherapeutic energy.

* * * * *